United States Patent
Hongo et al.

(10) Patent No.: US 7,745,203 B2
(45) Date of Patent: *Jun. 29, 2010

(54) BASE SEQUENCE DETECTION APPARATUS AND BASE SEQUENCE AUTOMATIC ANALYZING APPARATUS

(75) Inventors: Sadato Hongo, Tokyo (JP); Minoru Ishikawa, Tokyo (JP); Takiji Ishimura, Tokyo (JP); Shigeru Wakayama, Tokyo (JP); Shinji Yanaga, Tokyo (JP); Kenji Oki, Tokyo (JP); Jun Okada, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 222 days.

This patent is subject to a terminal disclaimer.

(21) Appl. No.: 11/045,646

(22) Filed: Jan. 31, 2005

(65) Prior Publication Data
US 2005/0158787 A1      Jul. 21, 2005

Related U.S. Application Data

(63) Continuation of application No. PCT/JP03/09684, filed on Jul. 30, 2003.

(30) Foreign Application Priority Data

| Jul. 31, 2002 | (JP) | ............................. 2002-223392 |
| Jul. 23, 2003 | (JP) | ............................. 2003-200440 |

(51) Int. Cl.
  *C12M 1/00*    (2006.01)
  *C12M 1/34*    (2006.01)
  *C12M 3/00*    (2006.01)

(52) U.S. Cl. ................. 435/283.1; 422/68.1; 422/82.01; 435/287.2; 435/288.5; 536/23.1; 536/24.3

(58) Field of Classification Search ............. 435/283.1, 435/287.2; 536/23.1, 24.3
See application file for complete search history.

(56) References Cited

U.S. PATENT DOCUMENTS 5,167,926 A * 12/1992 Kimura et al. ................ 422/67

(Continued)

FOREIGN PATENT DOCUMENTS

JP         10-318966         12/1998

(Continued)

OTHER PUBLICATIONS

U.S. Appl. No. 11/555,936, filed Nov 2, 2006, Okada, et al.

(Continued)

*Primary Examiner*—B J Forman
*Assistant Examiner*—Narayan K Bhat
(74) *Attorney, Agent, or Firm*—Oblon, Spivak, McClelland, Maier & Neustadt, L.L.P.

(57) ABSTRACT

A base sequence detection apparatus is provided with a channel formed on a base sequence detection chip. Working electrodes are formed along the channel and include a probe immobilized thereon, counter electrodes are formed on the inner surface of the channel and, reference electrodes are formed on the inner surface of the channel. An introduction port introduces solution or air from the upstream side of the channel, a delivery port delivers the solution or air in the channel, and the sample is injected into the channel through a sample injection port.

7 Claims, 47 Drawing Sheets

U.S. PATENT DOCUMENTS

| | | | |
|---|---|---|---|
| 5,451,500 | A | 9/1995 | Stapleton |
| 5,538,849 | A | 7/1996 | Uematsu et al. |
| 5,955,379 | A * | 9/1999 | Lennox et al. ............... 436/528 |
| 5,974,164 | A * | 10/1999 | Chee ........................... 382/129 |
| 6,066,448 | A * | 5/2000 | Wohlstadter et al. ............ 435/6 |
| 6,424,131 | B1 * | 7/2002 | Yamamoto et al. ........... 323/282 |
| 6,813,568 | B2 * | 11/2004 | Powell et al. .................. 702/31 |
| 7,172,897 | B2 * | 2/2007 | Blackburn et al. ........ 435/287.2 |
| 2001/0012612 | A1 * | 8/2001 | Petersen et al. .................. 435/5 |
| 2001/0051113 | A1 | 12/2001 | Juncosa et al. |
| 2002/0039743 | A1 | 4/2002 | Hashimoto et al. |
| 2003/0003504 | A1 * | 1/2003 | Bass et al. .................... 435/7.1 |

FOREIGN PATENT DOCUMENTS

| | | |
|---|---|---|
| JP | 2000-83647 | 3/2000 |
| JP | 2001-59846 | 3/2000 |
| JP | 2001-149097 | 6/2001 |
| JP | 2001-183341 | 7/2001 |
| JP | 2002-31638 | 1/2002 |
| JP | 2002-122597 | 4/2002 |
| JP | 2002-195997 | 7/2002 |
| WO | WO95/33846 * | 12/1995 |
| WO | WO 95/33846 | 12/1995 |
| WO | WO 97/12030 | 4/1997 |
| WO | WO 98/10267 | 3/1998 |
| WO | WO 98/20162 | 5/1998 |
| WO | WO 98/53300 | 11/1998 |
| WO | WO 99/67425 | 12/1999 |
| WO | WO 99/67628 | 12/1999 |
| WO | WO 01/44515 A2 | 6/2001 |
| WO | WO 01/54813 A2 | 8/2001 |
| WO | WO 01/56771 A2 | 8/2001 |

OTHER PUBLICATIONS

U.S. Appl. No. 11/082,877, filed Mar. 18, 2005, O'Uchi et al.
U.S. Appl. No. 11/377,265, filed Mar. 17, 2006, Hongo, et al.
H. Miyahara, et al."Electrochemical analysis of single nucleotide polymorphisms of p53 gene", TALANTA, vol. 56, No. 5, Apr. 1, 2002 pp. 829-835.
U.S. Appl. No. 11/682,484, filed Mar. 6, 2007, Okada, et al.
U.S. Appl. No. 12/408,980, filed Mar. 23, 2009, Okada, et al.

* cited by examiner

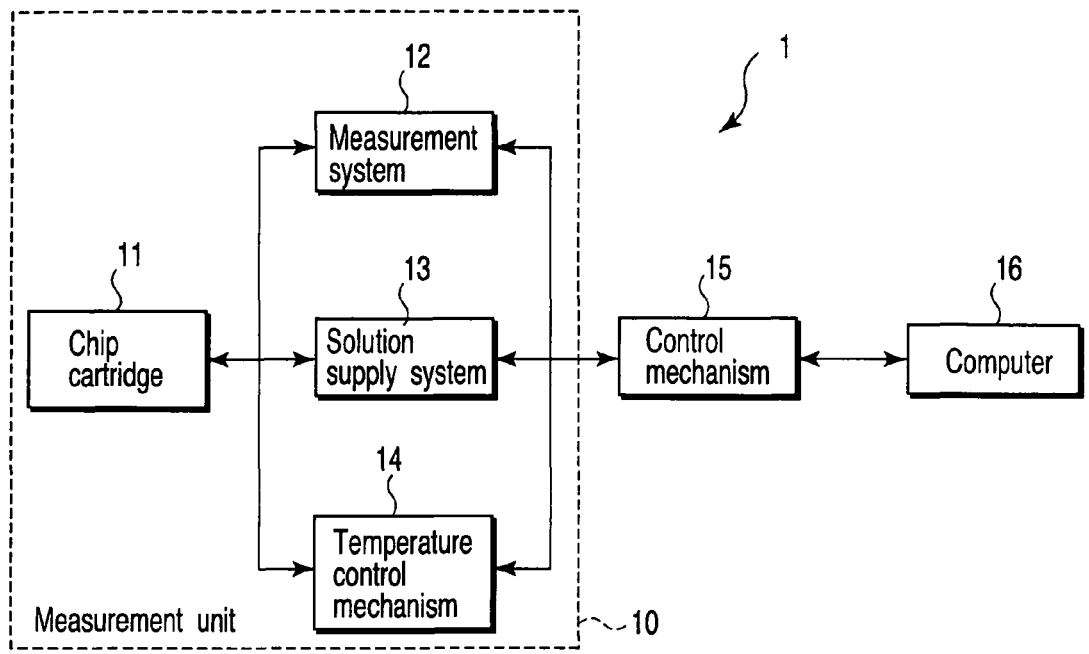
F I G. 1
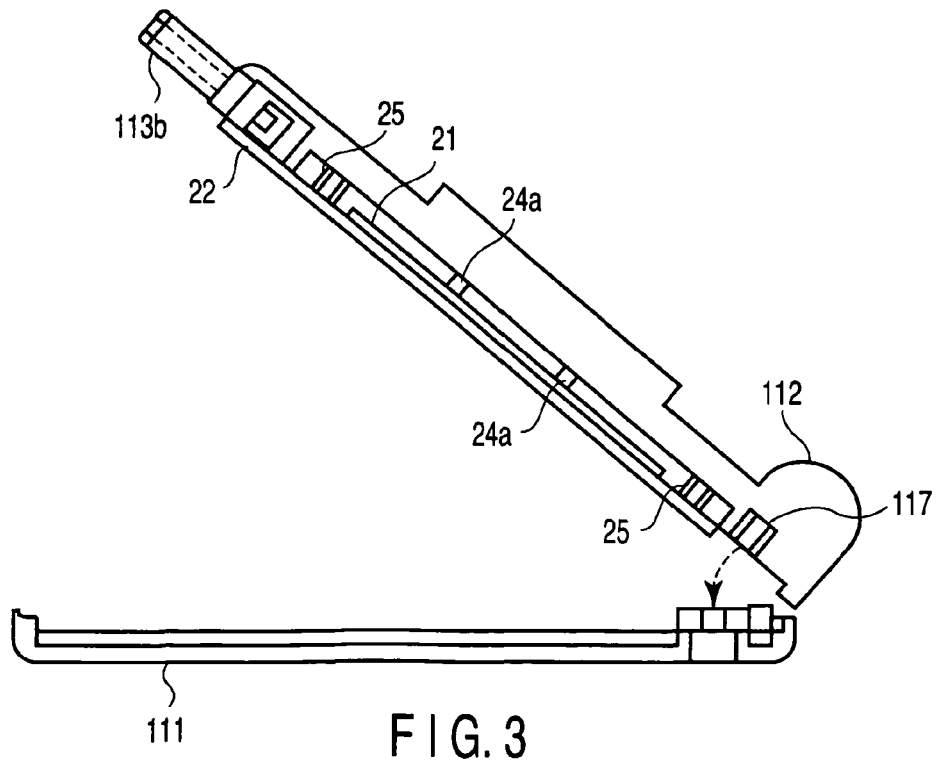
F I G. 3

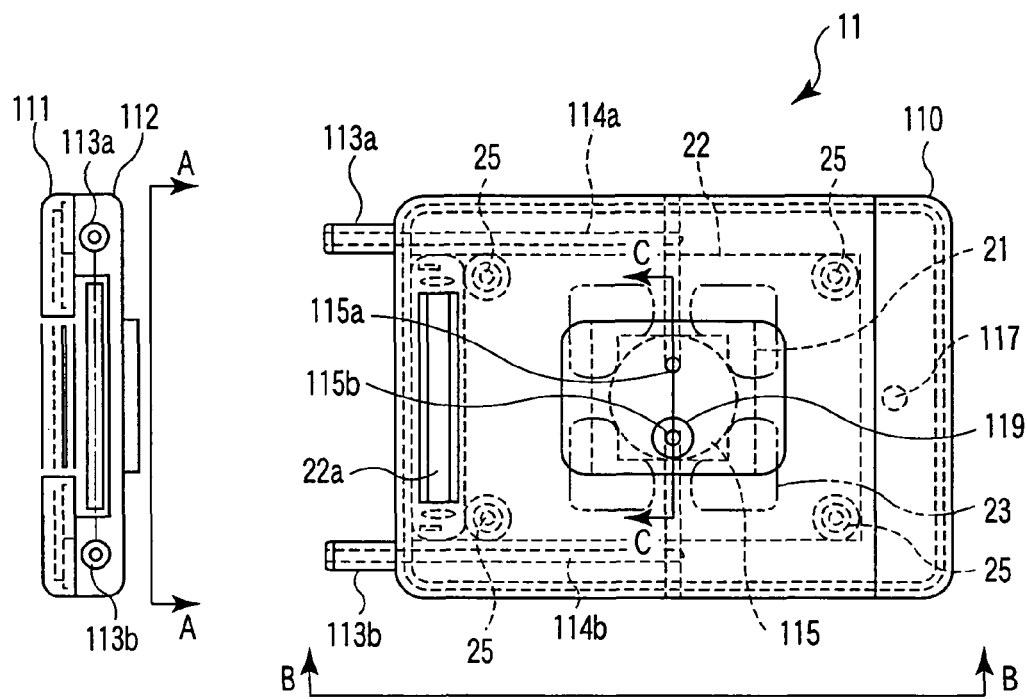
F I G. 2B  F I G. 2A
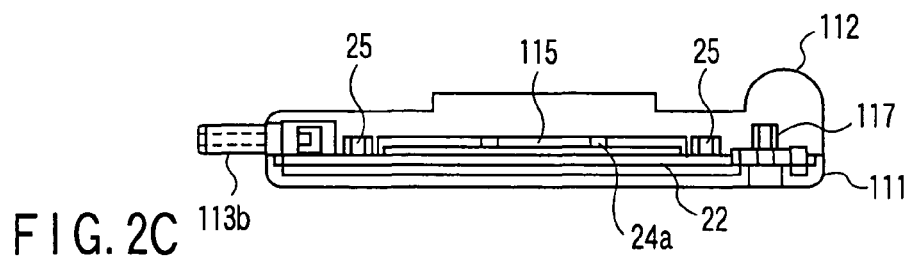
F I G. 2C
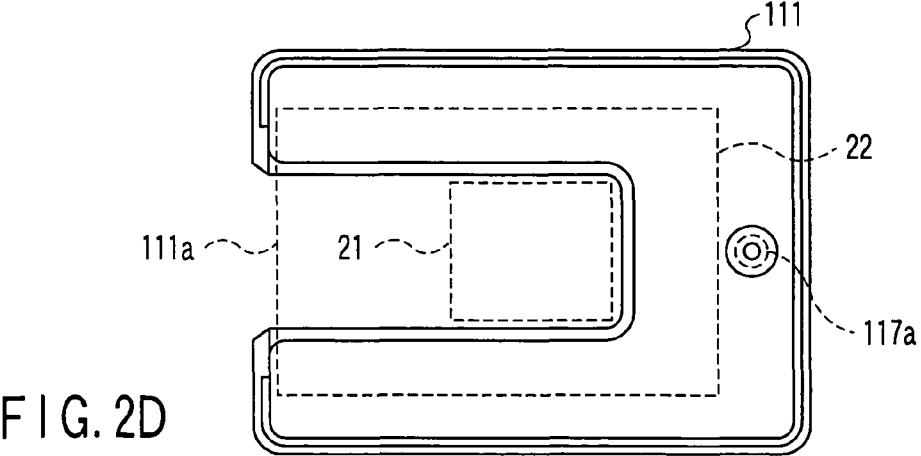
F I G. 2D

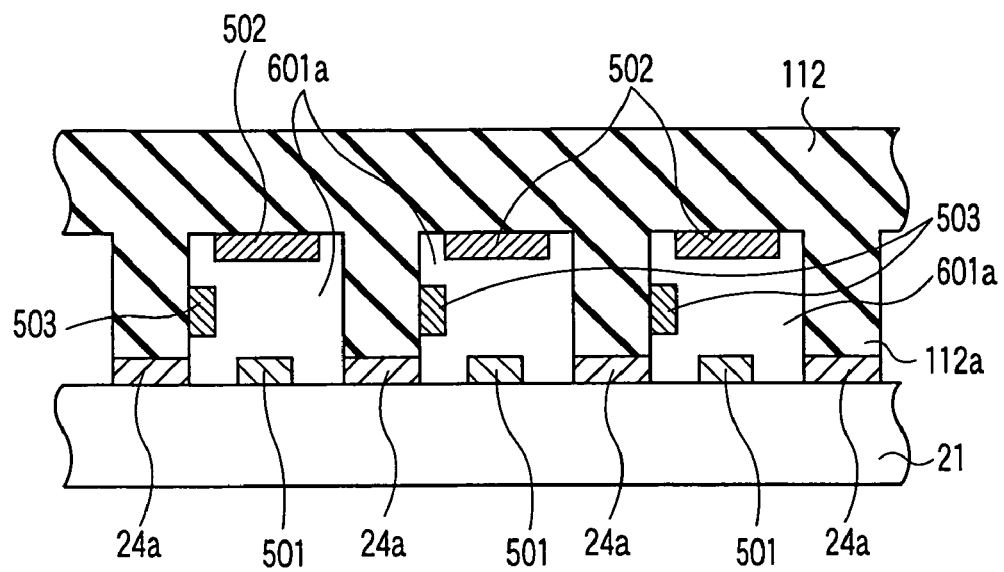
F I G. 7A
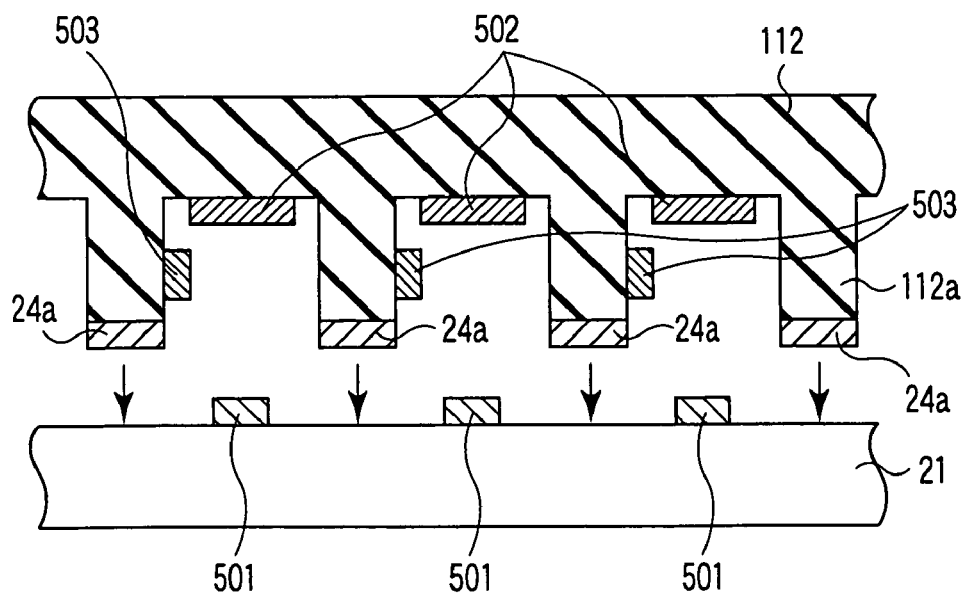
F I G. 7B

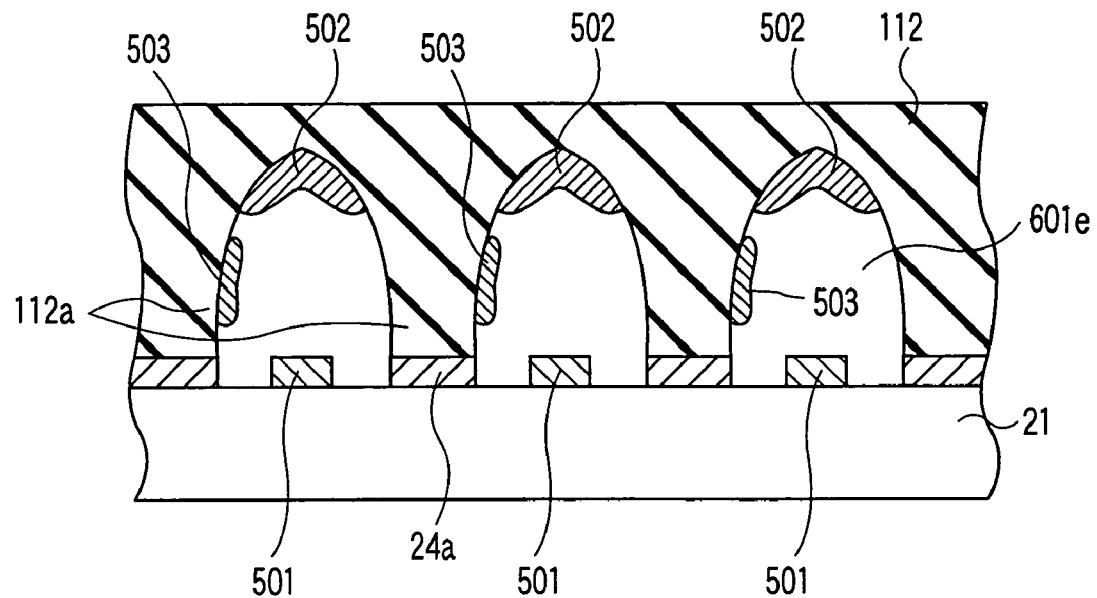
F I G. 10
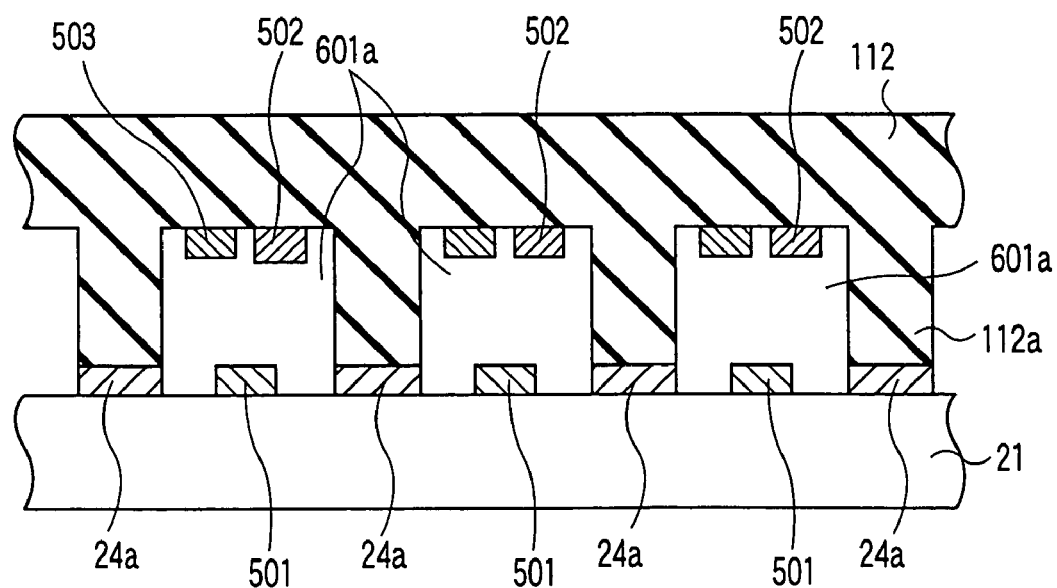
F I G. 11

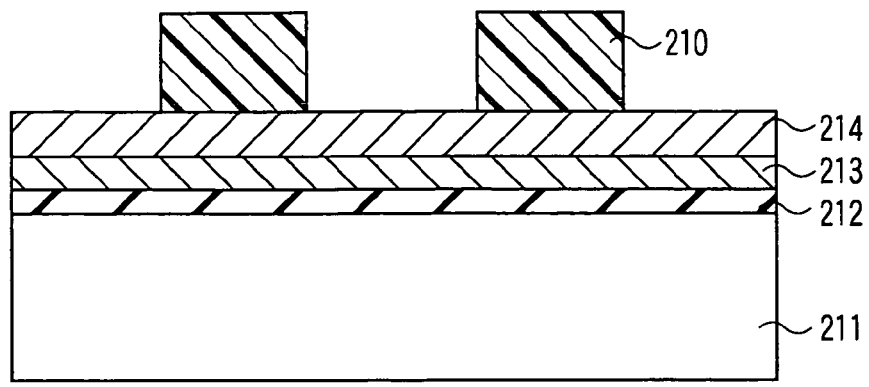
F I G. 15A
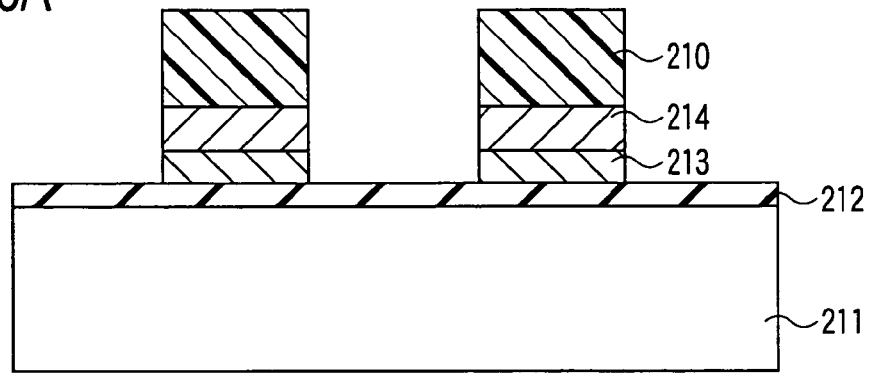
F I G. 15B
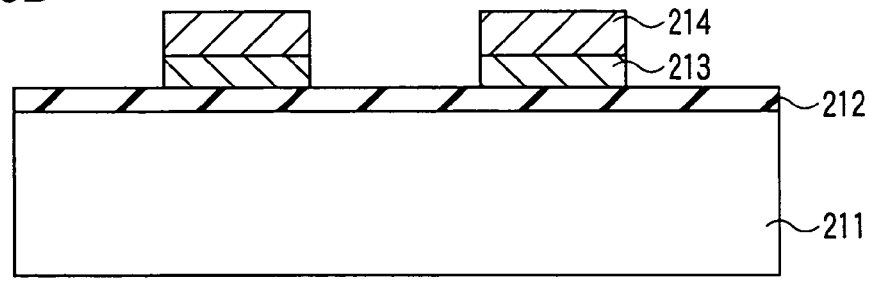
F I G. 15C
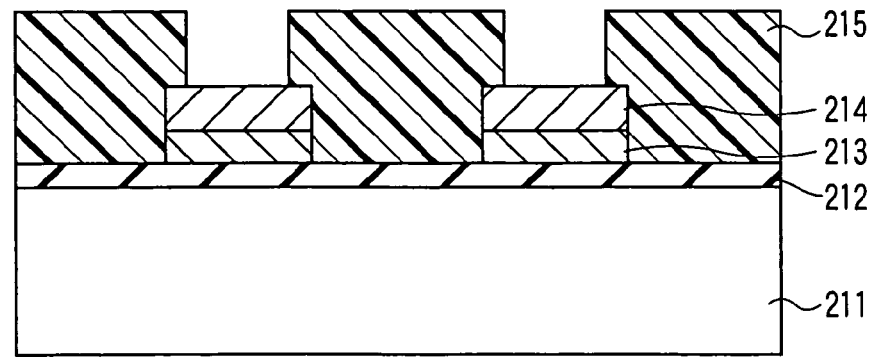
F I G. 15D

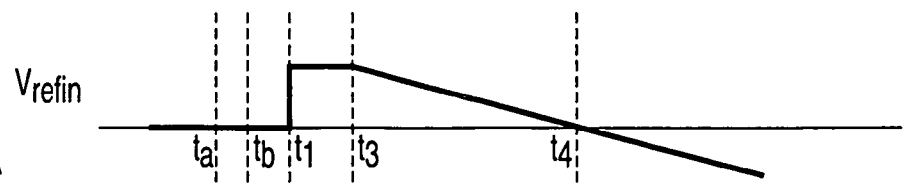
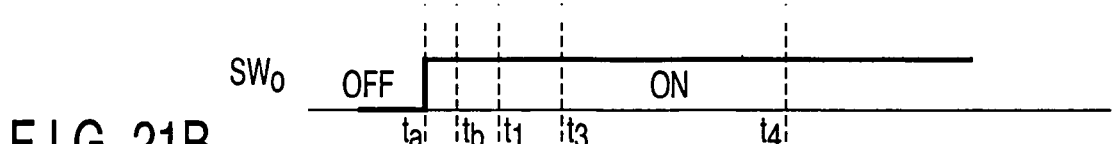
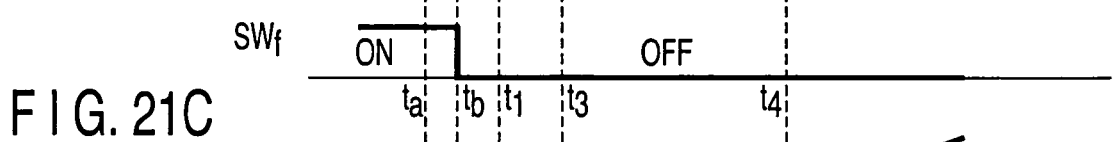
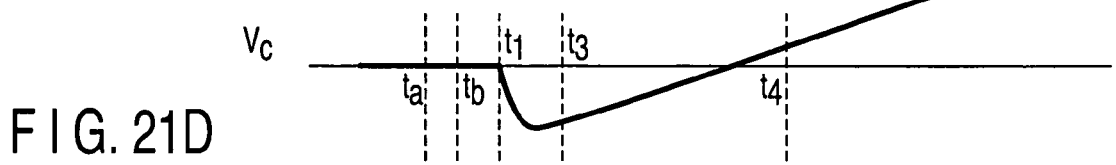
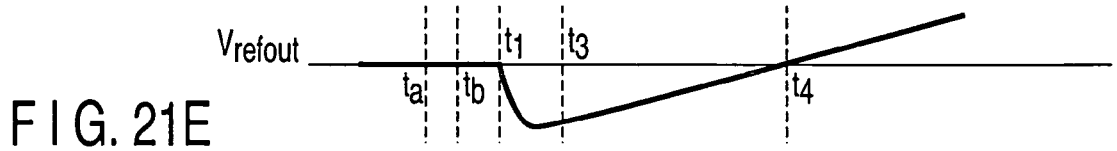
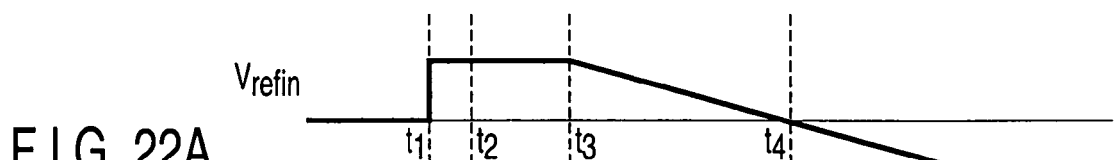
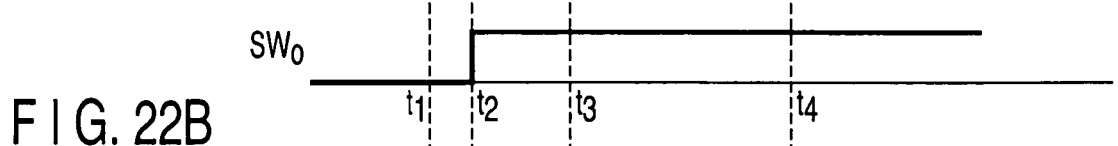
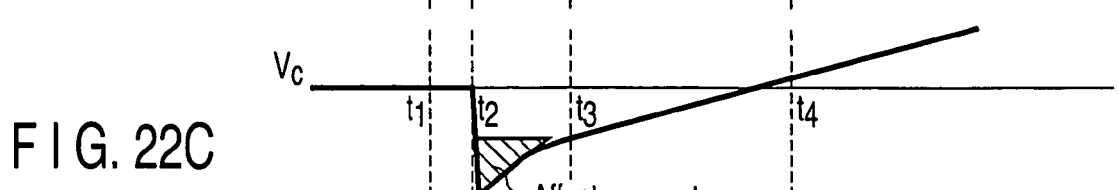
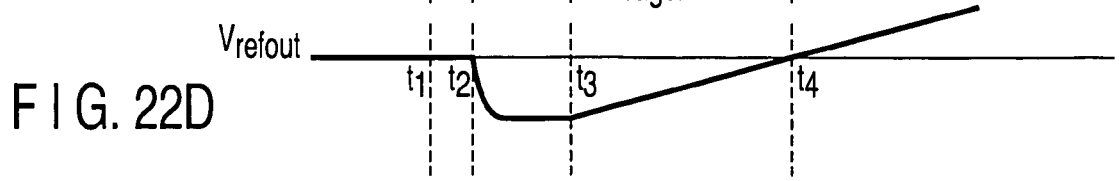

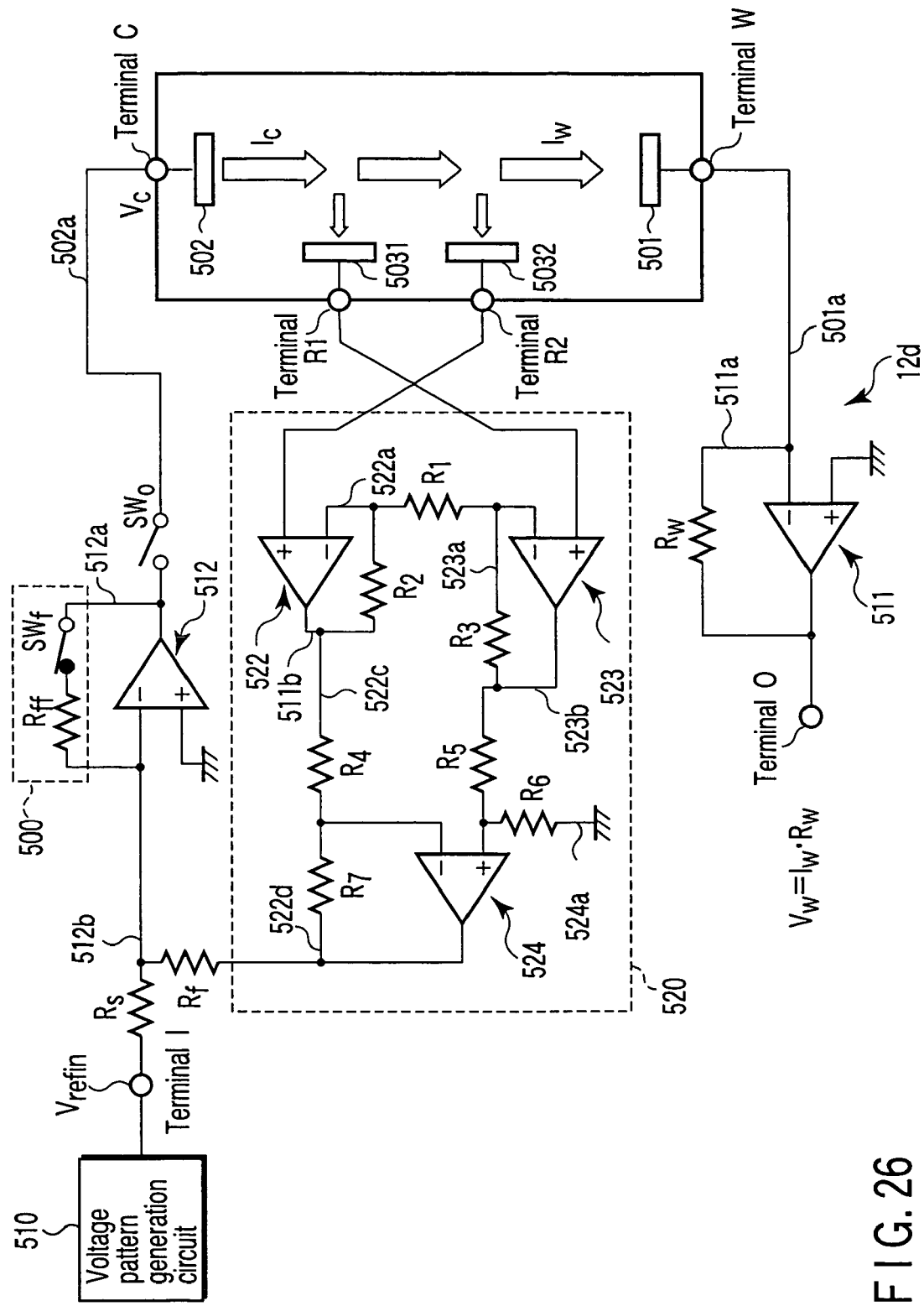
F I G. 26

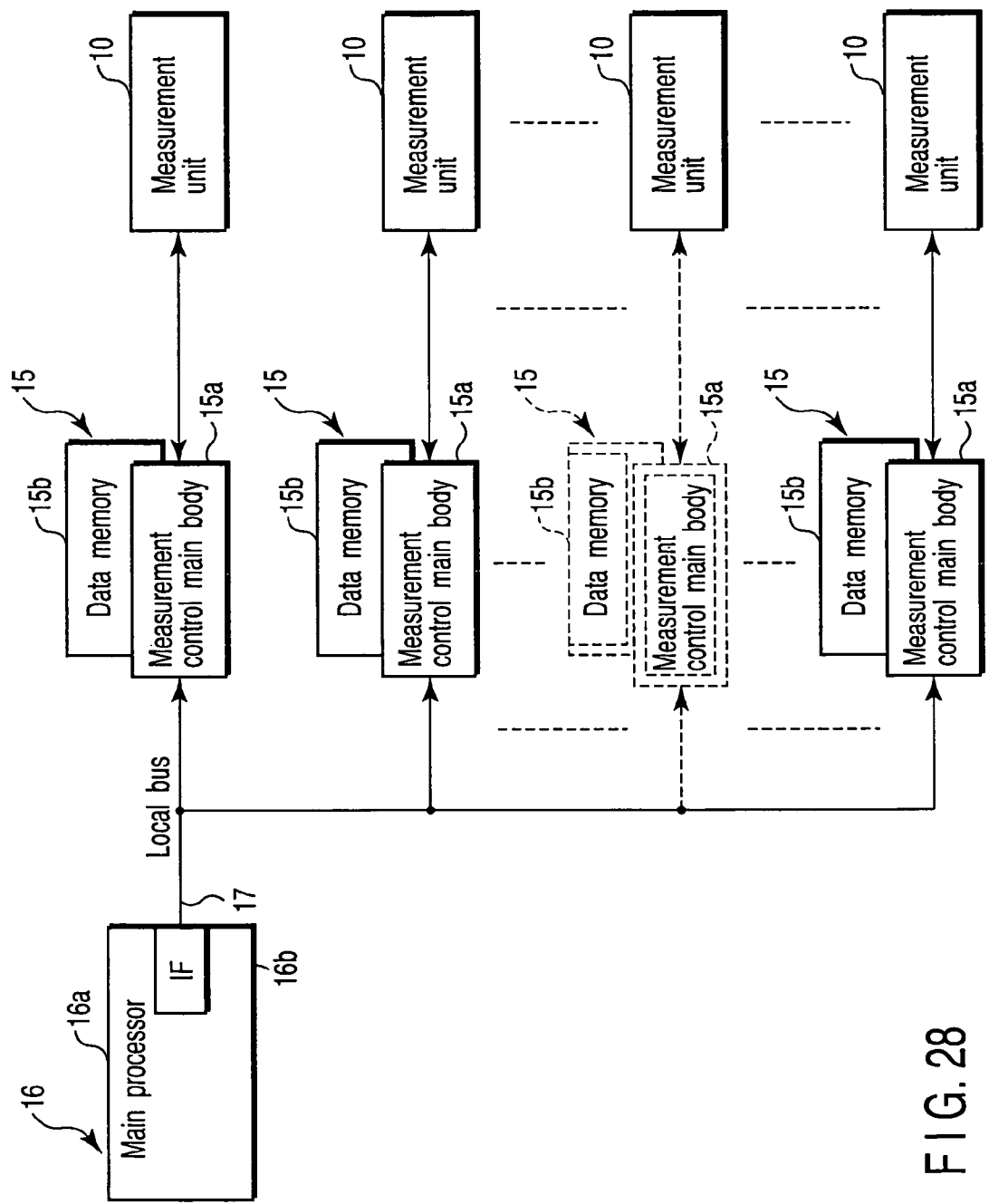
F I G. 28

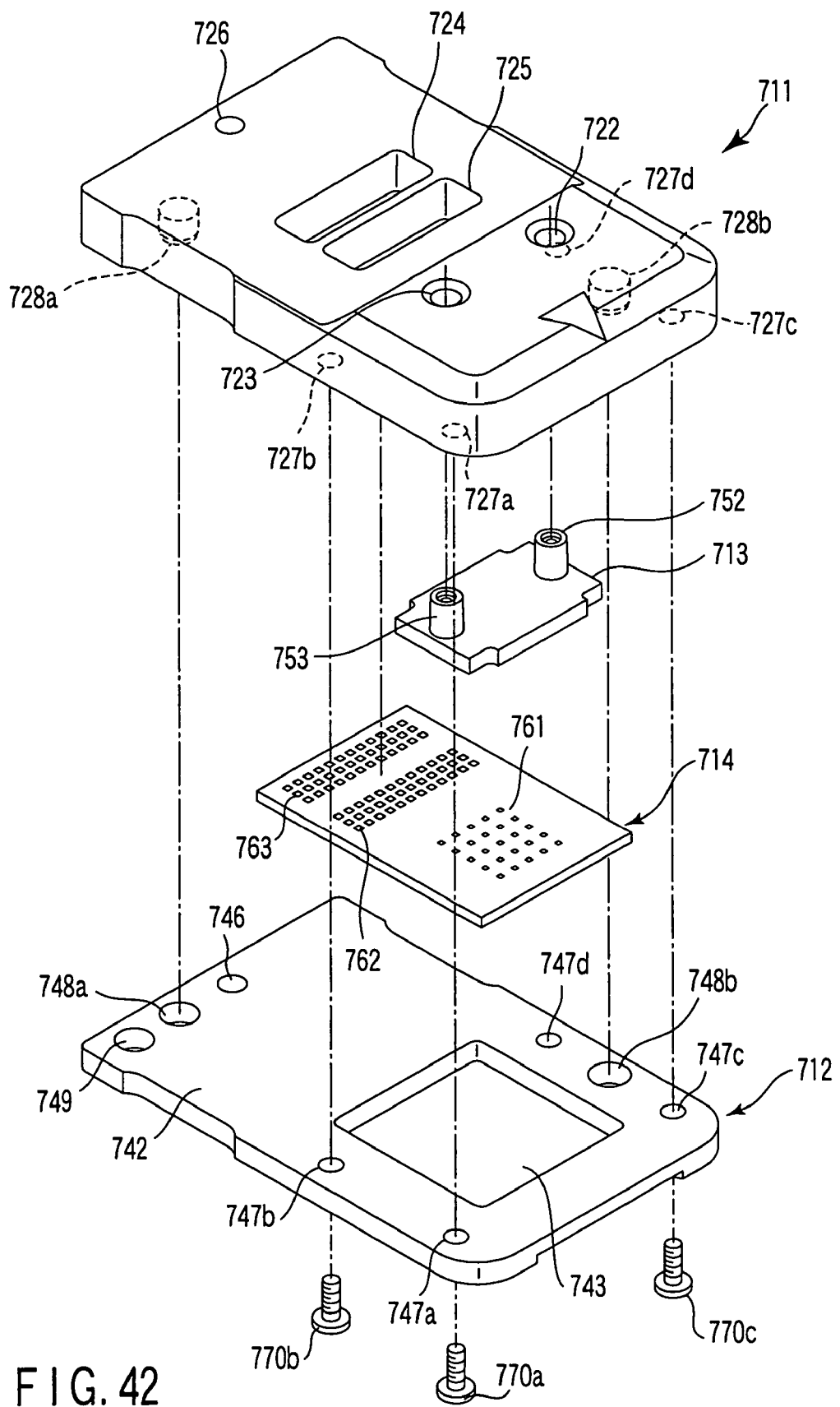
F I G. 42

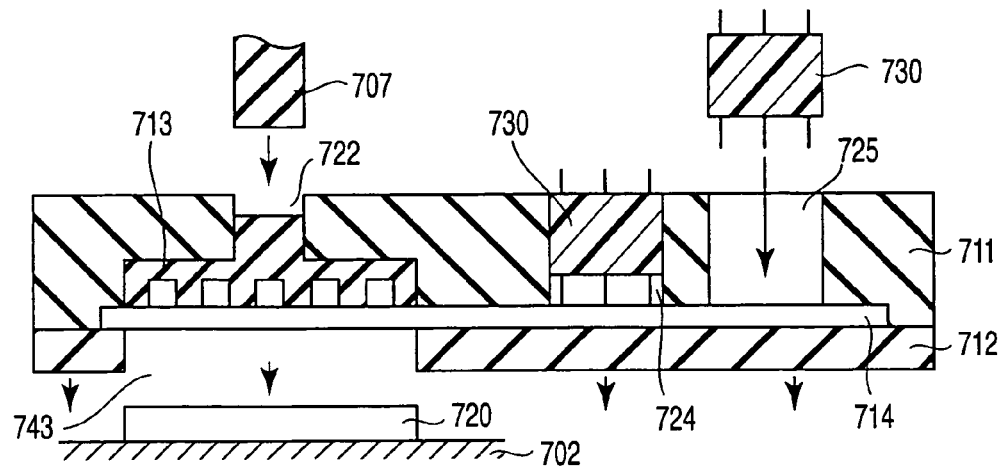
F I G. 44
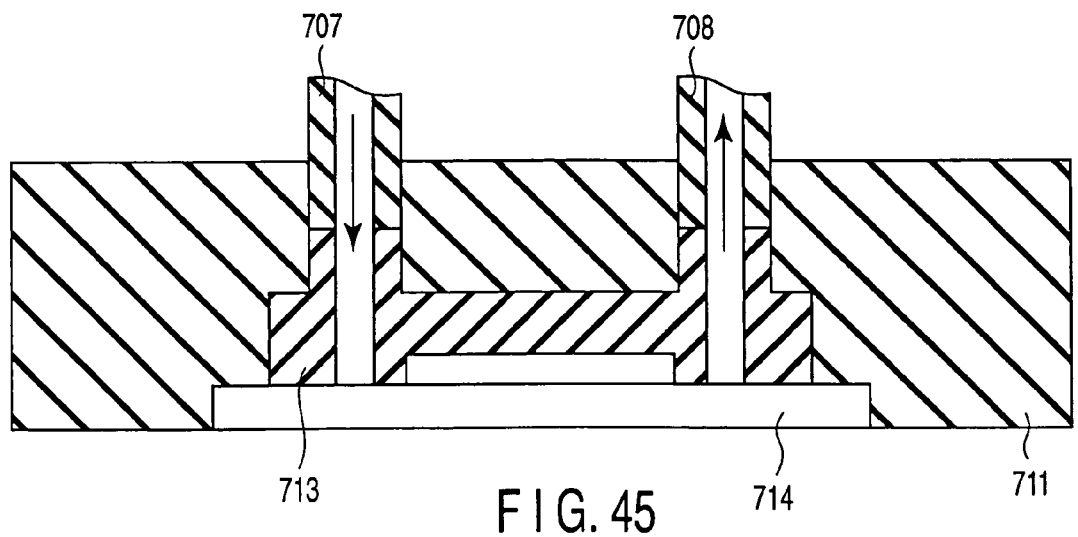
F I G. 45

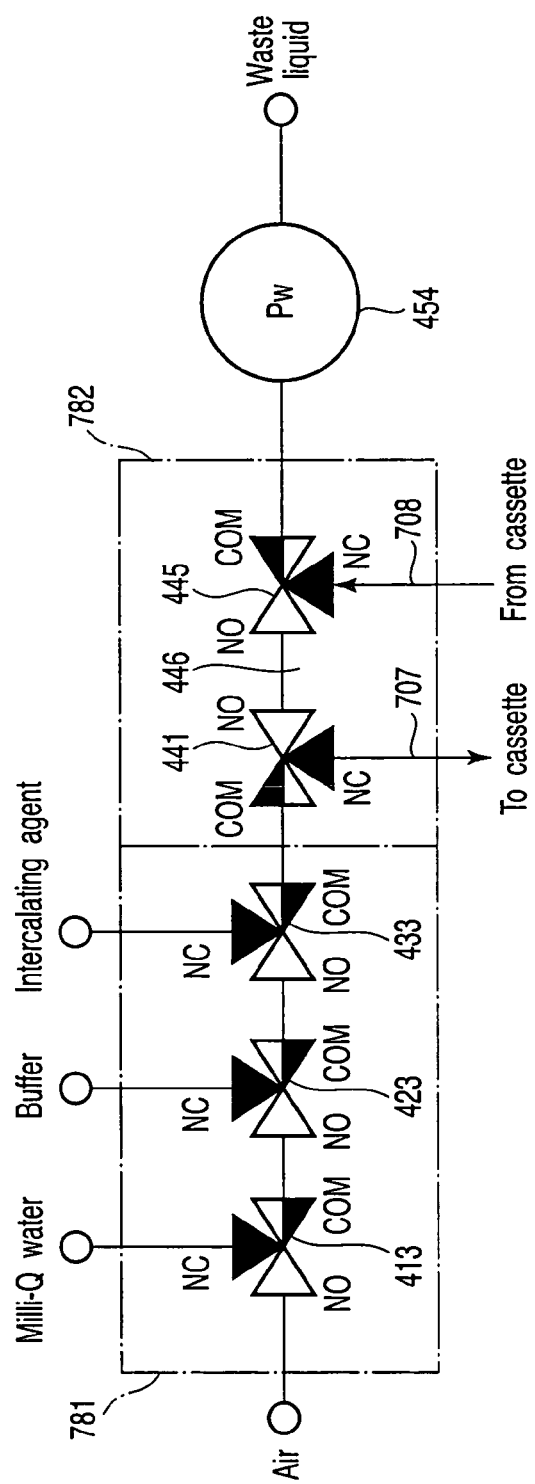
FIG. 53
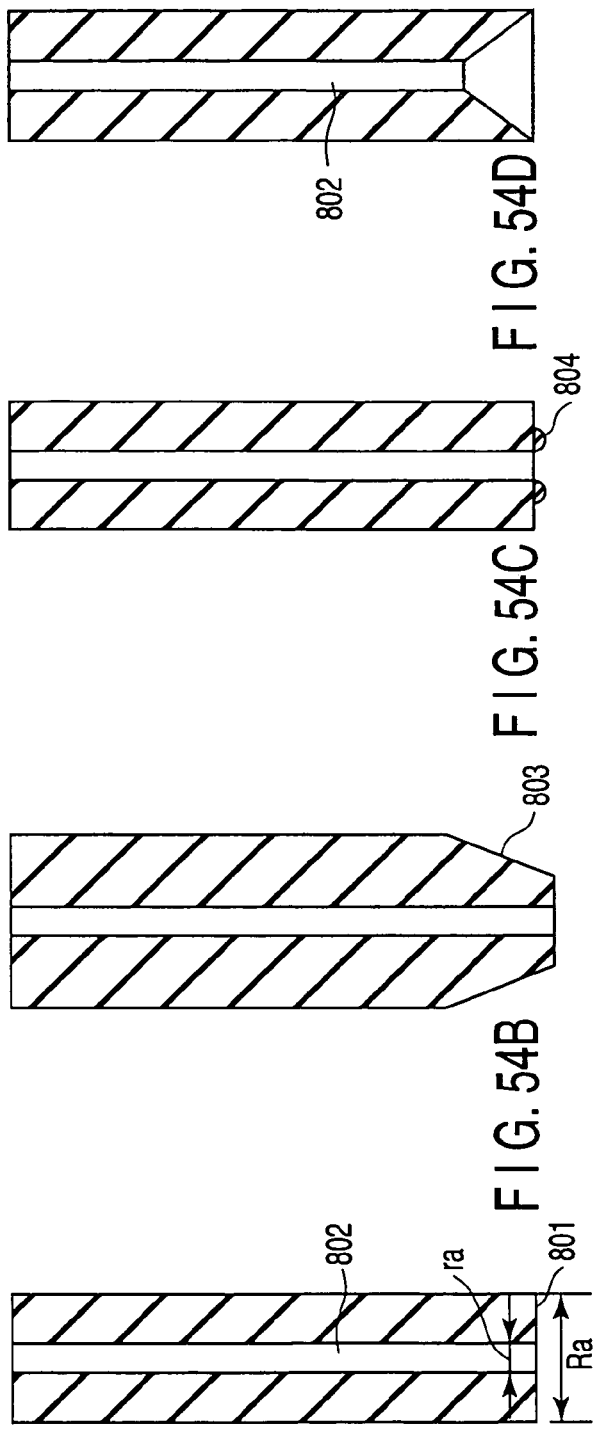
FIG. 54A
FIG. 54B
FIG. 54C
FIG. 54D

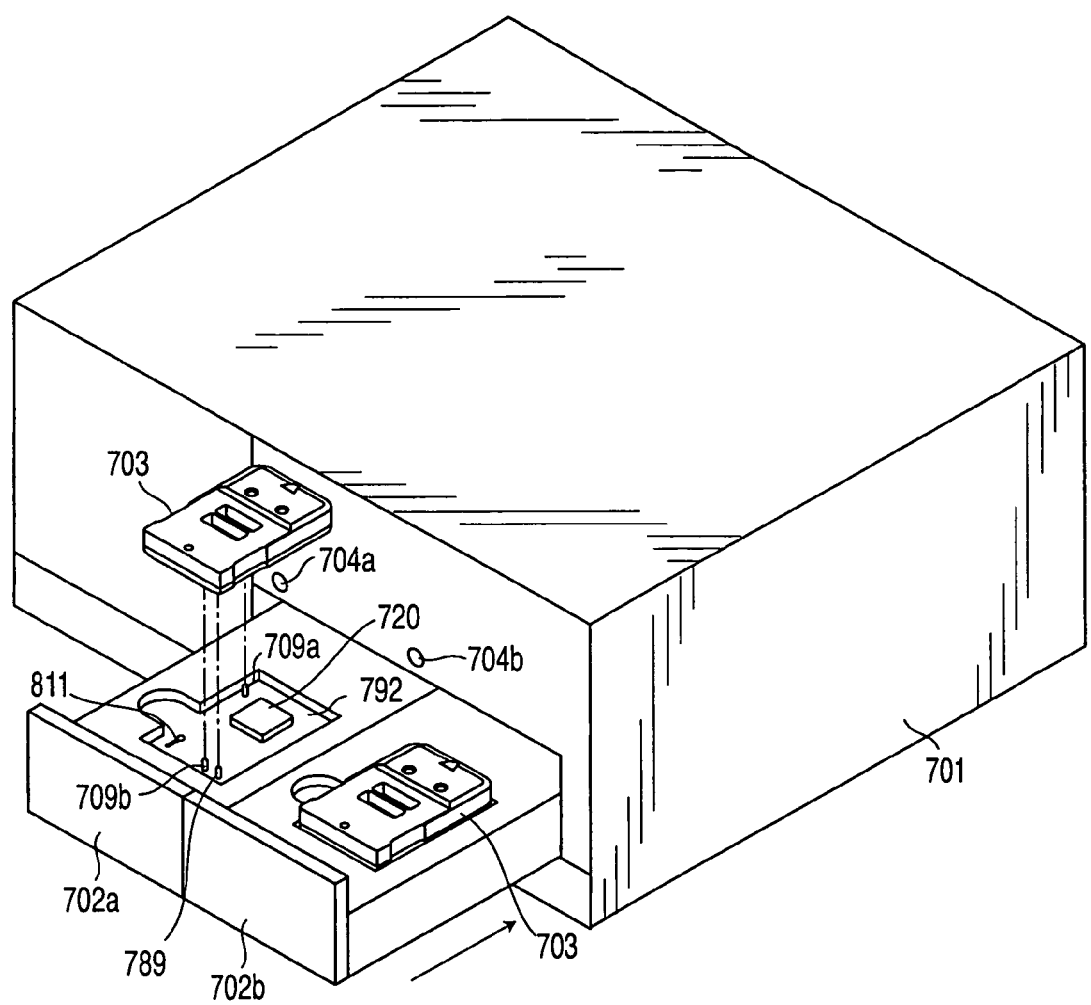
F I G. 56

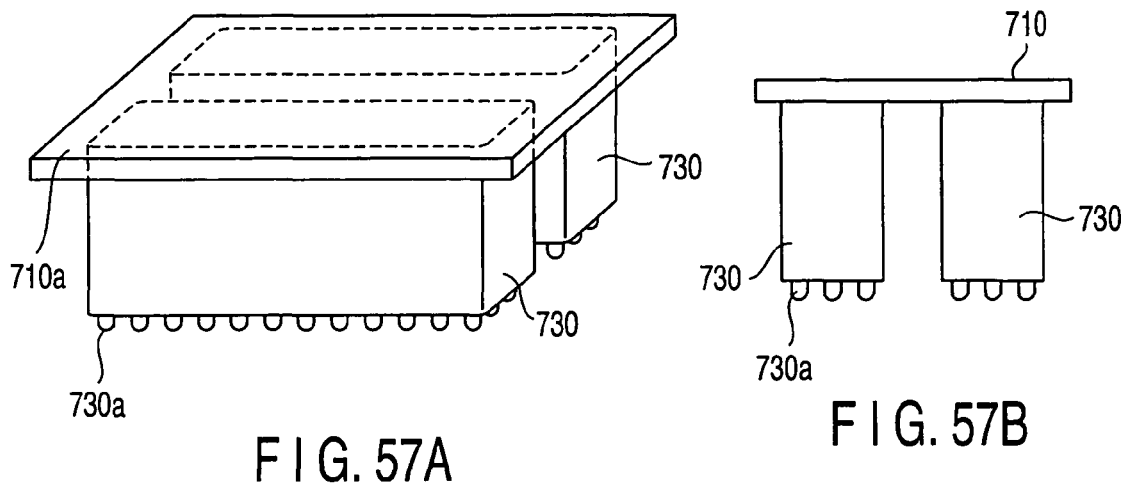
FIG. 57A
FIG. 57B
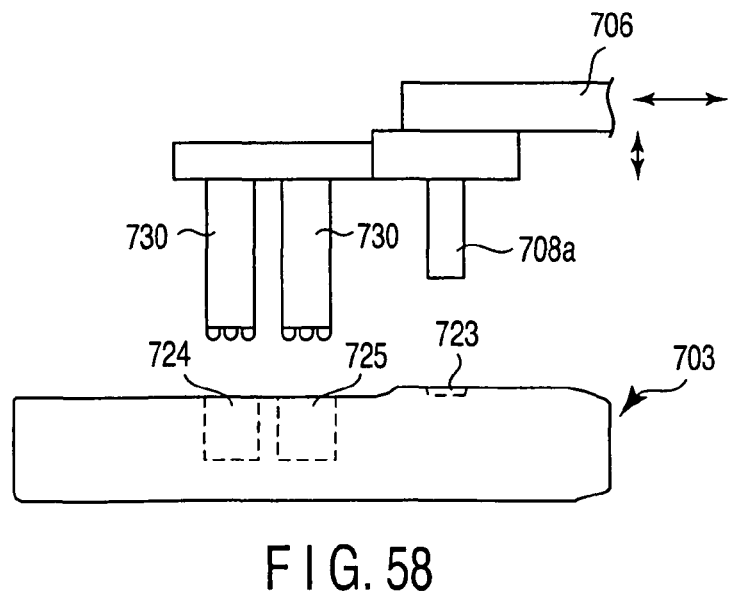
FIG. 58

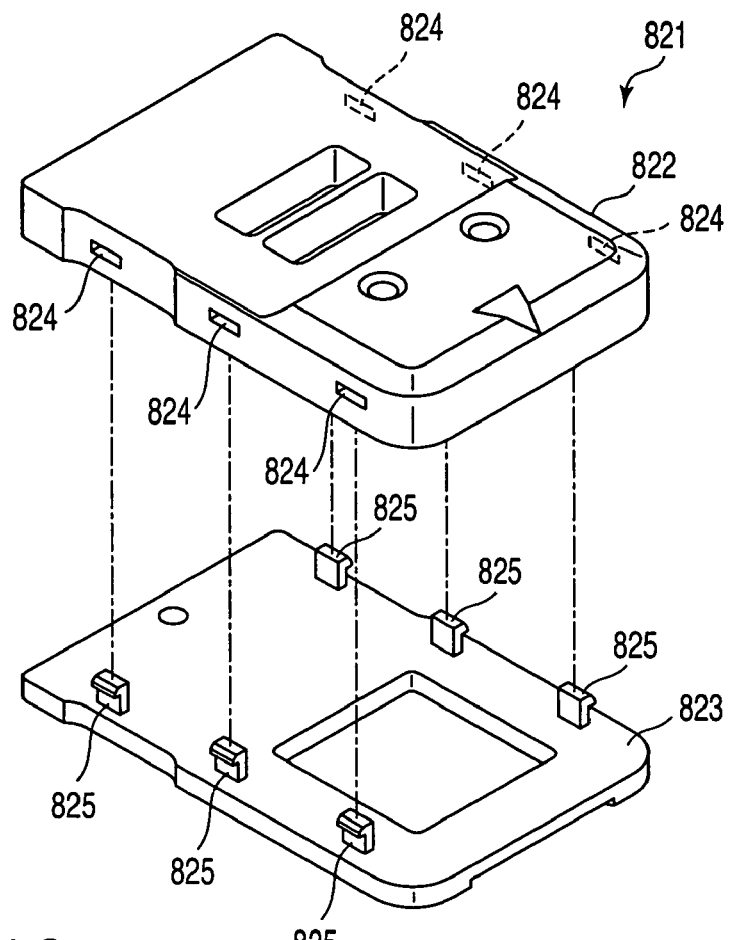
F I G. 59
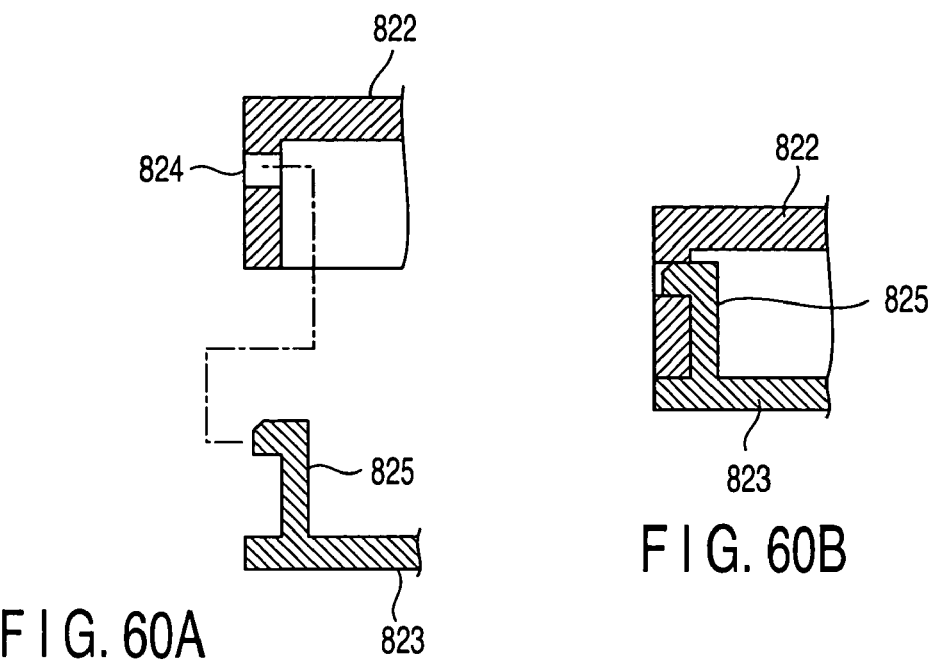
F I G. 60A
F I G. 60B

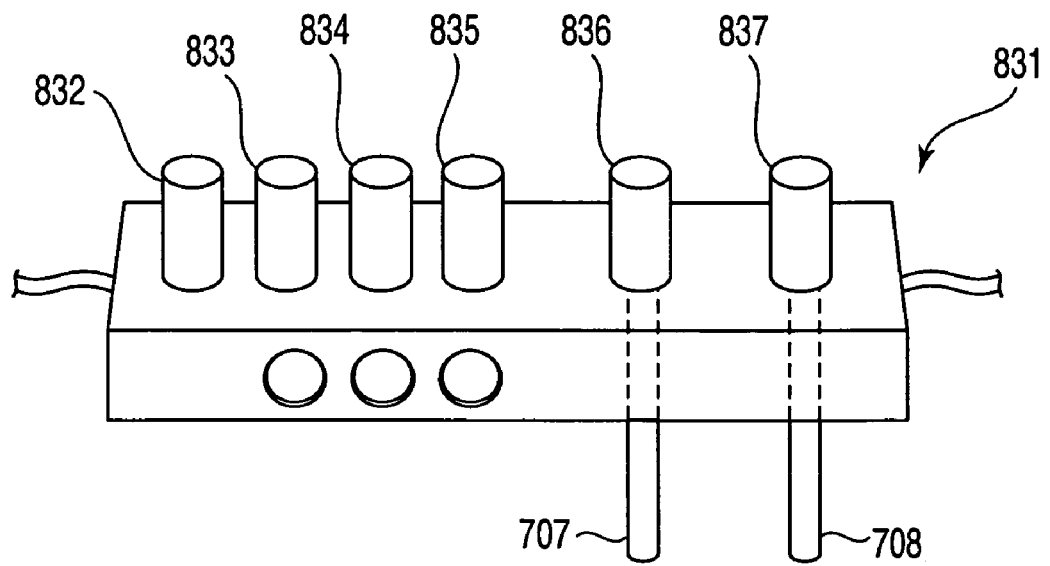
F I G. 61
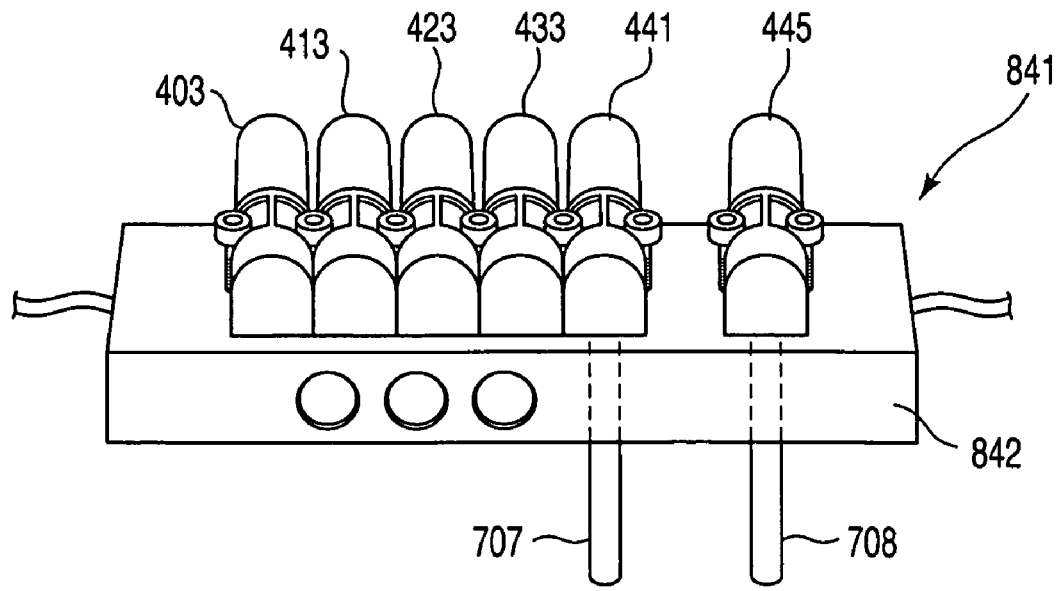
F I G. 62

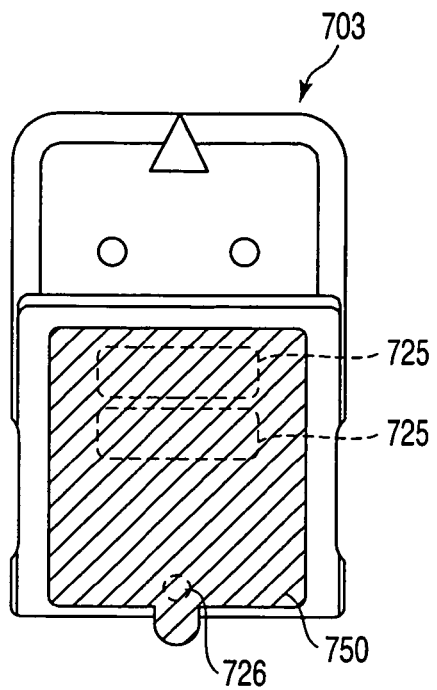
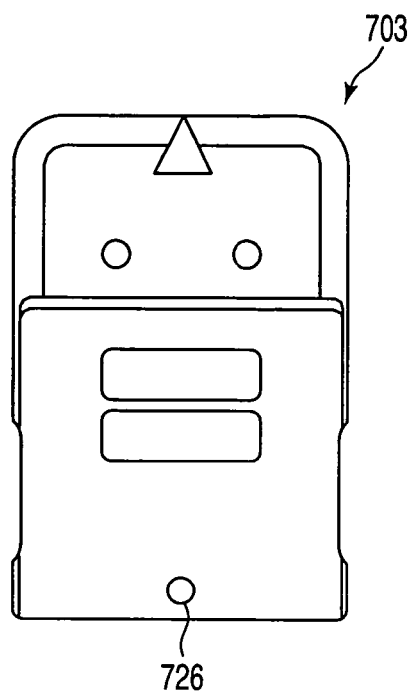
FIG. 67A  FIG. 67B
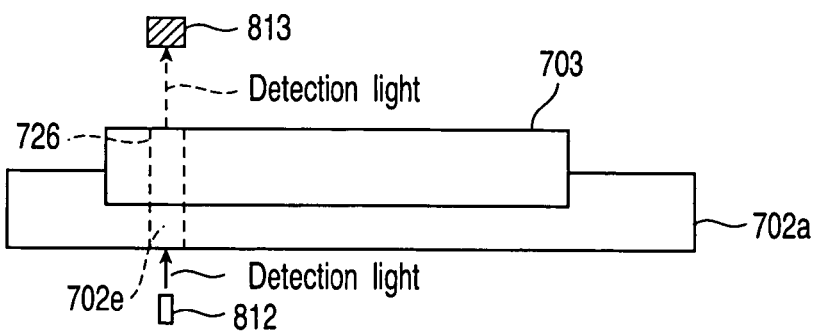
FIG. 68
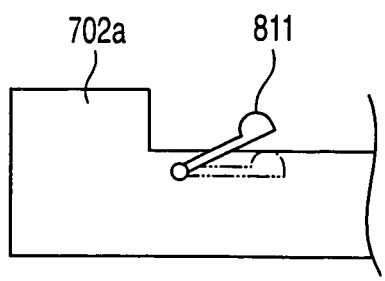
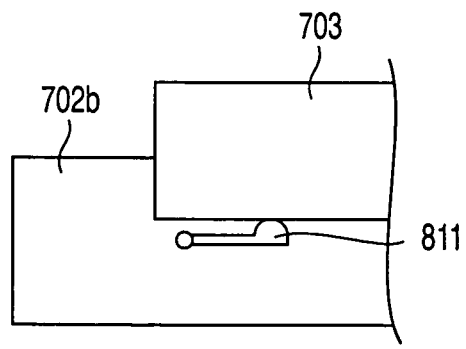
FIG. 69A  FIG. 69B

BASE SEQUENCE DETECTION APPARATUS AND BASE SEQUENCE AUTOMATIC ANALYZING APPARATUS

CROSS REFERENCE TO RELATED APPLICATIONS

This is a Continuation Application of PCT Application No. PCT/JP03/09684, filed Jul. 30, 2003, which was published under PCT Article 21(2) in Japanese.

This application is based upon and claims the benefit of priority from prior Japanese Patent Applications No. 2002-223392, filed Jul. 31, 2002; and No. 2003-200440, filed Jul. 23, 2003, the entire contents of both of which are incorporated herein by reference.

BACKGROUND OF THE INVENTION

1. Field of the Invention

The present invention relates to a base sequence detection apparatus which detects a base sequence and a base sequence automatic analyzing apparatus which automatically controls the base sequence detection apparatus and automatically analyzes a measurement signal.

2. Description of the Related Art

There conventionally exist, e.g., apparatuses which execute only hybridization, apparatuses which execute only electrochemical measurement after hybridization and addition of intercalating agents, and apparatuses which automatically execute a whole process from hybridization to cleaning using buffers (e.g., patent document 1: Jpn. Pat. Appln. KOHYO Publication No. 9-504910).

Assume that measurement is executed by using the above-described apparatuses. Every time one process is ended, the operator must manually transfer the sample to the apparatus for the next process. This imposes restrictions on time. In addition, since the operator takes a hand in transfer between processes, the data reproducibility between samples is poor.

Furthermore, measurement results may vary depending on reaction conditions in a reaction cell. When measurement is performed using a 3-electrode unit including a plurality of working electrodes, the reaction environment varies between the working electrodes, and therefore, detection results also vary.

BRIEF SUMMARY OF THE INVENTION

It is an object of the present invention to provide a base sequence detection apparatus which has a highly uniform electrochemical reaction characteristic and a high detection reliability.

It is another object of the present invention to provide a base sequence automatic analyzing apparatus which can automatically execute a whole process of reaction, solution supply, and measurement.

According to an aspect of the present invention, there is provided a base sequence detection apparatus which detects a first base sequence in a sample on the basis of a reaction between the sample in a channel and a probe including a second base sequence, comprising a substrate, a channel which is formed on the substrate along a flowing direction of a biochemical solution or air, a plurality of working electrodes which are formed on the substrate along the channel and include the probe immobilized thereon, a plurality of counter electrodes which are formed on an inner surface of the channel in correspondence with the working electrodes and located on a first surface opposing a surface of the substrate to give a potential difference with respect to the working electrodes, a plurality of reference electrodes which are formed on an inner surface of the channel in correspondence with the working electrodes and located on a second surface opposing the substrate surface to feedback a detection voltage to the working electrodes, an introduction port which is open to the channel and introduces the biochemical solution or air into an upstream side of the channel into the channel, a delivery port which is open to the channel and delivers the biochemical solution or air from a downstream side of the channel; and a sample injection port through which the sample is injected into the channel.

According to another aspect of the present invention, there is provided a base sequence detection apparatus which detects a first base sequence in a sample on the basis of a reaction between a probe including a second base sequence and the sample in a cell which is defined by a cell upper surface, cell side surfaces, and a cell bottom surface, comprising:

a base sequence detection chip which comprises a substrate and a plurality of working electrodes and defines the cell bottom surface, wherein the working electrodes are formed on the substrate along a flowing direction of a biochemical solution or air and having the probe immobilized thereon;

a chip cartridge top cover which comprises counter electrodes and reference electrodes formed along the flowing direction of the biochemical solution or air, wherein the counter electrodes are formed in correspondence with the working electrodes and located on a first surface opposing a surface of the substrate to give a potential difference with respect to the working electrodes, and the reference electrodes are formed in correspondence with the working electrodes and located on a second surface opposing the substrate surface to feedback a detection voltage to the working electrodes;

a sealing member which is sandwiched and fixed between the chip cartridge top cover and the substrate surface to form a channel including equal sections near the working electrodes, counter electrodes, and reference electrodes and defines the cell upper surface and cell side surfaces;

an introduction port which is formed in the chip cartridge top cover and introduces the biochemical solution or air into an upstream side of the flowing direction of the biochemical solution or air into the cell;

a delivery port which is formed in the chip cartridge top cover and delivers the biochemical solution or air in the cell from a downstream side of the flowing direction of the biochemical solution or air; and a sample injection port which is formed in the chip cartridge top cover and through which the sample is injected into the cell.

According to get another aspect of the present invention, there is provided a base sequence automatic analyzing apparatus comprising:

a base sequence detection apparatus described above;

a supply unit comprising a first pipe which communicates with the introduction port and supplies the biochemical solution or air into the channel through the introduction port, and a first valve which controls a flow rate of the biochemical solution or air in the first pipe;

a discharge unit comprising a second pipe which communicates with the delivery port and discharges the biochemical solution or air from the channel through the delivery port, a second valve which controls the flow rate of the biochemical solution or air in the second pipe, and a pump which is arranged on the second pipe and sucks the biochemical solution or air from the channel;

a measurement unit comprising a voltage applying unit which gives a potential difference between the working electrode and the counter electrode;

a temperature controller which controls a temperature of the base sequence detection chip;

a control mechanism which controls the first valves of the supply unit, the second valve and pump of the discharge unit, the voltage applying unit of the measurement unit, and the temperature controller, detects an electrochemical reaction signal from the working electrode or counter electrode, and stores the electrochemical reaction signal as measurement data; and a computer which gives control condition parameters to the control mechanism to control the control mechanism and executes analysis processing of the first base sequence on the basis of the measurement data.

According to further aspect of the present invention, there is provided a base sequence automatic analyzing apparatus which automatically analyzes a first base sequence in a sample on the basis of a reaction between the sample in a channel and a probe including a second base sequence, comprising:

a cassette including a substrate including a major surface and pads on the major surface, a sealing member comprising a sealing member main body which comprises a major surface and a flat lower surface that is arranged in contact with the major surface of the substrate and includes a plurality of working electrodes that are formed on the major surface along the channel wherein the probe is immobilized thereon, reference electrodes and counter electrodes, a groove portion which is formed in the lower surface and forms a gap with respect to the working electrodes to form the channel, a first port which communicates with one end of the channel and is open to the major surface at a first position separated from the major surface of the substrate, and a second port which communicates with the other end of the channel and is open to the major surface at a second position separated from the major surface of the substrate, and a cassette main body which brings the lower surface of the sealing member main body into contact with the major surface of the substrate and fixes the sealing member main body;

a valve unit including a first valve which switches between a biochemical solution and air supplied from the first port, a second valve which switches between the biochemical solution and air discharged from the second port, a first nozzle connected to the first valve, and a second nozzle connected to the second valve wherein the first and second valves and the first and second nozzles are integrally formed;

a probe unit which is fixed to the valve unit and includes an electric connector;

a driving unit which drives the valve unit or the cassette to position the first nozzle to the first port and communicate the first nozzle with the first port, position the second nozzle to the second port and communicate the second nozzle with the second port, and position the electric connector of the probe unit to the pads on the substrate and connect the pads to the electric connector electrically;

a measurement mechanism which inputs a measurement signal to the substrate and acquires an electrical signal from the substrate; and a computer which analyzes the electrical signal obtained from the measurement mechanism.

The present invention related to the apparatus is also effective as the invention of the method realized by the apparatus.

The present invention related to the apparatus or method is also effective as a program which causes a computer to execute procedures for controlling the apparatus and a computer-readable recording medium which records the program.

BRIEF DESCRIPTION OF THE SEVERAL VIEWS OF THE DRAWING

FIG. 1 is a block diagram showing the overall arrangement of a base sequence detection apparatus according to the first embodiment of the present invention;

FIGS. 2A to 2D are views showing details of the structure of a chip cartridge according to the first embodiment;

FIG. 3 is a view showing a support body and a chip cartridge top cover before they are fixed by a top cover fixing screw according to the first embodiment;

FIGS. 7A and 7B are views showing a more detailed structure of constituent elements near the cell according to the first embodiment;

FIG. 10 is a sectional view of a modification of the shape of the cell according to the first embodiment;

FIG. 11 is a sectional view of another modification of the shape of the cell according to the first embodiment;

FIGS. 15A to 15D are sectional views showing steps in manufacturing the base sequence detection chip and printed board according to the first embodiment;

FIGS. 21A to 21E are timing charts showing voltage characteristics according to the first embodiment;

FIGS. 22A to 22D are timing charts showing the voltage characteristics of the conventional potentiostat;

FIG. 26 is a view showing still another modification of the potentiostat according to the first embodiment;

FIG. 28 is a block diagram showing the association between the control mechanism and the remaining constituent elements of a computer according to the first embodiment;

FIG. 42 is a view showing the assembled state of the cassette according to the second embodiment;

FIG. 44 is a sectional view of a cassette side surface according to the second embodiment;

FIG. 45 is a view showing details of a channel according to the second embodiment;

FIG. 53 is a view showing the functional arrangement of the valve unit according to the second embodiment;

FIGS. 54A to 54D are views showing the detailed structures of nozzle tip shapes according to the second embodiment;

FIG. 56 is a view showing an example of the arrangement of the base sequence automatic analyzing apparatus according to the second embodiment in a cassette loading operation;

FIGS. 57A and 57B are views showing the detailed structure of a probe unit according to the second embodiment;

FIG. 58 is a view showing the detailed structures of the probe unit and valve unit according to the second embodiment;

FIG. 59 is a view showing a modification of the cassette according to the second embodiment;

FIGS. 60A and 60B are views for explaining a cassette fixing method in the modification of the cassette according to the second embodiment;

FIG. 61 is a view showing another example of the valve unit according to the second embodiment;

FIG. 62 is a view showing still another example of the valve unit according to the second embodiment;

FIGS. 67A and 67B are views showing examples of the cassette with and without a seal according to the second embodiment;

FIG. 68 is a view for explaining a seal detection operation according to the second embodiment;

FIGS. 69A and 69B are views for explaining a cassette detection operation according to the second embodiment;

DETAILED DESCRIPTION OF THE INVENTION

Figure 4:
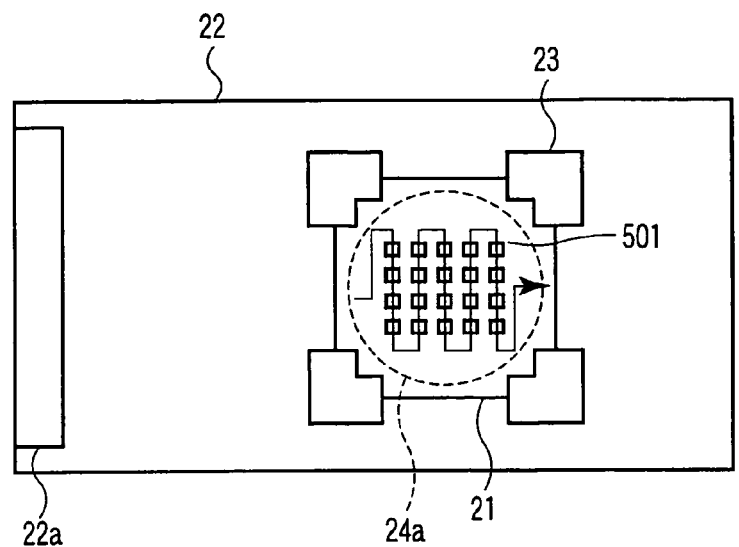
FIG. 4 is a view showing the detailed structure of a printed board on which a base sequence detection chip according to the first embodiment is mounted.

The embodiments of the present invention will be described below with reference to the accompanying drawings.

First Embodiment

FIG. 1 is a block diagram showing the overall arrangement of a base sequence automatic analyzing apparatus according to the first embodiment of the present invention. As shown in FIG. 1, a base sequence automatic analyzing apparatus 1 includes a chip cartridge 11 (base sequence detection apparatus), a measurement system 12, a solution supply system 13, and a temperature control mechanism 14. The chip cartridge 11 and measurement system 12 are electrically connected. The solution supply system 13 is physically connected to a channel provided in the chip cartridge 11 through an interface section. The temperature control mechanism 14 controls the temperature of the chip cartridge 11.

The measurement system 12, solution supply system 13, and temperature control mechanism 14 are controlled by a control mechanism 15. The control mechanism 15 is electrically connected to a computer 16. The control mechanism 15 is controlled in accordance with a program installed in the computer 16. In this embodiment, the chip cartridge 11, measurement system 12, solution supply system 13, and temperature control mechanism 14 will be referred to as a measurement unit 10.

The chip cartridge 11 is used with a printed board 22 attached thereto. A base sequence detection chip 21 on which DNA probes are immobilized is mounted on the printed board 22.

In the following embodiments, a DNA base sequence to be detected will be referred to as a target base sequence. A base sequence which is complementary to the target base sequence and selectively reacts with the target base sequence will be referred to as a target complementary base sequence. A DNA probe containing the target complementary base sequence is immobilized to the working electrodes of the base sequence detection chip 21. A sample (specimen solution) supplied into the cell of the base sequence detection chip 21 contains DNA to be analyzed. The base sequence of the DNA to be analyzed will be referred to as a specimen base sequence.

The base sequence detection apparatus according to this embodiment hybridizes the specimen base sequence and target complementary base sequence. After a buffer and an intercalating agent are introduced, the presence/absence of a hybridization reaction is monitored. Accordingly, it can be determined whether the target base sequence is contained in the sample.

FIGS. 2A to 2D are views showing the detailed structure of the chip cartridge 11. FIG. 2A is a plan view. FIG. 2B is a view taken along a direction A-A. FIG. 2C is a partially perspective sectional view taken along a direction B-B. FIG. 2D is a view of a support body 111 as one constituent component of the chip cartridge 11, which is viewed from the lower surface side.

A chip cartridge main body 110 comprises the support body 111 and a chip cartridge top cover 112. The support body 111 supports the printed board 22 from the lower side. The chip cartridge top cover 112 sandwiches the printed board 22 from the upper side with the support body 111 and fixes and supports the printed board 22.

The chip cartridge top cover 112 has two openings on a side portion. An interface section 113a is connected to one of the openings. An interface section 113b is connected to the other opening. The interface sections 113a and 113b function as the interfaces between the solution supply system 13 and the chip cartridge 11.

The interface sections 113a and 113b have channels 114a and 114b, respectively, inside. A biochemical solution or air from the upstream side of the solution supply system 13 is introduced into the chip cartridge 11 through the channel 114a. A sample, biochemical solution, or air in the chip cartridge 11 is delivered to the downstream side of the solution supply system 13 through the channel 114b.

Referring to FIGS. 2A to 2C, the channels 114a and 114b are indicated by broken lines. The channels 114a and 114b communicate with the interior of the chip cartridge top cover 112 through the interface sections 113a and 113b and then communicate with a cell 115. The cell 115 is a region that is prepared to cause an electrochemical reaction between the base sequence detection chip 21 and various solutions introduced into the base sequence detection chip 21. When the four corners of the printed board 22 having the base sequence detection chip 21 mounted thereon are fixed to the chip cartridge top cover 112 of the chip cartridge 11 by board fixing screws 25, the cell 115 is defined as an enclosed spatial region surrounded by the base sequence detection chip 21, a sealing member 24a, and the chip cartridge top cover 112. The printed board 22 having the base sequence detection chip 21 mounted thereon is fixed to the chip cartridge top cover 112. In this state, the printed board 22 is sandwiched and held by the support body 111 and chip cartridge top cover 112 via the sealing member 24a. In addition, the chip cartridge top cover 112 is fixed by a top cover fixing screw 117. Accordingly, the injection/discharge path of various biochemical solutions or air is defined such that it communicates from the channel 114a to the channel 114b through the cell 115. The base sequence detection chip 21 is encapsulated to the printed board 22 by an encapsulating resin 23.

The chip cartridge top cover 112 located on the cell 115 has an introduction port 116a and a delivery port 116b. The introduction port 116a extends from a side surface to the bottom surface of the chip cartridge top cover 112. The introduction port 116a is open to the bottom surface of the chip cartridge top cover 112 at a cell hole portion 115a. The delivery port 116b extends from another side surface to the bottom surface of the chip cartridge top cover 112. The delivery port 116b is open to the bottom surface of the chip cartridge top cover 112 at a cell hole portion 115b. The introduction port 116a is connected to the channel 114a. The delivery port 116b is connected to the channel 114b. With this structure, the channel 114a and cell 115 communicate with each other while the channel 114b and cell 115 communicate with each other.

An electrical connector 22a is set on the surface printed board 22 at a position separated from the cell 115. The electrical connector 22a is electrically connected to the lead frame of the board main body of the printed board 22. The lead frame of the board main body is electrically connected to various kinds of electrodes of the base sequence detection chip 21 through leads or the like. The terminal of the measurement system 12 is connected to the electrical connector 22a. Accordingly, an electrical signal obtained by the base sequence detection chip 21 can be output to the measurement system 12 through a predetermined terminal provided at a predetermined position of the printed board 22 and also through the electrical connector 22a.

As shown in FIG. 2D, the support body 111 has a U shape. A cut portion 111a is formed at the center of the support body 111. The cut portion 111a is smaller than the printed board 22 and larger than the base sequence detection chip 21. Accordingly, the temperature control mechanism 14 can be arranged in contact with the base sequence detection chip 21 without intervening the support body 111 while maintaining the support function of the printed board 22 by the support body 111. Reference numeral 117a denotes a threaded hole in which the top cover fixing screw 117 is fixed.

As the temperature control mechanism 14 which adjusts the temperature of the base sequence detection chip 21, for example, a Peltier element is used. This enables temperature control within the range of ±0.5° C. The DNA reaction is generally caused in a temperature range relatively close to the room temperature. Hence, if the temperature is controlled using only a heater, the stability is poor. In addition, since the DNA reaction must be controlled in accordance with a temperature control, an independent cooling mechanism is necessary. However, a Peltier element is optimum because it can execute both heating and cooling by changing the direction of a current.

FIG. 3 is a view showing the support body 111 and chip cartridge top cover 112 before they are fixed by the top cover fixing screw 117. As shown in FIG. 3, the four corners of the printed board 22 having the base sequence detection chip 21 mounted thereon are fixed to the chip cartridge top cover 112 by the board fixing screws 25. The sealing member 24a is integrated with the chip cartridge top cover 112. Hence, the cell 115 surrounded by the sealing member 24a and chip cartridge top cover 112 is defined on the base sequence detection chip 21. In addition, the chip cartridge top cover 112 is fixed to the support body 111 by the top cover fixing screw 117. The board fixing screws 25 may be fixed either from the lower surface side of the printed board 22 or from the upper surface side. When the printed board 22 is fixed to the chip cartridge top cover 112 in this way, the contact between the base sequence detection chip 21, the sealing member 24a, and the chip cartridge top cover 112 can be reliably held.

FIG. 4 is a view showing the detailed structure of the printed board 22 on which the base sequence detection chip 21 is mounted. As shown in FIG. 4, the base sequence detection chip 21 is encapsulated by the encapsulating resin 23. Working electrodes 501 are formed on the base sequence detection chip 21. The working electrodes 501 are arranged one by one along the flowing direction of a biochemical solution and air indicated by the arrow in FIG. 4. The flowing direction of a biochemical solution and air is defined by enclosing a space along the direction indicated by the arrow around the working electrodes 501 on the base sequence detection chip 21 by the chip cartridge top cover 112 and sealing member 24a. The region indicated by the broken line is the region where the sealing member 24a is arranged. The plurality of working electrodes 501 are arranged within the region indicated by the broken line.

The electrical connector 22a is arranged at an end portion of the printed board 22. The working electrodes 501 of the base sequence detection chip 21 and the electrical connector 22a are electrically connected by a lead frame provided on the surface of the printed board 22. When the signal interface of the measurement system 12 is connected to the electrical connector 22a, each electrode of the base sequence detection chip 21 and the measurement system 12 can be electrically connected.

Figure 5A:
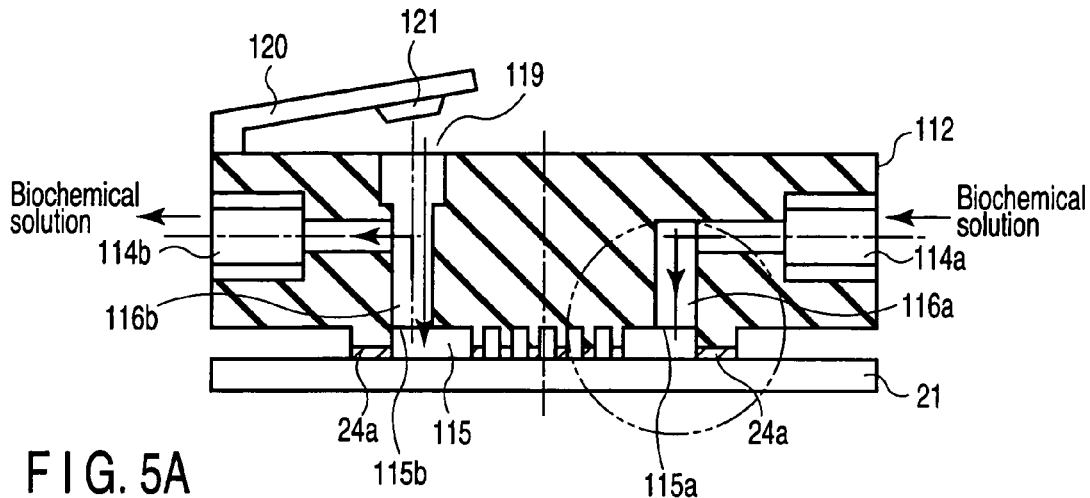
FIGS. 5A to 5C are views showing a cell and a biochemical solution supply system which communicates with the cell according to the first embodiment.
Figure 5B:
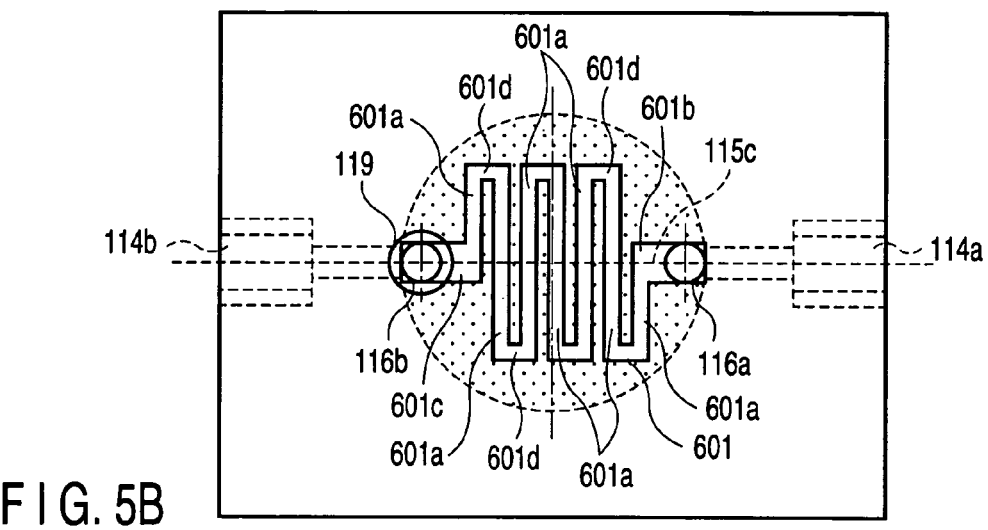

FIG. 5A is a sectional view showing the cell 115 shown in FIG. 2A and a biochemical solution supply system which communicates with the cell 115, which are viewed from a direction C-C. FIG. 5B is a plan view of a portion near the cell 115.

As shown in FIG. 5A, a channel-shaped projecting portion 112a having a height $d_{42}$ is formed on the bottom surface of the chip cartridge top cover 112. The sealing member 24a is printed in advance on the channel-shaped projecting portion 112a by, e.g., screen printing so that the channel-shaped projecting portion 112a is integrated with the sealing member 24a. Accordingly, the position of the cell 115 can be defined without aligning the sealing member 24a and chip cartridge top cover 112. The assembly step of the cell 115 is simplified. The sealing member 24a is fixed between the channel-shaped projecting portion 112a and the base sequence detection chip 21. With this structure, a closed space is defined between the chip cartridge top cover 112 and the base sequence detection chip 21. This closed space is the cell 115 serving as a reaction chamber where an electrochemical reaction occurs between a probe and a sample or biochemical solution. The bottom surface of the cell 115 is defined by the base sequence detection chip 21. The side surfaces of the cell 115 are defined by the side portions of the channel-shaped projecting portion 112a and sealing member 24a arranged on the chip cartridge 112. The upper surface of the cell 115 is defined by a portion of the chip cartridge 112, where the channel-shaped projecting portion 112a is not formed. With this structure, a closed space which is enclosed except the cell hole portions 115a and 115b is defined. The liquid-tightness between the base sequence detection chip 21 and a cover 120 is held. The height of the cell 115 is set to about 0.5 mm. In this example, the height is set to about 0.5 mm. However, the present invention is not limited to this. The height is preferably set within the range of 0.1 mm to 3 mm.

The cell 115 has a shape with a long channel 601, as shown in FIG. 5B, when viewed from the upper side. Referring to FIG. 5B, there is provided one channel 601 which has the same path width from the cell hole portion 115a on the side of the introduction port 116a to the cell hole portion 115b. The channel 601 comprises detection channels 601a, port connection channels 601b and 601c, and channel connection channels 601d.

The detection channels 601a comprise a plurality of channels in which the working electrodes 501 are arranged. The port connection channel 601b connects the detection channel 601a closest to the cell hole portion 115a to the cell hole portion 115a. The port connection channel 601c connects the detection channel 601a closest to the cell hole portion 115b to the cell hole portion 15b. The channel connection channels 601d connect the end portions of the detection channels 601a adjacent to each other to define the flowing direction of a biochemical solution or air through the plurality of detection channels 601a to one direction. Accordingly, a biochemical solution or air that flows to a given detection channel 601a flows into the channel connection channel 601d and then flows into another detection channel 601a adjacent in the same direction. All the channels 601a to 601d have the same path width and section. The path width is preferably 0.5 mm to 10 mm.

Referring to FIG. 5B, the region indicated by the broken line and having no channel 601 is the region where the channel-shaped projecting portion 112a and sealing member 24a are arranged so that the base sequence detection chip 21 and sealing member 24a come into contact. The region having the channel 601 is the region where the channel-shaped projecting portion 112a and sealing member 24a are not arranged.

The introduction port 116a and delivery port 116b extend upward from the upper surface of the cell 115 to predetermined heights in a direction almost perpendicular to the cell bottom surface. The channels of the introduction port 116a and delivery port 116b deflect in directions to separate from each other from the center of the cell 115 and are connected to the channels 114a and 114b, respectively.

The delivery port 116b extends to a predetermined height in a direction almost perpendicular to the cell bottom surface. The delivery port 116b also deflects in a direction to separate from the center of the cell 115. The delivery port 116b is branched into two paths at the deflecting position. One path extends through up to the upper surface of the chip cartridge top cover 112 and communicates with a sample injection port 119. With this structure, a sample injected from the sample injection port 119 is introduced to the cell 115 through the delivery port 116b. The central axes of the sample injection port 119 and delivery port 116b almost coincide with each other. The diameter of the sample injection port 119 is set to be larger than that of the solution supply port 116b. In addition, the sample injection port 119 can be closed by the cover 120 arranged near the sample injection port 119. When a biochemical solution is circulated from the channel 114a to the channel 114b through the cell 115 without using the sample injection port 119, the cover 120 prevents the biochemical solution from flowing out from the sample injection port 119. Hence, the path of the biochemical solution can be ensured. The cover 120 has a sealing member 121. When the sealing member 121 closes the sample injection port 119, even a slight leakage of the biochemical solution can be prevented. Although not particularly illustrated in the example shown in FIG. 5A, the sealing member 121 may deeply enter the path to the sample injection port 119 and completely close that path except the path that connects the delivery port 116*b* to the channel 114*b*. In this case, retention of a biochemical solution or air on the side of the sample injection port 119 can be reduced.

With the above structure, a biochemical solution can flow in a direction indicated by arrows in FIG. 5A sequentially through the channel 114*a*, introduction port 116*a*, cell 115 (channel 601), delivery port 116*b*, and channel 114*b*. A sample is injected from the sample injection port 119 and introduced into the cell 115 through the delivery port 116*b* in a direction indicated by an arrow. Hence, the sample is injected from the delivery side. The biochemical solution supply flow and the sample injection path are set in reverse directions. With this structure, the sample cleaning efficiency in a cleaning process can be increased.

Figure 5C:
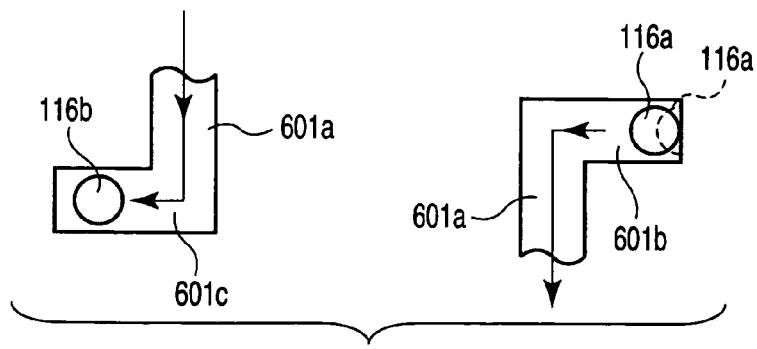

FIG. 5C is a view showing the optimum positional relationship between the introduction port 116*a*, the delivery port 116*b*, and the channel 601. The outer edge of the introduction port 116*a* is in contact with that of the port connection channel 601*b*. The outer edge of the delivery port 116*b* is separated from that of the port connection channel 601*c*. With this structure, the residue of a biochemical solution or air that readily remains near the port corner of the introduction port 116*a* in introducing the biochemical solution or air can be reduced. In addition, a variation in solution supply speed, which is caused at the port corner of the delivery port 116*b* in delivering the biochemical solution or air can be reduced. Furthermore, residual air can be reduced.

As indicated by the broken line in FIG. 5C, the outer edge of the introduction port 116*a* may overlap the outer edge of the port connection channel 601*b*. In this case, the introduction port 116*a* projects from the port connection channel 601*b*, and the same effect as described above can be obtained. The positional relationship between introduction port 116*a*, the delivery port 116*b*, and the channel 601 is not limited to that shown in FIG. 5C, as a matter of course. Three connection forms are available as for the port connection channel 601*b* on the side of the introduction port 116*a*: the outer edges overlap or are separated. Three connection forms are available as for the port connection channel 601*c* on the side of the delivery port 116*b*: the outer edges are in contact, overlap, or are separated.

Figures 6A, 6B:
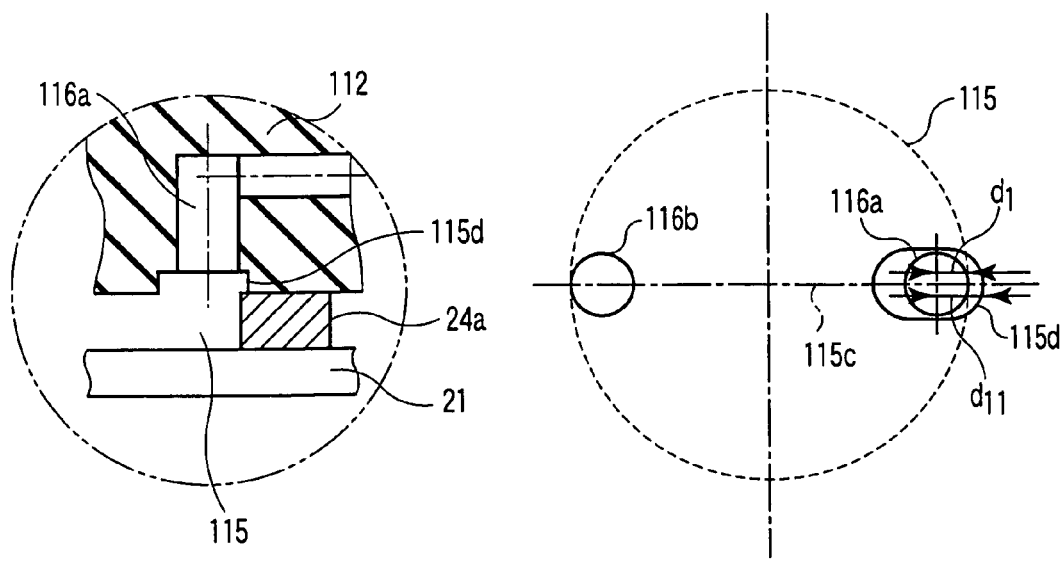
FIGS. 6A and 6B are views showing a modification of the cell according to the first embodiment.

FIG. 6A shows a modification of the part indicated by the broken line in FIG. 5A. FIG. 6B is a view showing the cell 115 in FIG. 6A when viewed from the upper side. As shown in FIG. 6A, the introduction port 116*a* has a spot facing hole 115*d*. That is, the diameter of the introduction port 116*a* becomes large stepwise toward the spot facing hole 115*d*. The diameter of the introduction port 116*a* at a position separated from the opening is smaller than the diameter of the spot facing hole 115*d*. FIG. 6B shows the positional relationship between them when viewed from the upper side. The spot facing hole 115*d* has a diameter $d_{11}$ larger than a diameter $d_1$ of the introduction port 116*a*. The outer edge of the introduction port 116*a* almost coincides with the inner wall of the channel 601. Hence, part of the outer edge of the spot facing hole 115*d* projects from the region of the cell 115. The outer edge of the spot facing hole 115*d* need not have a circular shape. For example, as shown in FIG. 6B, the hole width in a direction parallel to a line 115*c* may be set to be smaller than the hole width in a direction perpendicular to the line 115*c*.

FIGS. 6A and 6B show a case wherein the spot facing hole 115*d* is formed at the introduction port 116*a*. However, a similar spot facing hole may also be formed at the delivery port 116*b*.

As described above, when the spot facing hole 115*d* is formed at the opening of the cell 115, the inlet to the cell 115 has a funnel shape. This provides an effect that a biochemical solution or bubbles can easily be drawn and hardly remain in the cell 115.

Figure 8:
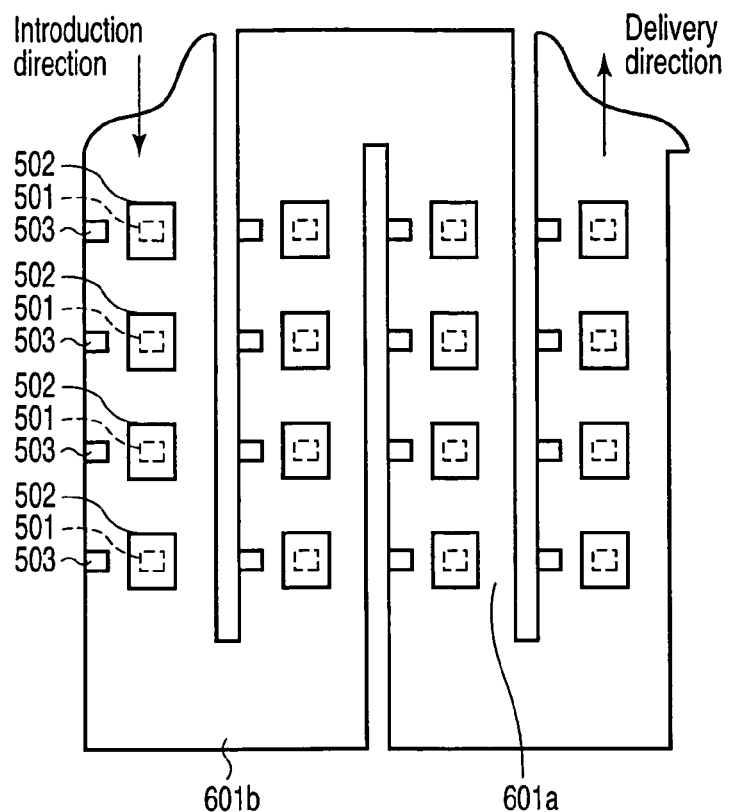
FIG. 8 is a plan view of the cell according to the first embodiment.

FIGS. 7A, 7B and 8 are views showing the detailed structure of the cell 115. FIG. 7A is a sectional view taken along a line that connects the cell hole portions 115*a* and 115*b*. FIG. 7B is a view showing a situation wherein the chip cartridge top cover 112 is being fixed to the base sequence detection chip 21. FIG. 8 is the plan view of the cell 115.

As shown in FIG. 7A, the plurality of detection channels 601*a* are formed at almost equal intervals. When a biochemical solution or air flows from the inside toward this side of the paper through the section of the detection channel 601*a* on the left side of FIG. 7A, the biochemical solution or air flows in a reverse direction, i.e., away from this side toward the inside of the paper through the detection channel 601*a* at the center. The biochemical solution or air flows again in a reverse direction, i.e., from the inside toward this side of the paper through the detection channel 601*a* on the left side. As described above, the flowing direction of a biochemical solution or air in the adjacent detection channel 601*a* is reversed.

When the detection channels 601*a* are cut along a section perpendicular to the flowing direction of a biochemical solution or air, all the detection channels 601*a* have the same rectangular sectional shape. The electrode layouts are also the same.

The bottom surface of each detection channel 601*a* is defined by the base sequence detection chip 21. One working electrode 501 is formed on the bottom surface of each detection channel 601*a*.

The side surfaces of each detection channel 601*a* are defined by the channel-shaped projecting portion 112*a* projecting from the chip cartridge top cover 112 and the sealing member 24*a*. A reference electrode 503 is fixed on each channel side surface, i.e., on a side portion of the channel-shaped projecting portion 112*a* at a predetermined height from the channel bottom surface. The plurality of reference electrodes 503 are located on a plane which is parallel to the chip surface and oppose the chip surface. The plane is located at a position higher than the plane with the working electrodes 501.

The upper surface of each detection channel 601*a* is defined by the bottom surface of the chip cartridge top cover 112 where the channel-shaped projecting portion 112*a* is not formed. A counter electrode 502 is fixed on each channel upper surface. The plurality of counter electrodes 502 are located on planes which are parallel to the chip surface and oppose the chip surface. The planes are located at positions higher than the planes with the working electrodes 502 and reference electrodes 503.

As described above, the working electrodes 501, counter electrodes 502, and reference electrodes 503 are three-dimensionally arranged on different planes.

The sealing member 24*a* is fixed on the channel-shaped projecting portion 112*a* of the chip cartridge top cover 112 in advance by printing. Hence, when the cell 115 is to be assembled, the chip cartridge top cover 112 integrated with the sealing member 24*a* is pressed against the base sequence detection chip 21 in a direction indicated by the arrows shown in FIG. 7B. Accordingly, the enclosed channel 601 as shown in FIG. 7A is defined between the channel-shaped projecting portion 112a and the base sequence detection chip 21 via the sealing member 24a.

As shown in FIG. 8, 3-electrodes each comprising the working electrode 501, counter electrode 502, and reference electrode 503 are arranged in each detection channel 601a at equal intervals along the flowing direction of a biochemical solution or air. The 3-electrodes are arranged on planes perpendicular to the flowing direction of a biochemical solution or air.

Figure 9:
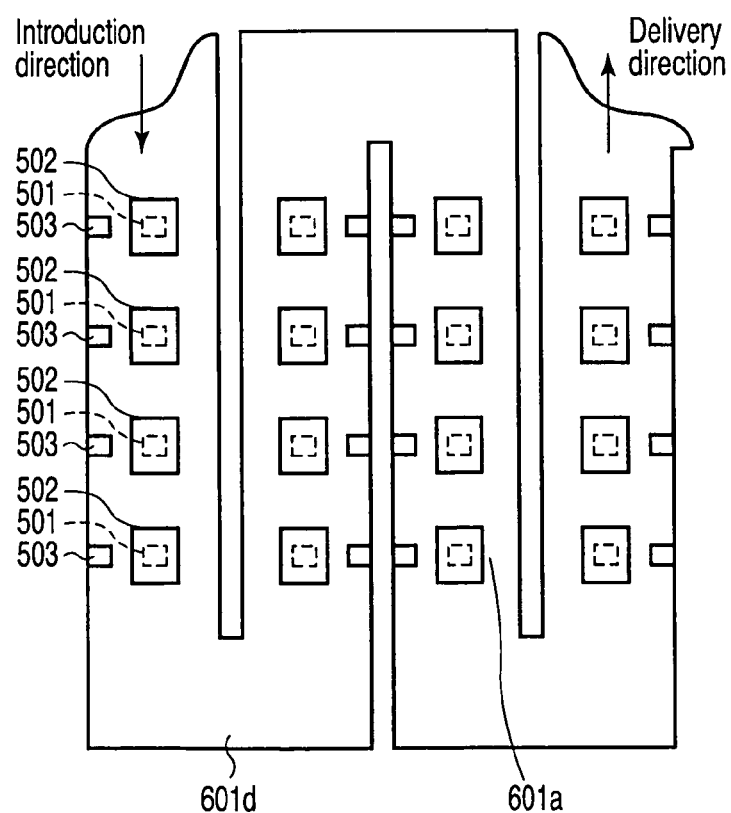
FIG. 9 is a plan view of a modification of the cell according to the first embodiment.

In the example shown in FIG. 8, the working electrodes 501, counter electrodes 502, and reference electrodes 503 have a matrix layout independently of the direction of the channel when viewed from the upper side. However, the present invention is not limited to this. As shown in FIG. 9, the direction of the channel section structure may be reversed between the adjacent detection channels 601a along the flowing direction of a biochemical solution or air. In this case, in all the detection channels 601a, the counter electrodes 502 are arranged on the right side surfaces of the channels along the flowing direction. Accordingly, 3-electrode layouts can be realized, which have the same shape along the flowing direction of a biochemical solution or air. If the working electrodes 501 and counter electrodes 502 are not laid out symmetrically in the channel sections, they can be laid out such that the layout direction is reversed between the channel sections of the adjacent detection channels 601a, like the reference electrodes 503.

As described above, sets of three electrodes comprising one working electrode 501, one counter electrode 502, and one reference electrode 503 are arranged in the channels having the same shape along the flowing direction of a biochemical solution or air. The 3-electrodes have the same positional relationship. The channel shapes are also the same. When viewed from the working electrode 501, the distances from the working electrode 501 to the channel bottom surface, side surface, and upper surface and the positional relationship with respect to the counter electrode 502 and reference electrode 503 corresponding to the working electrode 501 are the same for all the working electrodes 501. Accordingly, the uniformity of the electrochemical signal characteristic detected by each 3-electrode increases. As a result, the detection reliability increases.

In this example, the counter electrode 502 and reference electrode 503 are laid out separately from the corresponding working electrode 501. However, the present invention is not limited to this. The plurality of counter electrodes 502 or reference electrodes 503, or both of them may be connected. In that case, a region of each electrode, which is closest to a corresponding working electrode, functions as a counter electrode or reference electrode.

The sectional shape of the channel is not limited to the structure shown in FIG. 7A. FIG. 10 shows a modification of the sectional shape of the channel.

As shown in FIG. 10, a detection channel 601e has the base sequence detection chip 21 as a channel bottom surface. The side surfaces of the channel are defined by the side surfaces of the channel-shaped projecting portion 112a. The path width of the detection channel 601e becomes small upward from the channel bottom surface. The path width is zero at the top portion at the highest position. That is, the boundaries between the channel upper surface or the cell upper surface and the channel side surfaces or the cell side surfaces are not clearly defined. The counter electrode 502 is fixed near the channel top portion. The reference electrode 503 is fixed on a channel-shaped projecting portion 112c on the channel side surface, i.e., a plane located between the plane having the counter electrode 502 and the plane having the working electrode 501. Even in this channel sectional shape, the positional relationship between the three electrodes is the same as in FIG. 7A. The structure of the remaining parts is the same as in FIG. 7A, and a detailed description thereof will be omitted.

FIG. 11 shows another modification of the sectional shape of the channel. As shown in FIG. 11, the structure of the chip cartridge top cover 112 is the same as in FIG. 7A, including the structure of the channel-shaped projecting portion 112a. The structure shown in FIG. 11 is different from that shown in FIG. 7A in the layout of the reference electrode 503. In the example shown in FIG. 10, the reference electrode 503 is laid out side by side with the counter electrode 502 on the channel upper surface, i.e., the chip cartridge top cover 112. In this way, the counter electrode 502 and reference electrode 503 may be formed on the same plane.

Figure 12:
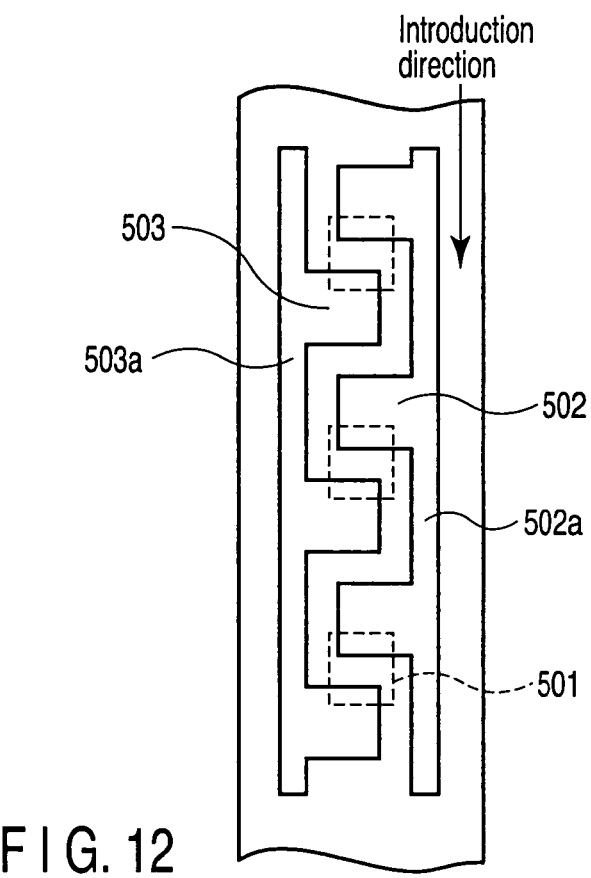
FIG. 12 is a plan view of a modification of a detection channel according to the first embodiment.

FIG. 12 is a plan view showing a modification of the detection channel 601a. In the example shown in FIG. 12, the working electrode 501, counter electrode 502, and reference electrode 503 are not arranged on the same channel section. Instead, they are arranged at sectional positions shifted from each other in the flowing direction of a biochemical solution or air. In addition, the plurality of counter electrodes 502 are connected by a wiring line 502a. The plurality of reference electrodes 503 are connected by a wiring line 503a. The working electrode 501, counter electrode 502, and reference electrode 503 are periodically arranged at equal intervals. However, the section on which the counter electrode 502 is formed does not overlap the section on which the reference electrode 503. The sections are arranged alternately along the flowing direction of a biochemical solution or air. When viewed from the upper side, the working electrode 501 and counter electrode 502 partially overlap. The reference electrode 503 and counter electrode 502 partially overlap.

As compared to the case wherein the counter electrode 502 and reference electrode 503 are laid out on the same section, the counter electrode 502 and reference electrode 503 can be arranged in a smaller region. As a result, the channel section can be made small, and the amount of a biochemical solution to be used can be saved.

Each counter electrode 502 is connected to the wiring line 502a. When the wiring line 502a is held at a predetermined potential, the plurality of counter electrodes 502 are held at the same voltage. Similarly, each reference electrode 503 is connected to the wiring line 503a. When the wiring line 503a is held at a predetermined potential, the plurality of reference electrodes 503 are held at the same voltage.

In the above example, the number of working electrodes 501, the number of counter electrodes 502, and the number of reference electrodes 503 equal. However, the numbers need not equal. In addition, the working electrode 501, reference electrode 503, and counter electrode 502 need not arranged at sectional positions shifted from each other. The electrodes need not be periodically arranged at equal intervals.

Figure 13A:
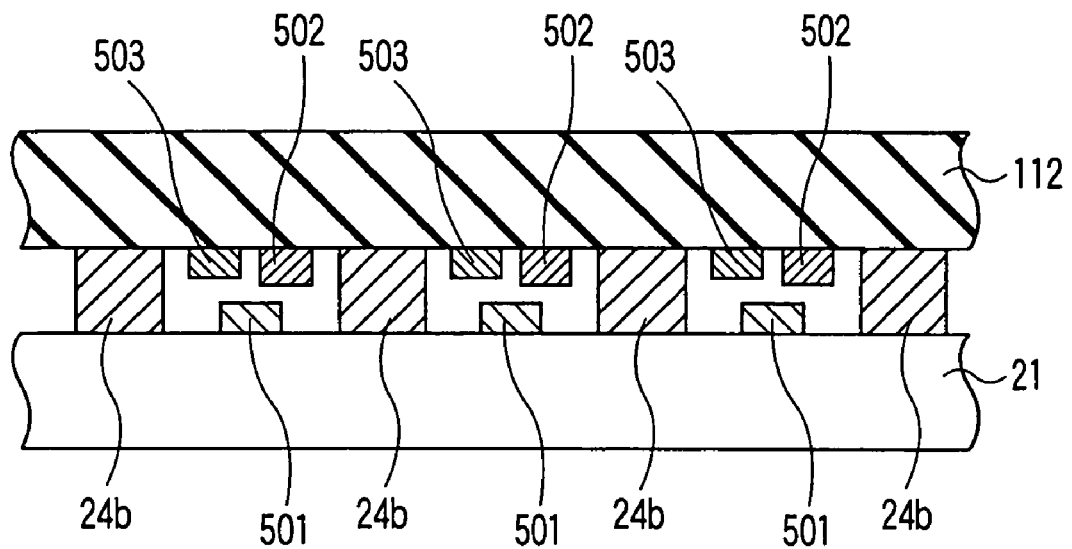
FIGS. 13A and 13B are views showing a modification of the structure of the cell according to the first embodiment.

FIG. 13A is a view showing a modification of the structure that defines the channel. The chip cartridge top cover 112 shown in FIG. 12A has a flat bottom surface and no channel-shaped projecting portion. A sealing member 24b is formed to be thicker than the sealing member 24a. The sealing member 24b is not fixed to the chip cartridge top cover 112 in advance.

Figure 13B:
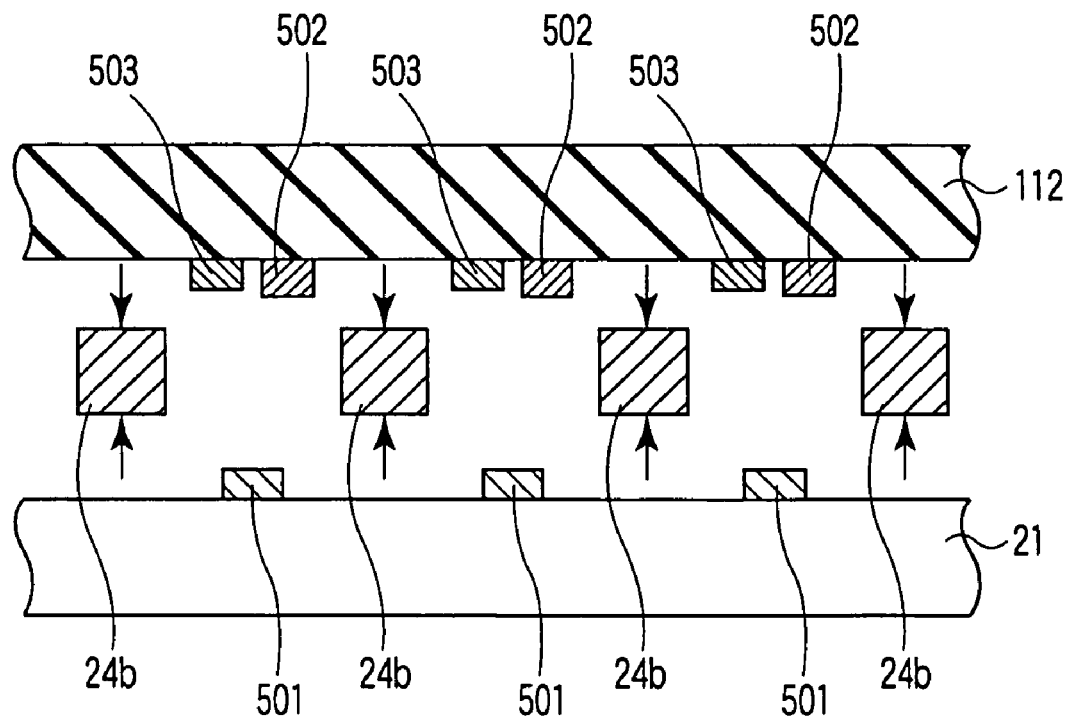

Hence, as shown in FIG. 13B, the chip cartridge top cover 112 is not fixed to the base sequence detection chip 21. In assembling the cell, the sealing member 24b is mounted on the base sequence detection chip 21. The sealing member 24b is sandwiched and fixed between the chip cartridge top cover 112 and the base sequence detection chip 21. With this structure, the enclosed space that surrounds the working electrodes 501, counter electrodes 502, and reference electrodes 503 is defined. This enclosed space is the channel 601. The counter electrodes 502 and reference electrodes 503 are laid out side by side on the bottom surface of the chip cartridge top cover 112. That is, the counter electrodes 502 and reference electrodes 503 are laid out on the same plane. In the cell 115 shown in FIGS. 13A and 13B, the cell bottom surface is defined by the base sequence detection chip 21. The cell side surfaces are defined by only the sealing member 24b. The cell upper surface is defined by the bottom surface of the chip cartridge top cover 112.

Figure 14:
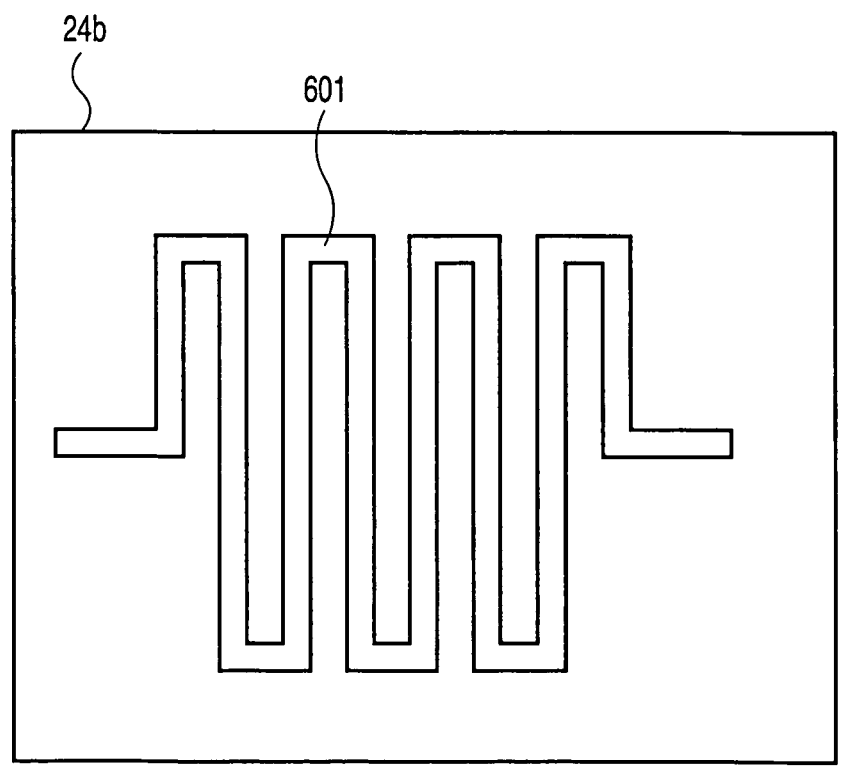
FIG. 14 is a view showing an example of the structure of a sealing member according to the first embodiment.

FIG. 14 is a view showing an example of the structure of the sealing member 24b. As shown in FIG. 14, the circular sealing member 24b has a channel-shaped hollow portion which extends from the upper surface side to the lower surface side along the shape of the channel 601. The sidewalls of the hollow portion function as channel walls. In the example shown in FIGS. 5A to 5C, the channel-shaped projecting portion 112a and sealing member 24a, which defines the channel, have circular outer shapes. However, any other outer shape can be used as long as the channel 601 can be defined. For example, the outer shape may be rectangular, as shown in FIG. 14.

Figure 34:
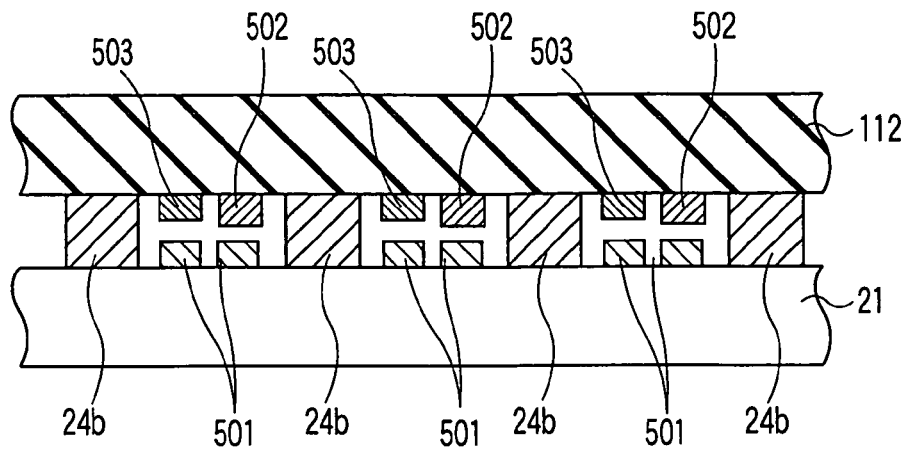
FIG. 34 is a view showing another modification of the cell according to the first embodiment.

FIG. 34 is a view showing another modification of the structure that defines the channel shown in FIG. 13A. In the example shown in FIG. 13A, each working electrode 501 is arranged on each section perpendicular to the flowing direction of a biochemical solution or cell so that the working electrodes 501 are one-dimensionally laid out along the channel. In the example shown in FIG. 34, however, two working electrodes 501 are arranged on each section perpendicular to the flowing direction of a biochemical solution or cell. That is, the working electrodes 501 are two-dimensionally laid out along the channel. In this manner, a predetermined number of working electrodes 501 may be arranged along the channel. In this case, each of the plurality of working electrodes 501 at the same sectional position makes a set with each of the counter electrode 502 and reference electrode 503 located at the section so that they function as a 3-electrode of a potentiostat.

A method of manufacturing the above-described base sequence detection chip 21 and printed board 22 will be described next with reference to the sectional views shown in FIGS. 15A to 15D.

A silicon substrate 211 is cleaned. After that, the silicon substrate 211 is heated to form a thermal oxide film 212 on the surface of the silicon substrate 211. A glass substrate may be used in place of the silicon substrate 211.

A Ti film 213 having a thickness of, e.g., 50 nm and then an Au film 214 having a thickness of, e.g., 200 nm are formed on the entire substrate surface by sputtering. The of the Au film 214 is preferably <111> orientation. A photoresist film 210 is patterned such that regions serving as prospective electrodes and wiring lines are protected (FIG. 15A). The Au film 214 and Ti film 213 are etched (FIG. 15B). In this embodiment, a $KI/I_2$ solution mixture is used to etch the Au film 214. An $NH_4OH/H_2O_2$ solution mixture is used to etch Ti. To etch the Au film 214, diluted aqua regia may be used. Alternatively, the Au film 214 may be removed by ion milling. The Ti film 213 may also be wet-etched using hydrofluoric acid or buffered hydrofluoric acid. Alternatively, dry etching using a plasma by, e.g., a $CF_4/O_2$ mixed gas can also be applied.

Next, the photoresist film 210 is removed by oxygen ashing (FIG. 15C). The removal process of the photoresist film 210 may be executed using a solvent or a resist stripper. Alternatively, these methods and the oxygen ashing process may be combined.

A photoresist 215 is applied to the entire surface and patterned to form openings corresponding to electrode portions and bonding pads (FIG. 15D). After that, the resultant structure is hard-baked in a clean oven at, e.g., 200° C. for 30 min. Hard baking may be executed using a hotplate. The processing conditions may also be appropriately changed.

In this example, the photoresist 215 is selected as a protective film. However, the present invention is not limited to this. Instead of a photoresist, an organic film made of polyimide or BCB (benzocyclobutene) may be used as a protective film.

Alternatively, an inorganic film of SiO, $SiO_2$, or SiN may be used as a protective film. For example, when SiO is used, openings are formed in the photoresist such that electrode portions are protected. Then, SiO is deposited. Regions except the electrode portions are protected by lift-off. For example, if SiN is used, SiN is formed on the entire surface. After that, the photoresist 215 is formed and patterned such that openings are formed in correspondence with only electrode portions. Then, the SiN film on the electrodes is removed. Finally, the photoresist 215 is removed.

Chips are formed by executing dicing. Finally, to clean the electrode portion surface, a process by a $CF_4/O_2$ plasma mixture is executed. With these processes, the base sequence detection chip 21 is obtained. The base sequence detection chip 21 is mounted on the printed board 22 to which the electrical connector 22a is attached. The bonding pads of the base sequence detection chip 21 are connected to lead wires on the printed board 22 by wire bonding. After that, the wire bonding portion is protected using the encapsulating resin 23.

With the above process, the printed board 22 having the base sequence detection chip 21 mounted thereon can be manufactured.

Figure 16:
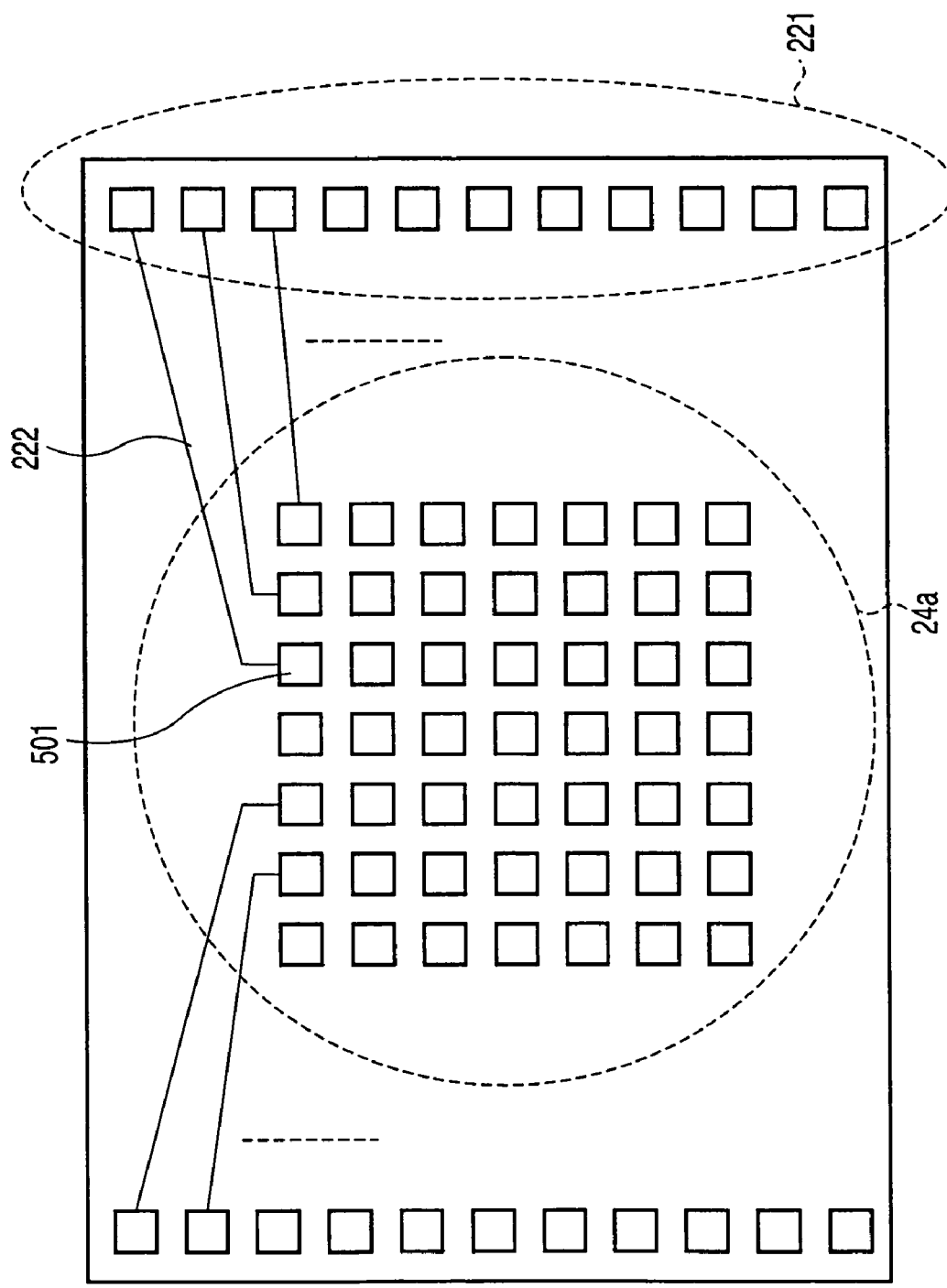
FIG. 16 is a plan view of the base sequence detection chip according to the first embodiment.

FIG. 16 is a plan view of the resultant base sequence detection chip 21. As shown in FIG. 16, the plurality of working electrodes 501 are arranged near the center of the chip surface. The region where the working electrodes 501 are formed is smaller than the formation region of the sealing member 24a, which is indicated by a broken line. Bonding pads 221 are laid out around the chip peripheral portion. Each of the working electrodes 501 is connected to a corresponding one of the bonding pads 221 by a wire 222. Although not illustrated, the peripheral portion where the bonding pads 221 are formed is encapsulated by the above-described encapsulating resin 23.

A detailed arrangement of the solution supply system 13 will be described next with reference to FIG. 17. The solution supply system 13 is roughly divided into a supply system arranged on the side of the channel 114a of the chip cartridge 11 and a discharge system arranged on the side of the channel 114b.

An air supply source 401 is connected to the most upstream portion of a pipe 404. A check valve 402 is arranged downstream of the air supply source 401. The check valve 402 prevents a biochemical solution except air from flowing back to the air supply source 401 through the pipe 404. A two-way solenoid valve 403 ($V_a$) is arranged downstream of the check valve 402. The two-way solenoid valve 403 controls the flow rate of air from the pipe 404 to the chip cartridge 11.

A milli-Q water supply source 411 which stores milli-Q water as one of biochemical solutions is connected to a pipe 414. A check valve 412 is arranged downstream of the milli-Q water supply source 411. The check valve 412 prevents a biochemical solution except the milli-Q water or air from flowing back to the milli-Q water supply source 411. A three-way solenoid valve 413 ($V_{wa}$) is arranged downstream of the check valve 412. The three-way solenoid valve 413 switches between communication of the pipe 404 and a pipe 415 and communication of the pipe 414 and pipe 415. More specifically, when the three-way solenoid valve 413 is not electrically turned on, the pipe 404 communicates with the pipe 415. When the three-way solenoid valve 413 is electrically turned on, the pipe 414 communicates with the pipe 415. Accordingly, supply of air and supply of milli-Q water to the pipe 415 can be switched.

A buffer supply source 421 which stores a buffer (buffer solution) as one of biochemical solutions is connected to a pipe 424. A check valve 422 is arranged downstream of the buffer supply source 421. The check valve 422 prevents a biochemical solution except the buffer or air from flowing back to the buffer supply source 421. A three-way solenoid valve 423 ($V_{ba}$) is arranged downstream of the check valve 422. The three-way solenoid valve 423 switches between communication of the pipe 424 and a pipe 425 and communication of the pipe 415 and pipe 425. More specifically, when the three-way solenoid valve 423 is not electrically turned on, the pipe 415 communicates with the pipe 425. When the three-way solenoid valve 423 is electrically turned on, the pipe 424 communicates with the pipe 425. Accordingly, supply of buffer and supply of air or milli-Q water to the pipe 425 can be switched.

An intercalating agent supply source 431 which stores an intercalating agent as one of biochemical solutions is connected to a pipe 434. A check valve 432 is arranged downstream of the intercalating agent supply source 431. The check valve 432 prevents a biochemical solution except the intercalating agent or air from flowing back to the intercalating agent supply source 431. A three-way solenoid valve 433 ($V_{in}$) is arranged downstream of the check valve 432. The three-way solenoid valve 433 switches between communication of the pipe 434 and a pipe 435 and communication of the pipe 425 and pipe 435. More specifically, when the three-way solenoid valve 433 is not electrically turned on, the pipe 425 communicates with the pipe 435. When the three-way solenoid valve 433 is electrically turned on, the pipe 434 communicates with the pipe 435. Accordingly, supply of buffer and supply of air, milli-Q water, or buffer to the pipe 435 can be switched.

As described above, in the supply system of air or a biochemical solution, the two-way solenoid valve 403 and three-way solenoid valves 413, 423, and 433 are controlled. With this operation, supply of air and supply of a biochemical solution such as milli-Q water, a buffer, or an intercalating agent, which is to be supplied to the chip cartridge 11 through the pipe 435, can be switched. In addition, the flow rate of air or a biochemical solution to be supplied can be controlled.

The above-described three-way solenoid valve 433 communicates with the upstream side of the pipe 435. A three-way solenoid valve 441 ($V_{cbin}$) communicates with the downstream side of the pipe 435. With the three-way solenoid valve 441, the pipe 435 can be branched to a pipe 440 and bypass pipe 446. When the three-way solenoid valve 441 is not electrically turned on, the pipe 435 communicates with the bypass pipe 446. When the three-way solenoid valve 441 is electrically turned on, the pipe 435 communicates with the pipe 440. When a three-way solenoid valve 445 is not electrically turned on, the bypass pipe 446 communicates with a pipe 450. When the three-way solenoid valve 445 is electrically turned on, the pipe 440 communicates with the pipe 450. With the three-way solenoid valves 441 and 445, supply of various kinds of biochemical solutions or air can be switched to the bypass pipe 446 or pipe 440.

A two-way solenoid valve 442 ($V_{1in}$), the chip cartridge 11, a liquid sensor 443, a two-way solenoid valve 444 ($V_{1out}$), and the three-way solenoid valve 445 ($V_{cbout}$) are arranged downstream sequentially from the three-way solenoid valve 441. The channel 114a corresponding to the introduction system of the chip cartridge 11 communicates with the two-way solenoid valve 442. The channel 114b corresponding to the delivery system of the chip cartridge 11 communicates with the two-way solenoid valve 444. Accordingly, a biochemical solution or air can be supplied to the introduction system of the chip cartridge 11 through the pipe 440. In addition, the biochemical solution or air can be delivered from the delivery system of the chip cartridge 11. The two-way solenoid valves 442 and 444 control the flow rate of a biochemical solution or air in the solution supply and discharge paths. In addition, the liquid sensor 443 can monitor the flow rate of a biochemical solution which enters the chip cartridge 11 or is discharged from the chip cartridge 11.

A two-way solenoid valve 451 ($V_{vin}$), a decompression region 452, a two-way solenoid vale 453 ($V_{out}$), a solution supply pump 454, and a three-way solenoid valve 455 ($V_{ww}$) are arranged downstream sequentially from the three-way solenoid valve 445. The two-way solenoid valves 451 and 453 prevent backflow of a biochemical solution or air in the paths before and after the decompression region 452. The solution supply pump 454 comprises a tube pump. As a characteristic feature, the solution supply pump 454 is arranged in the discharge system on the delivery side (downstream side) of the chip cartridge 11. More specifically, when the tube pump is used, the biochemical solution does not come into contact with mechanisms except the tube wall. This structure is preferable from the viewpoint of preventing contamination. Supply/discharge of a biochemical solution or air to/from the chip cartridge 11 is executed by a suction operation. With this operation, a biochemical solution and air can smoothly replace in the chip cartridge 11. Even if the pipes slack or the chip cartridge 11 is detached from the pipe 440, no solution leakage occurs. As a result, the safety of apparatus installation increases.

The pump may be arranged on a pipe upstream of the chip cartridge 11. Air or a biochemical solution may be supplied to the chip cartridge 11 by the pump. The pump is not limited to a tube pump. A syringe pump, plunger pump, diaphragm pump, or magnet pump may be used.

When the three-way solenoid valve 455 is not electrically turned on, the pipe 450 communicates with a pipe 461. When the three-way solenoid valve 455 is electrically turned on, the pipe 450 communicates with a pipe 463. The pipe 461 has a waste liquid tank 462. The pipe 463 has a waste intercalating agent tank 464. By switching the three-way solenoid valve 455, a biochemical solution such as milli-Q water or a buffer except an intercalating agent can be fed to the waste liquid tank 462, or an intercalating agent can be fed to the waste intercalating agent tank 464. Accordingly, the intercalating agent can be separately collected.

The solenoid valves may be connected by pipes such as Teflon tubes. In this embodiment, manifold structures are formed on both of the upstream and downstream sides of the chip cartridge 11 so that the solenoid valves and channels have integral structures. With this structure, the capacity in the pipes decreases. Hence, the necessary amount of a biochemical solution can greatly be reduced. In addition, the biochemical solution flow in the pipes stabilizes. Hence, the reproducibility and stability of the detection result increase.

A solution supply step for base sequence detection using the solution supply system 13 shown in FIG. 17 will be described with reference to the flow chart shown in FIG. 18.

First, a hybridization reaction between a sample and DNA probes immobilized to the working electrode 501 is executed in the cell 115 (s21). In executing the hybridization reaction, the temperature control mechanism 14 is controlled such that, e.g., the bottom surface of the chip cartridge 11, i.e., the bottom surface of the printed board 22 becomes about 45° C. This temperature is held for, e.g., 60 min.

In parallel to this hybridization reaction, the biochemical solution line is set up (s22). More specifically, by controlling, the three-way solenoid valves 441 and 445, the structure on the side of the bypass pipe 446 is used. The three-way solenoid valve 433 is electrically turned on to supply an intercalating agent from the intercalating agent supply source 431 for about 10 sec. The three-way solenoid valve 455 is electrically turned on to store the intercalating agent from the pipe 450 in the waste intercalating agent tank 464. The intercalating agent and air are alternately repeatedly introduced from the pipe 435 to the bypass pipe 446 for, e.g., about 5 sec each. Next, only air is introduced from the pipe 435 to the bypass pipe 446. At this time, the waste liquid is switched to the waste liquid tank 462. A buffer is introduced from the buffer supply source 421 to the bypass pipe 446. After that, milli-Q water and air are alternately repeatedly introduced from the pipe 435 to the bypass pipe 446 for, e.g., about 5 sec each.

When the biochemical solution line is set up, and the hybridization reaction is ended, pipe cleaning is executed (s23). In pipe cleaning, for example, the temperature of the printed board 22 is set to about 25° C. by the temperature control mechanism 14. The bypass pipe 446 is purged with milli-Q water. Then, air and milli-Q water are alternately repeatedly introduced for, e.g., about 5 sec each. Next, the chip cartridge is cleaned (s24). In chip cartridge cleaning, the biochemical solution introduction path is switched from the bypass pipe 446 to the pipe 440. Air and milli-Q water are alternately repeatedly introduced to the pipe 440 for, e.g., about 5 sec each. After it is confirmed by the liquid sensor 443 that the chip cartridge 11 is filled with water, the introduction path is switched to the bypass pipe 446.

Next, pipe buffer purge is executed (s25). In pipe buffer purge, first, air is introduced to the bypass pipe 446 such that the buffer and milli-Q water do not mix. Next, air and the buffer are alternately repeatedly introduced to the bypass pipe 446 for, e.g., about 5 sec each. It is confirmed by a liquid sensor 447 arranged on the bypass pipe 446 that the bypass pipe 446 is replaced with the buffer.

Next, chip cartridge buffer injection is executed (s26). In chip cartridge buffer injection, first, the bypass pipe 446 is switched to the pipe 440. Air and the buffer are alternately repeatedly introduced into the chip cartridge 11 for, e.g., about 5 sec each.

Then, buffer filling into the chip cartridge 11 is executed (s27). In buffer filling, the buffer is introduced into the chip cartridge 11 while monitoring the state in the chip cartridge 11 with the liquid sensor 443. The chip cartridge 11 is left to stand at, e.g., 60° C. for 30 min. With this process, the unnecessary sample is cleaned (s28). After the unnecessary sample cleaning step, the pipe 440 is switched to the bypass pipe 446, and milli-Q water is introduced. Thus, pipe cleaning is executed (s29). In pipe cleaning, air and milli-Q water are alternately repeatedly introduced again for, e.g., about 5 sec each.

Next, chip cartridge cleaning is executed (s30). In chip cartridge cleaning, the bypass pipe 446 is switched to the chip cartridge 11. Air and water are alternately repeatedly introduced for, e.g., about 5 sec each. After it is confirmed by the liquid sensor 443 that the chip cartridge 11 is filled with milli-Q water, the introduction path is switched to the bypass pipe 446.

Next, measurement starts. In the measurement, pipe intercalating agent purge is executed first (s31). In pipe intercalating agent purge, the waste liquid is switched to the waste intercalating agent tank 464 while introducing air to the bypass pipe 446. Next, air and the intercalating agent are alternately repeatedly introduced to the bypass pipe 446 for, e.g., about 5 sec each. After that, it is detected by the liquid sensor 447 whether the bypass pipe 446 is replaced with the intercalating agent.

Next, the intercalating agent is injected into the chip cartridge 11 (s32). In this step, the bypass pipe 446 is switched to the side of the chip cartridge 11. After that, air and the intercalating agent are alternately repeatedly introduced, e.g., about 5 sec each.

Next, under monitoring by the liquid sensor 443, the chip cartridge 11 is filled with the intercalating agent (s33). Then, measurement is executed (s34).

When measurement is ended, milli-Q water is introduced to the bypass pipe 446. Air and milli-Q water are alternately introduced, e.g., about 5 sec each. The bypass pipe 446 is replaced with air to execute pipe cleaning (s35).

Finally, the bypass pipe 446 is replaced to the chip cartridge 11. Air and milli-Q water are alternately introduced, e.g., about 5 sec each. The chip cartridge 11 is replaced with air to execute chip cartridge cleaning (s36). Thus, the series of solution supply steps are ended.

Figure 17:
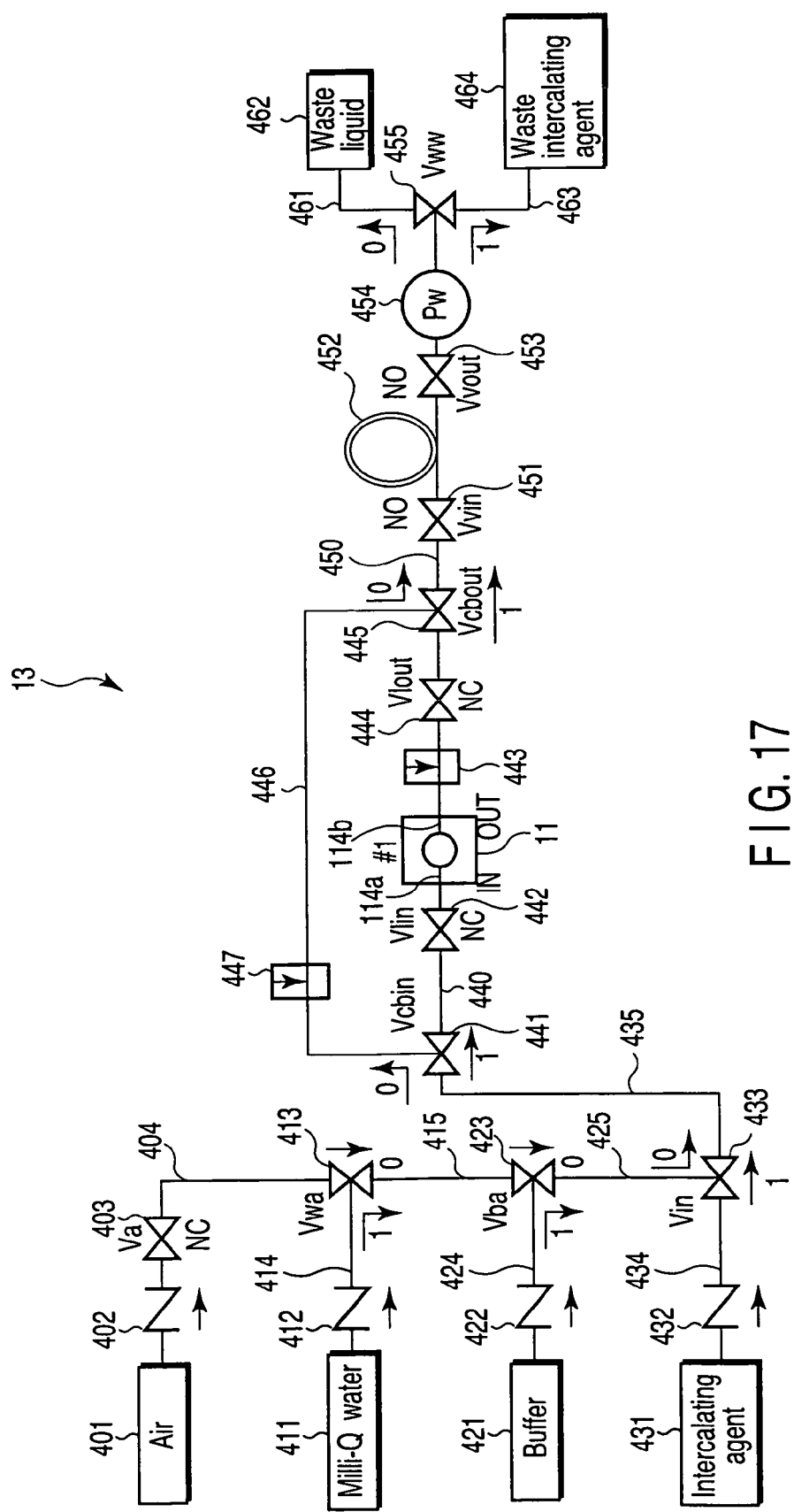
FIG. 17 is a view showing a detailed arrangement of a solution supply system according to the first embodiment.

As described above, according to the steps shown in FIG. 18, which uses the solution supply system 13 shown in FIG. 17, to efficiently replace biochemical solutions, the solutions can be supplied on the basis of a sequence in which air and a biochemical solution alternately flow through the pipe in an order of biochemical solution/air/biochemical solution/air. When this solution supply method is used, mixing of a preceding biochemical solution and a current biochemical solution in biochemical solution replacement can be minimized. As a result, the number of solution exchange transition states decreases. The reproducibility of the final electrochemical characteristic can be increased. In addition, when the efficiency of biochemical solution exchange increases, the solution supply time can be shortened, and the amount of biochemical solution can be decreased. Furthermore, when solution supply is executed on the basis of such a biochemical solution/air sequence, the biochemical solution concentration in the reaction cell 115 can always be kept constant. For this reason, the in-plane uniformity of the current characteristic increases. That is, the detection reliability increases.

As a method of filling the cell 115 with a biochemical solution, the two-way solenoid valve 444 serving as a chip cartridge outlet valve is closed. In this state, a decompression state is set in the pipe 440 downstream of the chip cartridge. Then, the two-way solenoid valve 444 is opened. With this method, a biochemical solution can be introduced into the chip cartridge reaction cell 115. The decompression state in the decompression region 452 is held in the following way. The pump 454 is operated. In this state, the two-way solenoid valve 451 is controlled to reduce the pressure in the decompression region 452. Then, the two-way solenoid vale 453 is controlled.

Figure 18:
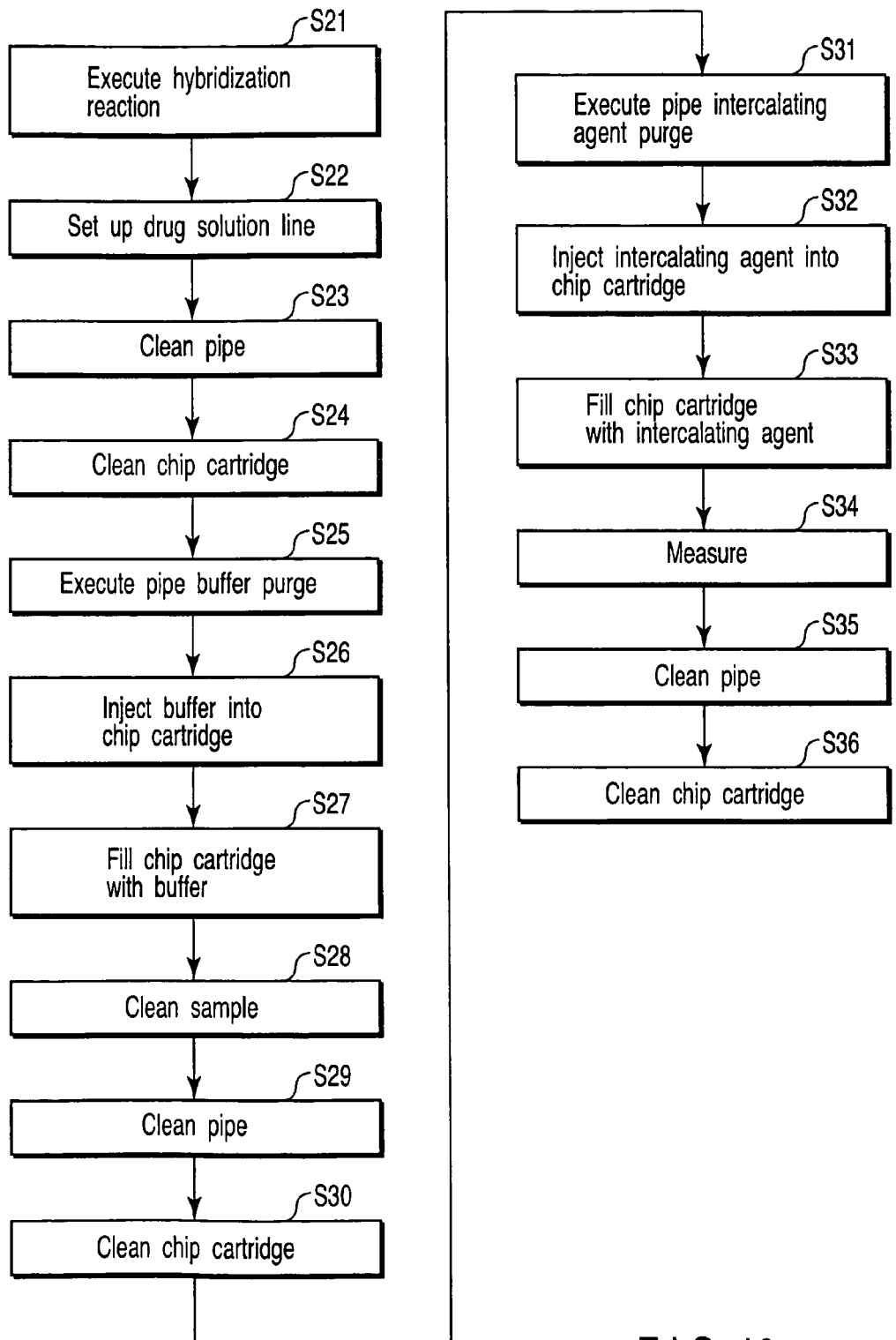
FIG. 18 is a flow chart of a solution supply step for base sequence detection using the according to the first embodiment.

The solution supply timing shown in FIG. 18 is merely an example and can be modified in various ways in accordance with the purpose, object, and conditions of measurement.

Figure 19:
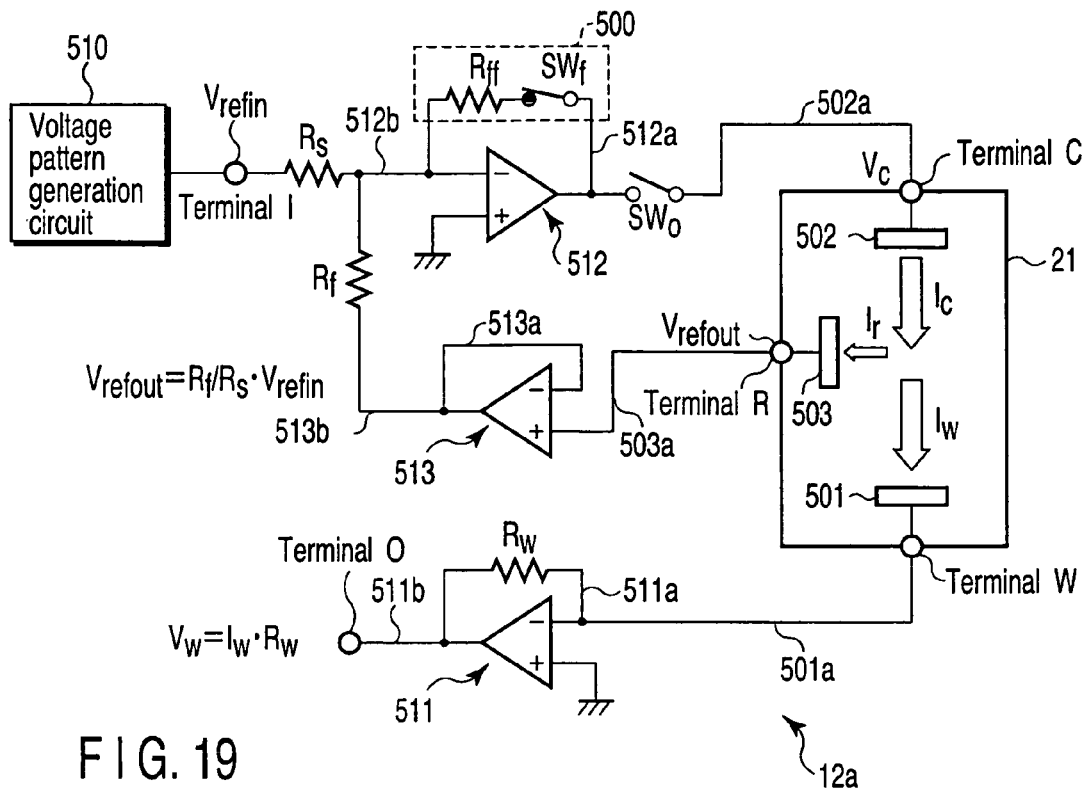
FIG. 19 is a view showing the detailed arrangement of a measurement system according to the first embodiment.

FIG. 19 is a view showing the detailed arrangement of the measurement system 12. The measurement system 12 shown in FIG. 19 comprises a 3-electrode potentiostat 12*a*. The potentiostat 12a feeds back (negative feedback) the voltage of the reference electrode 503 to the input of the counter electrode 502, thereby applying a desired voltage to a solution independently of the variation in various conditions of the electrodes or solution in the cell 115.

More specifically, the potentiostat 12a changes the voltage of the counter electrode 502 to set the voltage of the reference electrode 503 corresponding to the working electrode 501 to a predetermined characteristic. Then, the potentiostat 12a electrochemically measures the oxidation current of an intercalating agent.

The working electrode 501 is an electrode to which a DNA probe is immobilized. The DNA probe has a target complementary base sequence complementary to a target base sequence. The working electrode 501 is an electrode that detects a reaction current in the cell 115. The counter electrode 502 is an electrode that applies a predetermined voltage between the counter electrode 502 and the working electrode 501 to supply a current into the cell 115. The reference electrode 503 is an electrode that feeds back the electrode voltage to the counter electrode 502 to control the voltage between the reference electrode 503 and the working electrode 501 to a predetermined voltage characteristic. By feedback from the reference electrode 503, the voltage by the counter electrode 502 is controlled. As a result, accurate oxidation current detection can be executed without being influenced by various detection condition in the cell 115.

A voltage pattern generation circuit 510 is connected to the inverting input terminal of an inverting amplifier 512 ($OP_c$) for reference voltage control of the reference electrode 503 through a wiring line 512b. The voltage pattern generation circuit 510 generates a voltage pattern to detect the current that flows between the electrodes.

The voltage pattern generation circuit 510 converts a digital signal input from the control mechanism 15 into an analog signal to generate a voltage pattern. The voltage pattern generation circuit 510 has a D/A converter.

A resistance $R_s$ is connected to the wiring line 512b. The non-inverting input terminal of the inverting amplifier 512 is grounded. The wiring line 502a is connected to the output terminal of the inverting amplifier 512. The wiring line 512b on the inverting input terminal side of the inverting amplifier 512 is connected to the wiring line 502a on the output terminal side by a wiring line 512a. The wiring line 512a has a protective circuit 500 formed from a feedback resistance $R_{ff}$ and a switch $SW_f$.

The wiring line 502a is connected to a terminal C. The terminal C is connected to the counter electrode 502 on the base sequence detection chip 21. When a plurality of counter electrodes 502 are formed, the terminal C is connected in parallel with the counter electrodes 502. Accordingly, a voltage can simultaneously be applied to the plurality of counter electrodes 502 in accordance with one voltage pattern.

The wiring line 502a has a switch $SW_0$ which ON/OFF-controls voltage application to the terminal C.

The protective circuit 500 arranged in the inverting amplifier 512 prevents any excessive voltage from being applied to the counter electrode 502. No excessive voltage that electrolyzes a solution is applied at the time of measurement. Oxidation current detection of a desired intercalating agent is not affected. Hence, stable measurement can be executed.

A terminal R is connected to the non-inverting input terminal of a voltage follower amplifier 513 ($OP_r$) by the wiring line 503a. The inverting input terminal of the voltage follower amplifier is short-circuited, through a wiring line 513a, to a wiring line 513b which is connected to the output terminal of the voltage follower amplifier. The wiring line 513b has a resistance $R_f$. The resistance $R_f$ is connected between the resistance of the wiring line 512b and the intersection between the wiring lines 512a and 512b. A voltage obtained by feeding back the voltage of the reference electrode 503 to the voltage pattern generated by the voltage pattern generation circuit 510 is input to the inverting amplifier 512. The voltage of the counter electrode 502 is controlled on the basis of an output obtained by inverting and amplifying these voltages.

A terminal W is connected to the inverting input terminal of a trans-impedance amplifier 511 ($OP_w$) by a wiring line 501a. The non-inverting input terminal of the trans-impedance amplifier 511 is grounded. A wiring line 511b connected to the output terminal is connected to the wiring line 501a through a wiring line 511a. The wiring line 511a has a resistance $R_w$. Letting $V_w$ be the voltage of a terminal O on the output side of the trans-impedance amplifier 511, and $I_w$ be the current, $V_w=I_w \cdot R_w$. An electrochemical signal obtained from the terminal O is output to the control mechanism 15. Since there are a plurality of working electrodes 501, a plurality of terminals W and a plurality of terminals O are arranged in correspondence with the working electrodes 501. The outputs from the plurality of terminals O are switched by a signal switching section (to be described later) and A/D-converted so that electrochemical signals from the working electrodes 501 can be almost simultaneously obtained as digital values. The circuits such as the trans-impedance amplifier 511 between the terminal W and the terminal O may be shared by the plurality of working electrodes 501. In this case, a signal switching section which switches between wiring lines from the plurality of terminals W is arranged in the wiring line 501a.

Figure 20:
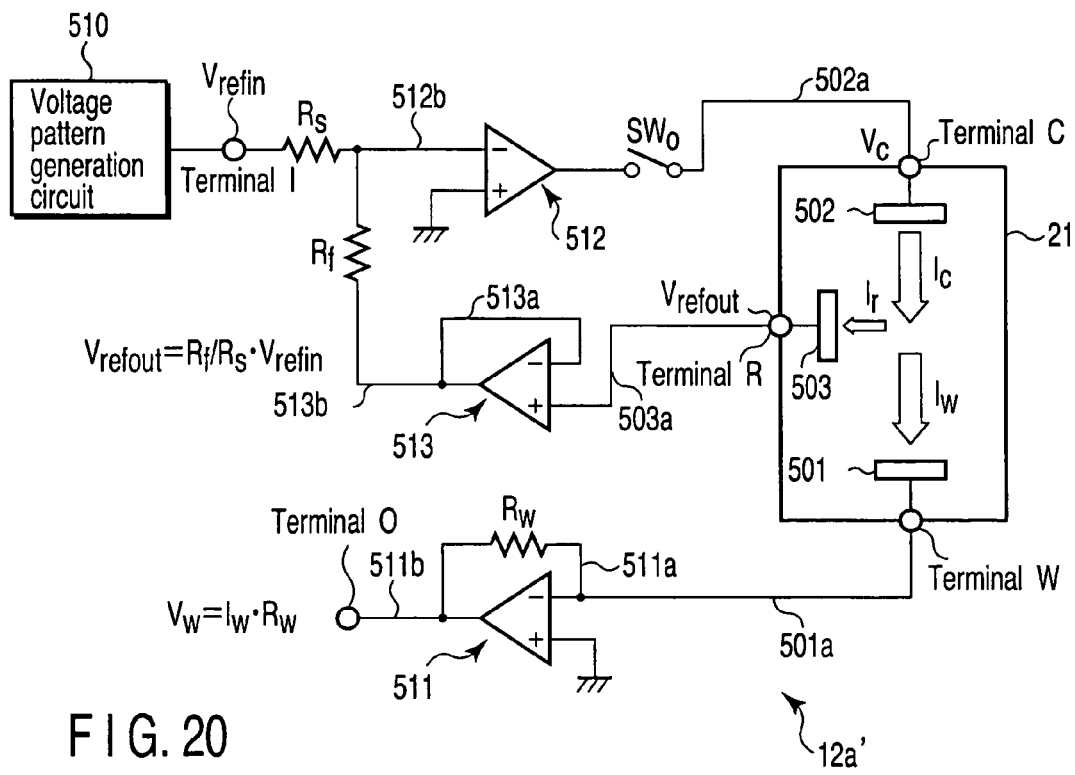
FIG. 20 is a view showing the arrangement of a conventional potentiostat.

The effect of the measurement system 12 using the potentiostat 12a shown in FIG. 19 will be described in comparison to the effect obtained using a conventional potentiostat. As shown in FIG. 20, the arrangement of a conventional potentiostat 12a' is almost the same as that of the measurement system 12 shown in FIG. 19. A difference is that the inverting amplifier 512 has no protective circuit 500. Let $V_{refin}$ be the voltage at a terminal I of the voltage pattern generation circuit 510, $V_c$ be the voltage at the terminal C, and $V_{refout}$ be the voltage at the terminal R. By feedback of the reference electrode 503, $V_{refout}=R_f/R_s \cdot V_{refin}$ holds.

In this case, examples of the voltage $V_{refin}$, the switch change-over states of the switches $SW_0$ and $SW_f$, the voltage characteristics and switch change-over states of the voltages $V_c$ and $V_{refout}$ are shown in FIGS. 21A to 21E and FIGS. 22A to 22D. FIGS. 21A to 21E show waveforms of the potentiostat 12a. FIGS. 22A to 22D show the waveforms of the potentiostat 12a'.

FIG. 21A shows the voltage waveform of the voltage $V_{refin}$. FIG. 21B shows the switch change-over state of the switch $SW_0$. FIG. 21C shows the switch change-over state of the switch $SW_f$. FIG. 21D shows the voltage waveform of the voltage $V_c$. FIG. 21E shows the voltage waveform of the voltage $V_{refout}$.

FIG. 22A shows the voltage waveform of the voltage $V_{refin}$. FIG. 22B shows the switch change-over state of the switch $SW_0$. FIG. 22C shows the voltage waveform of the voltage $V_c$. FIG. 22D shows the voltage waveform of the voltage $V_{refout}$.

A measuring method in the conventional potentiostat 12a' will be described with reference to FIGS. 22A to 22D.

For example, as shown in FIG. 22A, the voltage pattern generation circuit 510 generates a voltage pattern which gives a predetermined voltage from times $t_1$ to $t_3$ and then linearly decreases and nullifies it at time $t_4$. For example, assume a case wherein the switch $SW_0$ is turned on to apply a voltage to the counter electrode 502 at time $t_2$ after the elapse of a predetermined time from time $t_1$, as shown in FIG. 22B. In this case, at the start of measurement, i.e., before the switch $SW_0$ is turned on, the switch $SW_0$ is OFF.

The gain of the inverting amplifier 512 is very large. Hence, if a slight voltage is applied to the inverting input terminal of the inverting amplifier 512 before the switch $SW_0$ is turned on to form the feedback loop, the output from the inverting amplifier 512 is saturated. On the other hand, even when the voltage $V_{refin}$ is 0 V, a saturated state is set because of the input offset voltage of the inverting amplifier 512. In this case, saturation occurs to a polarity opposite to that of the input offset voltage.

As described above, the output voltage of the inverting amplifier 512 is saturated almost to the power supply voltage of the inverting amplifier 512. Hence, when the switch $SW_0$ is turned on, an excessive voltage is applied to the counter electrode 502. This excessive voltage corresponds to the hatched portion in FIG. 22A. The excessive voltage causes an undesirable electrochemical reaction such as electrolysis in a solution in the cell 115. As a result, measurement of an electrochemical reaction that is originally desired is adversely affected.

To solve the problem of the conventional potentiostat 12a', the potentiostat 12a of this embodiment uses the protective circuit 500. In the potentiostat 12a of this embodiment, before the start of measurement, i.e., in the initial state before time $t_a$, the voltage $V_{refin}$ is set to 0 V, the switch $SW_f$ is set in the ON state, and the switch $SW_0$ is set in the OFF state. First, the switch $SW_0$ is turned on at time ta. In this state, the switch $SW_f$ is still OFF, and the protective circuit 500 does not function. Since the inverting amplifier 512 is always used with feedback, no excessive voltage is applied to the counter electrode 502.

At time $t_b$ after the elapse of a predetermined time from time $t_a$, the switch $SW_f$ is turned on to cause the protective circuit 500 to function. After that, from time $t_1$, the voltage $V_{refin}$ generated by the voltage pattern generation circuit 510 is applied. With the voltage $V_{refin}$, a desired voltage is set in the reference electrode 503. Since the response has a first-order lag characteristic, no excessive voltage is applied to the counter electrode 502.

Figure 23:
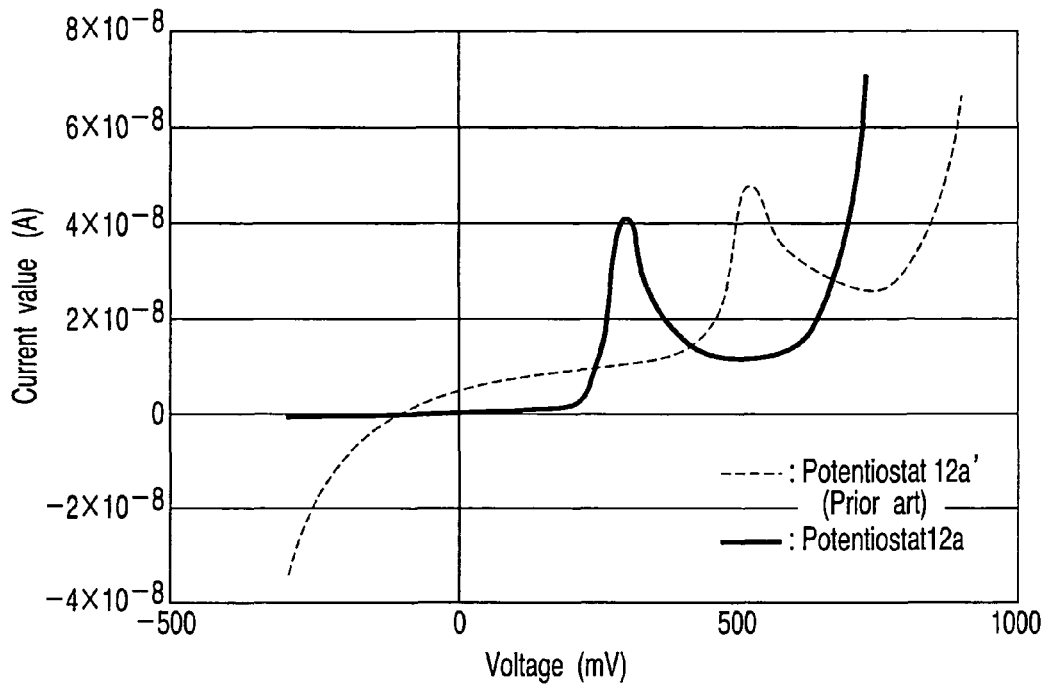
FIG. 23 is a graph showing current/voltage characteristic curves applied to counter electrodes in a potentiostat according to the first embodiment and the conventional potentiostat.

FIG. 23 is a graph showing current/voltage characteristic curves applied to the counter electrodes 502 in the potentiostats 12a and 12a'. As shown in FIG. 23, in the conventional potentiostat 12a', both the current and the voltage may have large negative values. In the potentiostat 12a of this embodiment, however, even when the voltage has a negative value, the current keeps a predetermined value. Conventionally, when the voltage has a negative value, undesirable electrolysis in the solution in the cell 115 progresses. This may, e.g., generate bubbles in the electrodes or change the composition of the electrode. When the protective circuit 500 is used, as in this embodiment, any undesirable voltage can be prevented from being applied to the counter electrode 502. Hence, any undesirable electrolysis in the solution in the cell 115 can be avoided. As described above, stable measurement can be executed without any adverse effect on oxidation current detection of a desired intercalating agent.

Figure 24:
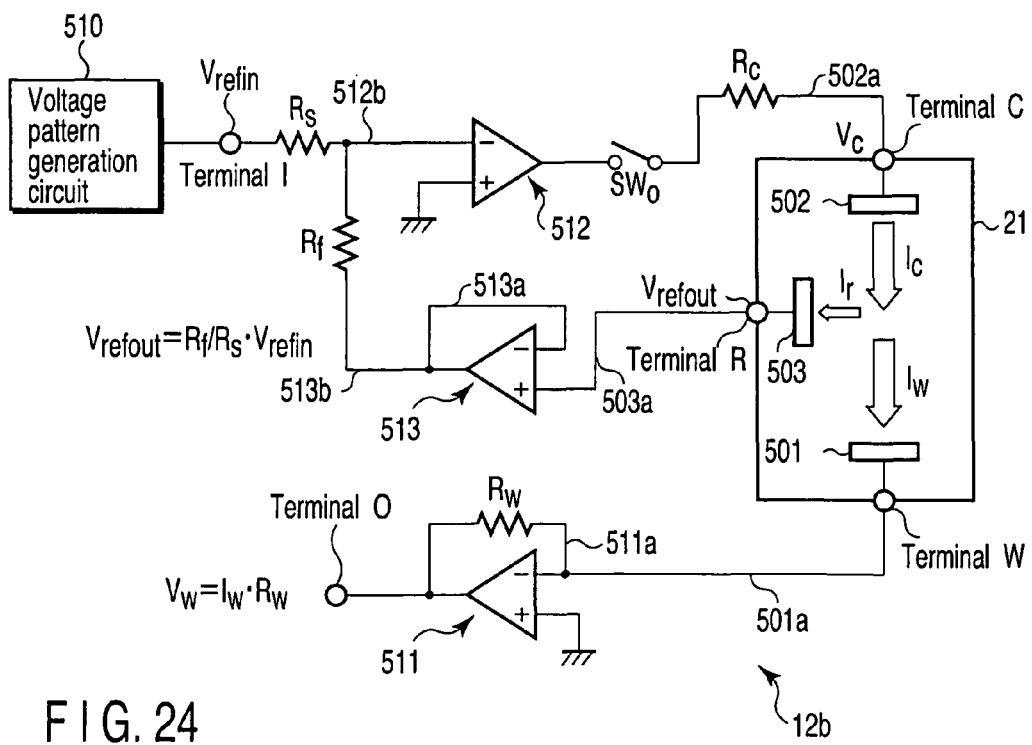
FIG. 24 is a view showing a modification of the potentiostat according to the first embodiment.
Figure 25:
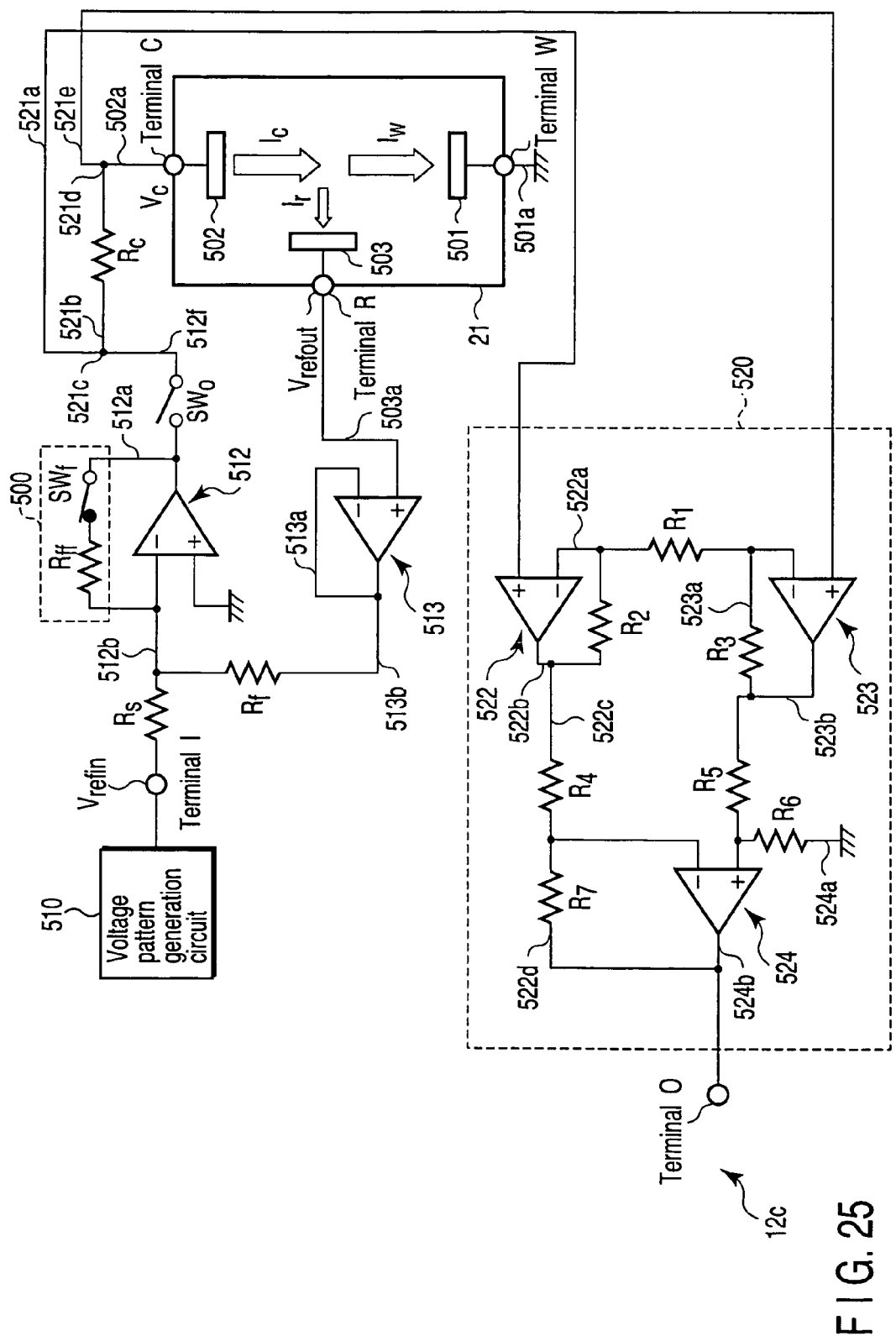
FIG. 25 is a view showing another modification of the potentiostat according to the first embodiment.
Figure 27:
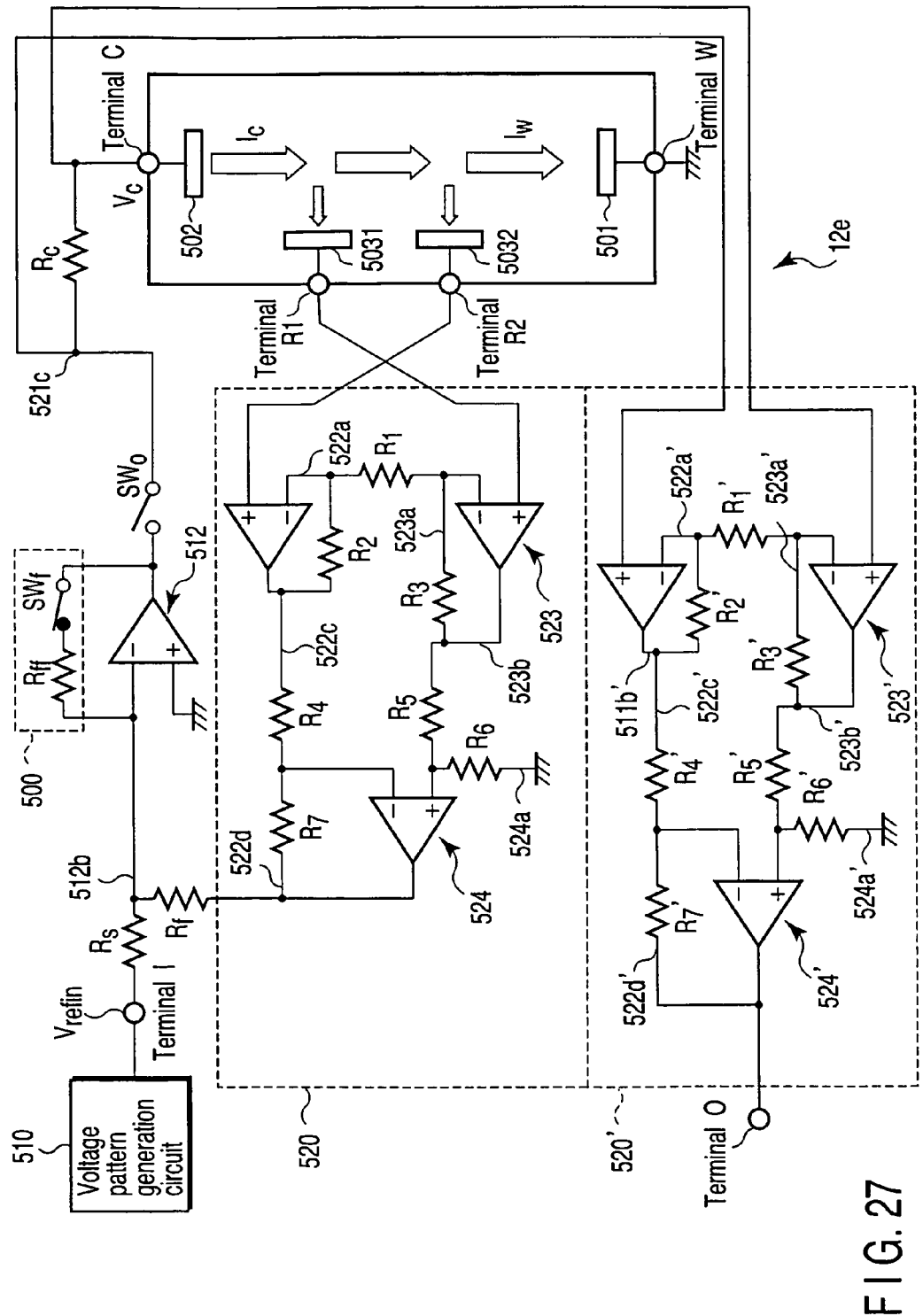
FIG. 27 is a view showing still another modification of the potentiostat according to the first embodiment.

Modifications of the potentiostat 12a serving as the measurement system 12 shown in FIG. 19 are shown in FIGS. 24 to 27. FIGS. 24 and 25 show examples in which a 3-electrode potentiostat is used as the measurement system 12. FIGS. 26 and 27 show examples in which a 4-electrode potentiostat is used as the measurement system 12.

The basic arrangement of a potentiostat 12b shown in FIG. 24 is the same as that of the potentiostat 12a shown in FIG. 19. The same reference numerals denote the same parts, and a detailed description thereof will be omitted. The potentiostat 12b is different from the potentiostat 12a in that the protective circuit 500 is not arranged, including the wiring line 512a. In place of the protective circuit 500, a resistance $R_c$ is arranged in the wiring line 502a. When the resistance $R_c$ is connected in series with the output from the inverting amplifier 512 on the side of the counter electrode 502, the voltage applied to the counter electrode exhibits a first-order delay due to the double layer capacitance. Accordingly, the influence on the biochemical solution in the cell 115 can be reduced.

The arrangement of a potentiostat 12c shown in FIG. 25 is slightly different from those of the potentiostats 12a and 12b. In the potentiostat 12c, the current detection resistance $R_c$ is arranged on the side of the counter electrode 502. A detected current is converted into a voltage by a high-input impedance differential amplifier 520. The arrangement will be described below in more detail.

As shown in FIG. 25, the voltage pattern generation circuit 510 which generates a voltage pattern to detect a current between the electrodes is connected to the inverting input terminal of the inverting amplifier 512 ($OP_c$) through the wiring line 512b. The resistance $R_s$ is connected to the wiring line 512b. The non-inverting input terminal of the inverting amplifier 512 is grounded. A wiring line 512f is connected to the output terminal. The output terminal and inverting input terminal of the inverting amplifier 512 are connected by the protective circuit 500.

The wiring line 512f has the switch $SW_0$ which ON/OFF-controls voltage application to the terminal C. The wiring line 512f is branched to two wiring lines 521a and 521b at an intersection 512c. The wiring line 521a is connected to the non-inverting input terminal of an amplifier 522 in the high-input impedance differential amplifier 520.

The wiring line 521b has the current detection resistance $R_C$. The wiring line 521b is branched to the wiring line 502a and a wiring line 521e at an intersection 521d. The wiring line 502a is connected to the terminal C. The wiring line 521e is connected to the non-inverting input terminal of an amplifier 523 in the high-input impedance differential amplifier 520.

The arrangement of the voltage follower amplifier 513, wiring lines 513a and 513b, and resistance $R_f$, which feeds back a voltage from the terminal R on the side of the reference electrode 503 to the inverting input terminal of the inverting amplifier 512, is the same as in FIG. 19.

The terminal W on the side of the working electrode 501 is grounded through the wiring line 501a.

The high-input impedance differential amplifier 520 amplifies the differential voltage between the output from the wiring line 521a without intervening the current detection resistance $R_c$ and the output from the wiring line 521e through the current detection resistance $R_c$ and outputs the differential voltage to the terminal O. The inverting input terminals of the amplifiers 522 and 523 are connected by a wiring line 522a having a resistance $R_1$. The inverting input terminal and output terminal of the amplifier 522 are connected by a wiring line 522b having a resistance $R_2$. The inverting input terminal and output terminal of the amplifier 523 are connected by a wiring line 523a having a resistance $R_3$. The output from the amplifier 522 is connected to the inverting input terminal of an amplifier 524 through a resistance $R_4$. The output from the amplifier 523 is connected to the non-inverting input terminal of an amplifier 525 through a resistance $R_5$. The amplifier 524 is grounded through a resistance $R_6$. The inverting input terminal and output terminal of the amplifier 524 are connected by a wiring line 522d having a resistance $R_7$. The output terminal of the amplifier 524 is connected to the terminal O by a wiring line 524b.

In the potentiostat 12c, an oxidation current is detected not from the working electrode 501 but from the counter electrode 502.

As described above, even when the potentiostat 12c shown in FIG. 25 is used, the same effect as that of the potentiostat 12a can be obtained.

The arrangements on the side of the counter electrode 502 and on the side of the working electrode 501 of a 4-electrode potentiostat 12d shown in FIG. 26 are the same as those of the potentiostat 12a shown in FIG. 19. In the potentiostat 12d, the voltages from two reference electrodes 5031 and 5032 are differentially amplified by using the high-input impedance differential amplifier 520. The differential amplified voltage is fed back to the inverting amplifier 512 on the side of the counter electrode 502. In this way, the potential difference between the two reference electrodes is detected. The supply current from the counter electrode 502 is controlled such that the value of the potential difference has a predetermined voltage characteristic.

As shown in FIG. 26, a terminal $R_1$ on the side of the reference electrode 5031 is connected to the non-inverting input terminal of the amplifier 523. A terminal $R_2$ on the side of the reference electrode 5032 is connected to the non-inverting input terminal of the amplifier 522. The high-input impedance differential amplifier 520 differentially amplifies the two voltage of the non-inverting input terminals of the amplifiers 522 and 523 and outputs the differential voltage. The output side of the high-input impedance differential amplifier 520 is connected to the wiring line 512b through the resistance $R_f$.

As described above, even when the potentiostat 12d shown in FIG. 26 is used, the same effect as that of the potentiostat 12a can be obtained.

The basic arrangement of a 4-electrode potentiostat 12e shown in FIG. 27 is the same as that of the potentiostat 12c shown in FIG. 25. The difference from the potentiostat 12c is that the potentiostat 12e has two reference electrode extraction voltages, and the two voltages are differentially amplified and fed back to the side of the counter electrode 502. The arrangements on the side of the counter electrode 502 and on the side of the working electrode 501 are the same as those of the potentiostat 12c, and a detailed description thereof will be omitted. Reference numeral 520' denotes a high-input impedance differential amplifier that has the same arrangement as the above-described high-input impedance differential amplifier 520.

As shown in FIG. 27, in the potentiostat 12e, the outputs from the terminal $R_1$ on the side of the reference electrode 5031 and the terminal $R_2$ on the side of the reference electrode 5032 are respectively connected to the non-inverting input terminal of the amplifier 523 and the non-inverting input terminal of the amplifier 522. As described above, the high-input impedance differential amplifier 520 differentially amplifies the two inputs and outputs the differential voltage. The resistance $R_f$ is connected to the output side. The high-input impedance differential amplifier 520 is connected to the wiring line 512b through the resistance $R_f$. With this structure, the output from the high-input impedance differential amplifier 520 is fed back to the input side of the inverting amplifier 512.

FIG. 28 is a block diagram showing the association between the control mechanism 15 and the remaining constituent elements of the computer 16. As shown in FIG. 28, the computer 16 comprises a main processor 16a and an interface 16b. Data can be transmitted/received to/from the plurality of control mechanisms 15 via the interface 16b through a local bus 17. The control mechanism 15 comprises a measurement control mechanism main body 15a and a data memory 15b which stores data to be handled by the measurement control mechanism main body 15a. One control mechanism 15 is arranged in correspondence with each measurement unit 10. As the plurality of connected measurement units 10 are connected to one main processor 16a, the load on the main processor 16a can be reduced.

Figure 29:
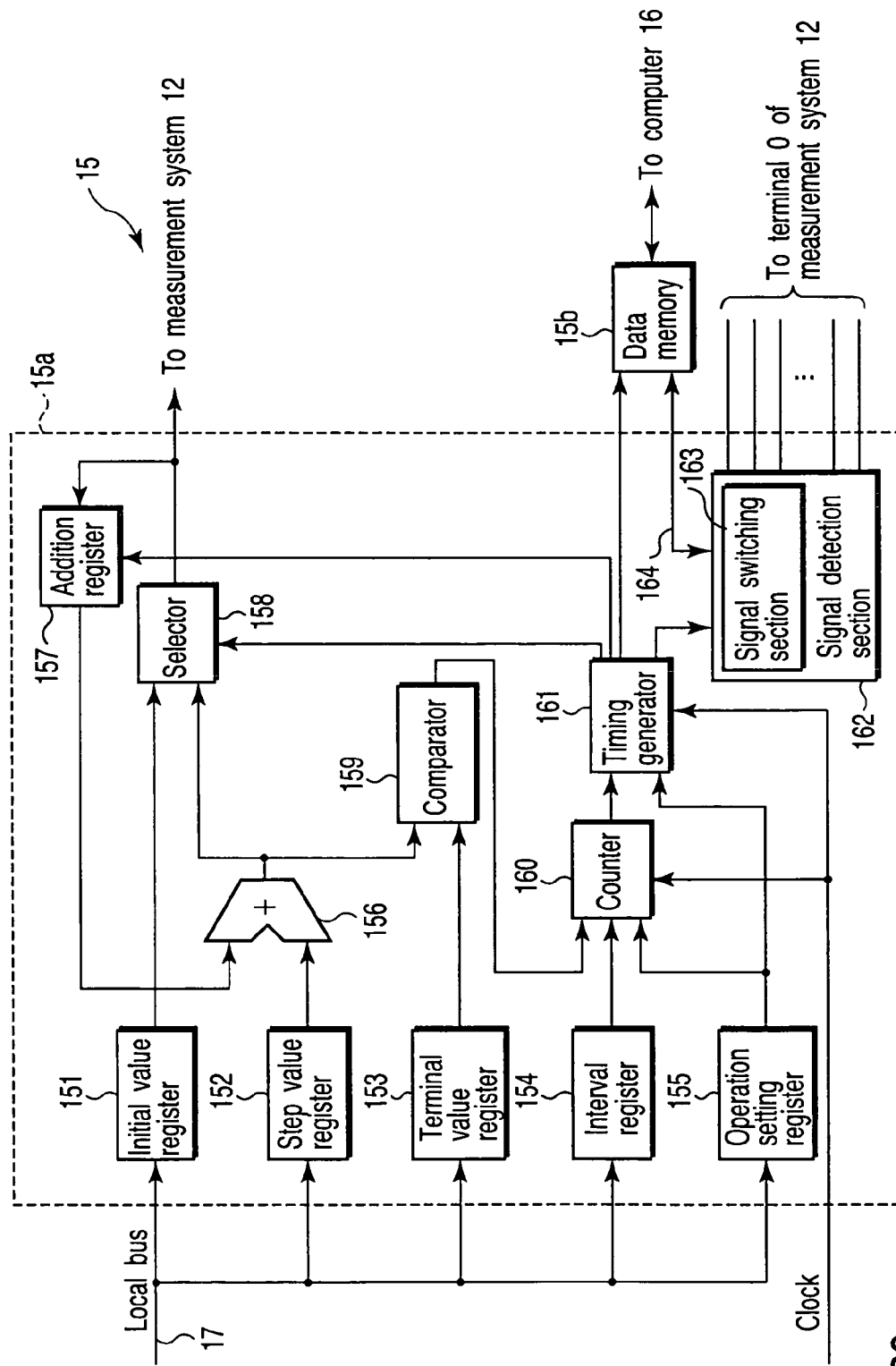
FIG. 29 is a block diagram showing a detailed arrangement of the control mechanism according to the first embodiment.

FIG. 29 is a block diagram showing a detailed arrangement of the control mechanism 15. As shown in FIG. 29, the measurement control mechanism main body 15a has an initial value register 151, step value register 152, terminal value register 153, interval register 154, and operation setting register 155, which are connected to the local bus 17.

The initial value register 151, step value register 152, terminal value register 153, interval register 154, and operation setting register 155 store an initial value, step value, terminal value, measurement time interval, and operation mode, respectively, which can be set by the main processor 16a. When an initial value, step value, terminal value, measurement time interval, and operation mode are set, a data measurement operation is started.

The initial value, step value, and terminal value represent a value corresponding to the voltage value of a voltage pattern to be generated by the voltage pattern generation circuit 510. A voltage pattern is set as a digital value from the initial value to the terminal value for every step value. For example, assume that a voltage pattern having a predetermined waveform is to be generated from times $t_1$ to $t_5$. The voltage value at time $t_1$ corresponds to the initial value. The voltage value varies by the step value from time $t_1$ at a measurement time interval $\Delta t$. Such a voltage value changes stepwise to the terminal value.

Only at the start of measurement, a selector 158 selectively outputs the initial value from the output value from the initial value register and the output value from an adder 156. From the next data, the selector 158 selectively outputs the sum from the adder 156. The output value from the selector 158 is output to the voltage pattern generation circuit 510 of the measurement system 12 in synchronism with the output signal from a timing generator 161. The voltage pattern generation circuit 510 generates a voltage having a voltage value corresponding to the output value from the selector 158. With this operation, a voltage pattern having the voltage waveform shown in FIG. 21A described above can be generated.

An adding register 157 temporarily stores the output value from the selector 158 in synchronism with the output signal from the timing generator 161.

The adder 156 adds the step value from the step value register 152 to the initial value from the initial value register 151 and outputs the sum to the selector 158 and a comparator 159. The value stored in the adding register 157 corresponds to the voltage value to be output to the measurement system 12. Hence, the adder 156 outputs a value corresponding to a voltage value as the sum of the step value and the output voltage value to the measurement system 12. The comparator 159 compares the sum from the adder 156 with the terminal value from the terminal value register 153. When the sum exceeds the terminal value, the comparator 159 outputs a signal representing the end of count to a counter 160.

The counter 160 counts clocks on the basis of the operation setting mode from the operation setting register 155 for a period defined by the measurement time interval from the interval register 154. The counter 160 continues counting until the count end signal is input from the comparator 159.

As the operation setting mode, a single measurement mode, 4-electrode setting mode, 8-electrode setting mode, or the like can be set in accordance with, e.g., the number of working electrodes to be measured simultaneously. When, e.g., the single measurement mode is set, the counter 160 executes counting for the period defined by the measurement time interval and outputs the count value to the timing generator 161. When the 4-electrode setting mode is set, the counter 160 executes counting for each of periods obtained by dividing the measurement time interval into four parts and outputs the count value to the timing gene rator 161. As described above, when a multiple electrode setting mode is set, counting is executed for each of periods obtained by dividing the measurement time interval into parts equal in number to the electrodes.

The timing generator 161 outputs an address signal and write signal to the data memory 15b in synchronism with the output timing of the count value from the counter 160 while counting the clocks. The timing generator 161 also switches a signal switching section 163 of a signal detection section 162 in accordance with the operation setting mode from the operation setting register 155.

The signal switching section 163 is connected to the terminals O of the plurality of working electrodes 501 of the measurement system 12. In the plurality of working electrodes 501, electrochemical signals by an intercalating agent can be simultaneously detected for the terminals O. With the signal switching section 163, one of the electrochemical signals from the plurality of working electrodes 501 can selectively be detected.

The signal detection section 162 A/D-converts the electrochemical signal from the working electrode 501 switched by the signal switching section 163 controlled by the timing generator 161 and outputs the electrochemical signal to the data memory 15b through a data bus 164. Accordingly, every time a write signal from the timing generator 161 is input, data from the data bus 164 can sequentially be written in the data memory 15b at an address position given by each write signal.

In, e.g., the single electrode setting mode, when the measurement time interval is 10 msec, a write signal and an address are output from the timing generator 161 to the data memory 15b once in a period of 10 msec. In addition, the digital conversion value of an electrochemical signal is output from the signal detection section 162 to the data memory 15b through the data bus 15b.

In the 4-electrode setting mode, when the measurement time interval is 10 msec, a write signal and four addresses are output from the timing generator 161 to the data memory 15b four times in a period of 10 msec. In addition, the digital conversion values of the four electrochemical signals are sequentially output from the signal detection section 162 to the data memory 15b through the data bus 15b. Accordingly, the electrochemical signals that are almost simultaneously detected at the measurement time interval can be stored as data.

To increase the accuracy of measurement, in the multiple electrode setting mode, the signal detection timing from the plurality of working electrodes 501 may be shortened without synchronizing the detection timing with the timing obtained by equally dividing the measurement time interval. For example, when a plurality of switching signals of the signal switching section 163 are generated in a short time in the measurement time interval, a measurement accuracy independently of the measurement time interval can be maintained. For example, when the measurement time interval is 10 msec, no switching signal is generated during initial 9 msec. The timing generator 161 is programmed such that switching signals are generated in 1 msec between the timing corresponding to 9 msec and that corresponding to 10 msec and output to the signal switching section 163. With this setting, electrochemical signals from the four working electrodes 501 can be detected within 1 msec. Hence, even when a long measurement time interval is set, no variation in measurement time interval is generated, and a high accuracy can be maintained.

The measurement data stored in the data memory 15b are read out by the main processor 16a of the computer 16 and used for various kinds of signal analysis.

As described above, when a plurality of measured electrochemical signals are switched and selectively detected at a shorter interval than the measurement time interval set by the timing generator 161, the signals of the working electrodes 501 can be almost simultaneously measured.

One example of a measurement data analyzing method of causing the computer 16 to execute signal analysis on the basis of measurement data will be described next. A type determination analyzing method which determines whether the base at the SNP position of a target DNA is G type (homo type), T-type (homo type), or GT-type (hetero type) will be described here with reference to the flow chart shown in FIG. 30. Although not particularly illustrated in FIG. 1 or 28, the main processor 16a of the computer 16 executes an analysis program comprising a plurality of commands for type determination filtering, type determination processing, and determination result output, thereby executing type determination filtering, type determination processing, and determination result output. In addition, for control of the above-described control mechanism 15, a control program is separately prepared. The analysis program or control program may be executed by causing a recording medium reading device arranged in the computer 16 to read out the analysis program stored in a recording medium. Alternatively, the program may be read out from a storage device such as a magnetic disk provided in the computer 16 and executed.

As a presupposition of measurement data analysis, four types of target base sequences, which have A, G, C, and T as bases at SNP positions, are prepared as objects to be detected. A plurality of target complementary DNA probes, which have base sequences complementary to the target base sequences, are immobilized to the working electrodes 501 in correspondence with the respective types. In addition, a plurality of DNA probes (to be referred to as negative control hereinafter) having base sequences different from those of the four target complementary DNA probes are immobilized to other working electrodes 501 (s61). Note that DNA probes of one kind are fixed to the working electrodes 501 in principle.

A sample containing the specimen DNA probe is injected into the base sequence detection chip on which the above-described target complementary DNA probes are fixed. A hybridization reaction is caused (s62). Cleaning by a buffer and an electrochemical reaction by introduction of an intercalating agent are executed. Then, a representative current value is calculated using the measurement system 12 (s63).

The representative current value indicates a numerical value that is effective for quantitatively grasping occurrence of hybridization reactions of the respective DNA probes. For example, the maximum value (peak current value) of the current value of a detected signal corresponding to the representative current value. The peak current value is derived by measuring an oxidation current signal from an intercalating agent which is bonded to double stranded DNA hybridized to the DNA probe immobilized to each working electrode 501 and obtaining the peak of the current value. The peak current value is preferably detected by subtracting a background current except the oxidation current signal from the intercalating agent.

Any other value may be defined as the representative current value in accordance with the accuracy or object of signal processing. For example, the integral value of oxidation current signals can be used. Not a current value but a voltage value or a value obtained by executing numerical value analysis processing for the current or voltage may be defined as the representative current value.

Measurement data, i.e., representative current values related to the target DNA with A, G, C, and T as bases at the SNP positions are defined as $X_a$, $X_g$, $X_c$, and $X_t$. The representative current value of the DNA probe of negative control is defined as $X_n$. A plurality of representative current values are obtained for each type. To identify the representative current values, first $X_a$ is defined as $X_{a1}$, second $X_a$ is defined as $X_{a2}$, . . . .

The numbers of representative current values obtained for the target DNA with A, G, C, and T as bases at the SNP positions are defined as $n_a$, $n_g$, $n_c$, and $n_t$. The number of representative current values obtained for negative control is defined as $n_n$.

Next, to remove clearly abnormal data from the obtained representative current values $X_a$, $X_g$, $X_c$, $X_t$, and $X_n$, type determination filtering processing is executed (s64).

Figure 31:
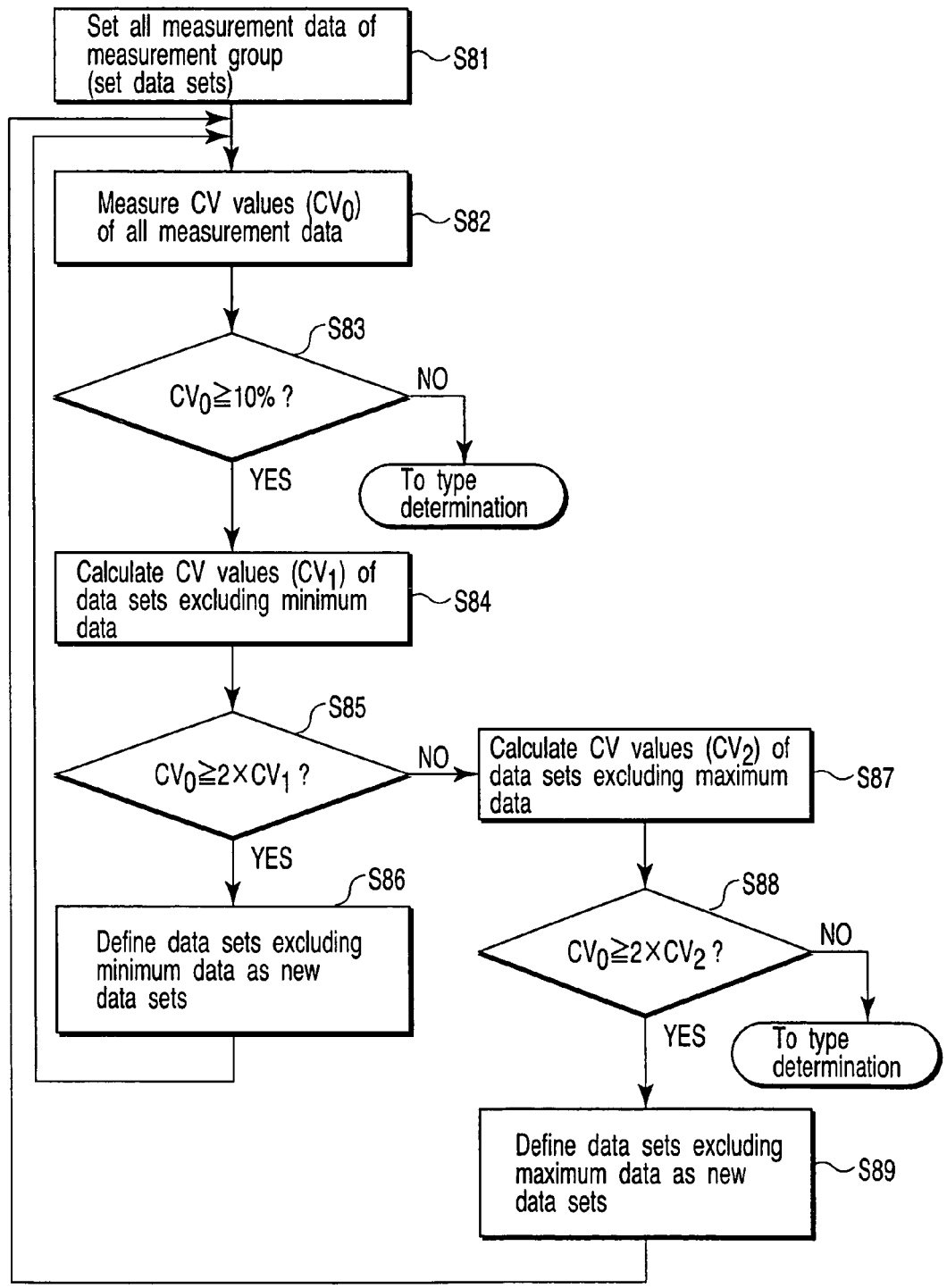
FIG. 31 is a flow chart of type determination filtering processing according to the first embodiment.

FIG. 31 is a flow chart of type determination filtering processing. The type determination filtering processing shown in FIG. 31 is executed for each of $X_a$, $X_g$, $X_c$, $X_t$, and $X_n$. For, e.g., $X_a$, representative current values that are supposed to be clearly abnormal are excluded from the $n_a$ representative current values obtained for $X_a$ by the type determination filtering. The same processing is executed even for $X_g$, $X_c$, $X_t$, and $X_n$.

In the description of FIG. 31, the same processing is executed in accordance with the data type. Filtering for $X_a$ will be exemplified.

More specifically, as shown in FIG. 31, all measurement data of each measurement group are set. That is, data sets are set (s81). For, e.g., $X_a$, $X_{a1}$, $X_{a2}$, . . . , $X_{ana}$ are set as data sets.

Next, a CV value (to be referred to as a value $CV_0$ hereinafter) for the measurement data $X_{a1}$, $X_{a2}$, . . . , $X_{ana}$ is calculated (s82). The value $CV_0$ is obtained by dividing the standard deviation of the measurement data $X_{a1}$, $X_{a2}$, . . . , $X_{ana}$ by the average value. It is determined whether the obtained value $CV_0$ is 10%, i.e. 0.1 or more (s83).

If the value $CV_0$ is 10% or more, a CV value (to be referred to as a value $CV_1$ hereinafter) of (na−1) data sets, excluding the minimum value of the measurement data, is calculated (s84). If the value $CV_0$ is less than 10%, it is determined that no data is clearly abnormal, and the flow advances to type determination (to be described later).

After $CV_1$ is calculated, it is determined whether $CV_0 \geq 2 \times CV_1$ (s85). When this inequality holds, the flow advances to (s86) to newly define (na−2) data sets, excluding the minimum value of the measurement data. The flow returns to (s82) to repeatedly execute abnormal data filtering.

When the inequality does not hold, it is determined that abnormal data is present not on the minimum value side but on the maximum value side. A CV value (to be referred to as a value $CV_2$ hereinafter) of (na−2) data sets, excluding the maximum value of the measurement data, is calculated (s87). It is determined whether $CV_0 \geq 2 \times CV_2$ (s88). When this inequality holds, (na−3) data sets, excluding the maximum value of the measurement data, are newly set as data sets. The flow returns to (s82) to repeatedly execute abnormal data filtering. If the inequality does not hold, it is determined that no data is clearly abnormal, and the flow advances to type determination (to be described later).

The above-described type determination filtering is executed even for $X_g$, $X_c$, $X_t$, and $X_n$.

Next, type determination processing is executed using the obtained type determination filtering result (s65). An example of the type determination processing will be described with reference to the flow chart shown in FIG. 32. In the example shown in FIG. 32, type determination is performed to determine whether the base at the SNP position of target DNA is G type, T type, or GT type. This type determination processing is roughly divided into a maximum group determination algorithm and a 2-sample t-test algorithm.

Figure 32:
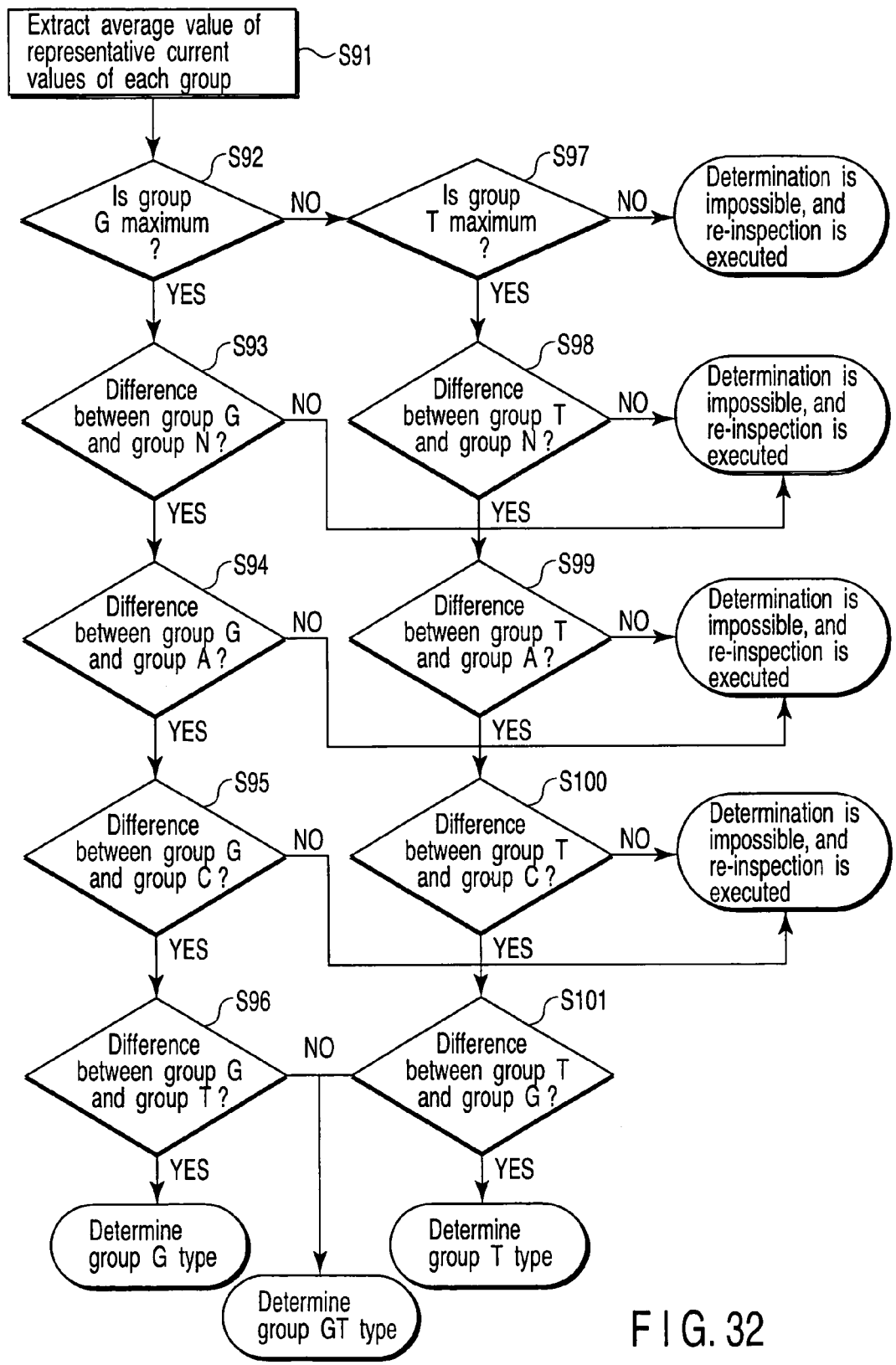
FIG. 32 is a flow chart showing an example of type determination processing according to the first embodiment.

As shown in FIG. 32, first, the average value of the representative current values of each group is extracted (s91). The groups are $X_a$, $X_g$, $X_c$, $X_t$, and $X_n$. That is, DNA probes with different target base sequences are put into different groups, and DNA probes having the same target base sequence are input into the same group. In (s64), measurement data excluding clearly abnormal data are extracted by type determination filtering. Measurement data excluding abnormal data may be extracted by filtering except the type determination filtering in (s64). Measurement data may be extracted without executing any filtering. Instead of the average value of the representative current values, another statistical processing value may be obtained by statistical processing of the statistical values.

Groups which have A, G, C, and T as bases at the SNP position of target DNA are defined as groups A to T. A group for negative control is defined as a group N. The obtained average values for the groups $X_a$, $X_g$, $X_c$, $X_t$, and $X_n$ are defined as $M_a$, $M_g$, $M_c$, $M_t$, and $M_n$, respectively.

For the obtained average values $M_a$, $M_g$, $M_c$, $M_t$, and $M_n$, it is determined whether the average value $M_g$ of the group G is maximum (s92). If $M_g$ is maximum, the flow advance to (s93). If $M_g$ is not maximum, the flow advances to (s97).

In (s97), for the average values $M_a$, $M_g$, $M_c$, $M_t$, and $M_n$, it is determined whether the average value $M_t$ of the group T is maximum. If $M_t$ is maximum, the flow advance to (s99). If $M_t$ is not maximum, neither the groups G and T are maximum. Since determination is impossible, re-inspection is executed.

In (s93), it is determined whether a difference is present between the measurement data $X_{g1}$, $X_{g2}$, . . . of the group G and the measurement data $X_{n1}$, $X_{n2}$, . . . of the group N. To determine whether a difference is present, for example, 2-sample t-test is used. More specifically, a probability P and a significance level α obtained by 2-sample t-test are compared as the representative relationship.

H0: when P≧α, no significant difference is present (null hypothesis)

H1: when P<α, a significant difference is present (alternative hypothesis)

The significance level α can be set by the user using the computer 16. In the example of (s93), a question for H1, i.e., whether a difference is present between the measurement data of the group G and that of the group N is raised. For this question, the hypothesis H1 that no difference is present between the two groups is set. The probability is obtained assuming that the difference between the two groups is summarized in the average value $M_g$ of the group G and the average value $M_n$ of the group N. To calculate the probability, a statistical constant t and a degree of freedom φ are calculated on the basis of the statistical values $X_{g1}$, $X_{g2}$, . . . of the group G and the statistical values $X_{n1}$, $X_{n2}$, . . . of the group N. The probability P is obtained from the integral value of the probability density variables of the t-distribution.

For the obtained probability P, when P≧α, H0 cannot be discarded, and determination is retained. That is, it is determined that no difference is present. When P<α, H0 is discarded, and the hypothesis H1 is employed. It is determined that a difference is present.

When it is determined that "a difference is present", the flow advances to (s94). When it is determined that "no difference is present", determination is impossible, and re-inspection is executed.

In (s94), for the group G and group A, it is determined using the same 2-sample t-test as in (s93) whether a difference is present between the two groups. If a difference is present, the flow advances to (s95). If no difference is present, determination is impossible, and re-inspection is executed.

In (s95), for the group G and group C, it is determined using the same 2-sample t-test as in (s93) whether a difference is present between the two groups. If a difference is present, the flow advances to (s96). If no difference is present, determination is impossible, and re-inspection is executed.

In (s96), for the group G and group T, it is determined using the same 2-sample t-test as in (s93) whether a difference is present between the two groups. If a difference is present, the group G type is determined. This is because the group G type has the maximum average value and differences to the remaining measurement groups. If no difference is present, the group GT type is determined. This is because the group G type has the maximum average value though the measurement result of the group G type and that of the group T type have no difference.

In (s98), for the group T and group N, it is determined using the same 2-sample t-test as in (s93) whether a difference is present between the two groups. If a difference is present, the flow advances to (s99). If no difference is present, determination is impossible, and re-inspection is executed.

In (s99), for the group T and group A, it is determined using the same 2-sample t-test as in (s93) whether a difference is present between the two groups. If a difference is present, the flow advances to (s100). If no difference is present, determination is impossible, and re-inspection is executed.

In (s100), for the group T and group C, it is determined using the same 2-sample t-test as in (s93) whether a difference is present between the two groups. If a difference is present, the flow advances to (s101). If no difference is present, determination is impossible, and re-inspection is executed.

In (s101), for the group T and group G, it is determined using the same 2-sample t-test as in (s93) whether a difference is present between the two groups. If a difference is present, the group T type is determined. This is because the group T type has the maximum average value and differences to the remaining measurement groups. If no difference is present, the group GT type is determined. This is because the group T type has the maximum average value though the measurement result of the group T type and that of the group G type have no difference.

The above determination results are displayed on a display apparatus (not shown) arranged in the computer 16 (s66). When the above type determination algorithm is used, a hetero type can be determined.

Figure 30:
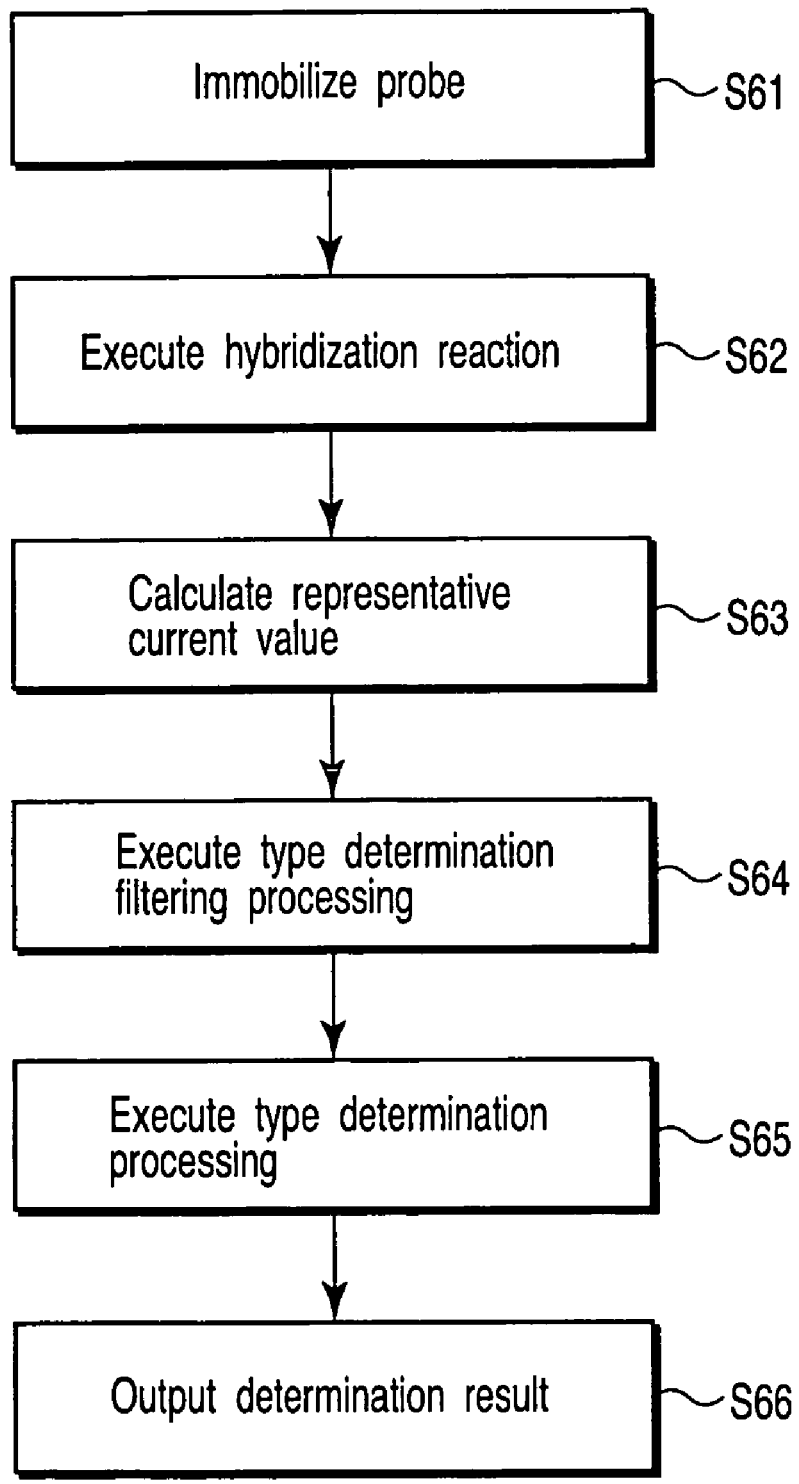
FIG. 30 is a flow chart showing an example of a measurement data analyzing method according to the first embodiment.

FIGS. 30 to 32 show a method of determining whether the type corresponds to the G type, T type, or GT type. This method can also be applied to determine two of the A type, G type, C type, and T type or determine a hetero type thereof. In addition, measurement data need not always be acquired for the four types of groups, i.e., A type, G type, C type, and T type. For example, measurement data may be acquired for only two groups related to two considerable bases of SNP. In addition, one group for negative control may be added to the two groups.

A base sequence automatic analyzing method using the above-described base sequence detection apparatus will be described with reference to the sequence chart shown in FIG. 33.

Figure 33:
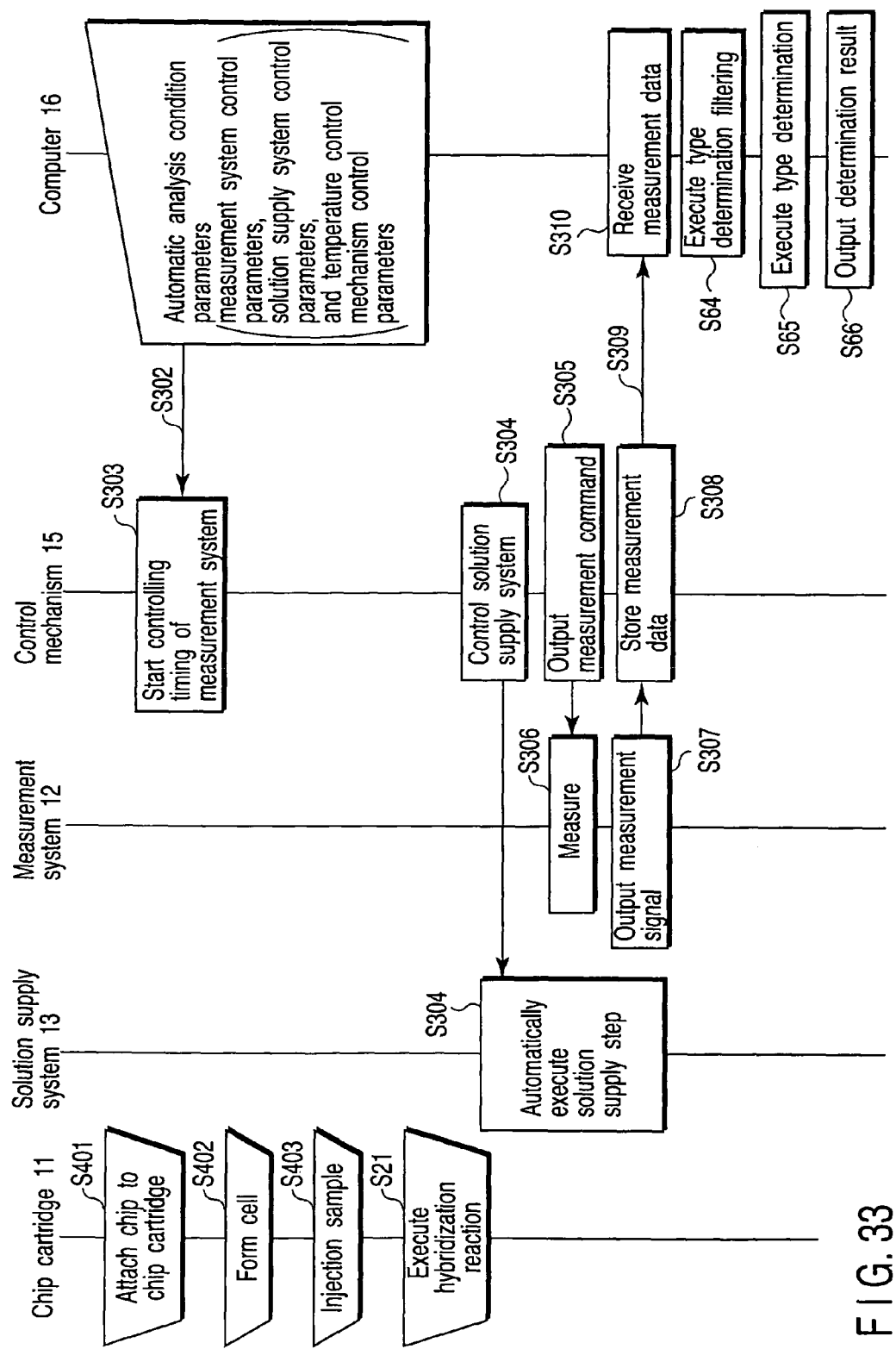
FIG. 33 is a sequence chart of a base sequence automatic analyzing method using the base sequence detection apparatus according to the first embodiment.

As shown in FIG. 33, first, automatic analysis condition parameters for automatic analysis are set by using the computer 16. The user instructs the computer 16 to execute automatic analysis based on the set automatic analysis condition parameters (s301). The automatic analysis condition parameters are control parameters used to control the control mechanism 15. The control parameters used in the control mechanism 15 include measurement system control parameters used to control the measurement system 12, solution supply system control parameters used to control the solution supply system 13, and temperature control mechanism control parameters used to control the temperature control mechanism 14.

The measurement system control parameters are input setting parameters stored in the above-described initial value register 151, step value register 152, terminal value register 153, interval register 154, and operation setting register 155 shown in FIG. 29. The input setting parameters comprise the initial value, step value, terminal value, measurement time interval, and operation mode.

The solution supply system control parameters include solenoid valve control parameters used to control the solenoid valves 403, 413, 423, 433, 441, 442, 444, 445, 451, 453, and 463, sensor control parameters used to control the liquid sensors 443 and 447, and a pump control parameter used to control the pump 454. The solenoid valve control parameters, sensor control parameters, and pump control parameter more specifically include the control amounts of objects to be controlled, the control timings of objects to be controlled, and control conditions for controlling objects to be controlled as conditions to sequentially execute the series of processes shown in (s22) to (s36) in FIG. 18.

The temperature control parameters accompany the solution supply system control parameters in principle. More specifically, when the solution supply system control parameters are set, the temperature control parameters are set in correspondence with the operation of the solution supply system 13. Accordingly, temperature control of the temperature control mechanism 14 can be executed in synchronism with the solution supply system 13.

When automatic analysis is executed, the automatic analysis condition parameters are transmitted to the control mechanism 15 (s302). The control mechanism 15 controls the measurement system 12 on the basis of the measurement system control parameters. The control mechanism 15 controls the solution supply system 13 on the basis of the solution supply system control parameters. The control mechanism 15 controls the temperature control mechanism 14 on the basis of the temperature control mechanism control parameters. The control mechanism 15 also manages the control timings of the measurement system 12, solution supply system 13, and temperature control mechanism 14 on the basis of the control timings and control conditions included in the control parameters. Hence, the control sequence is freely defined in accordance with the automatic analysis condition parameters set by the user. In FIG. 33, a typical example will be described.

Independently from the automatic analysis, the user prepares the chip cartridge 11. First, desired DNA probes are immobilized to the working electrodes 501 of the base sequence detection chip 21. The printed board 22 in which the base sequence detection chip 21 is encapsulated is fixed to the support body 111 of the chip cartridge 11 with the board fixing screws 25 and thus attached to the chip cartridge 11

(s401). The chip cartridge top cover 112 having the sealing member 24a integrated and the support body 111 are fixed using the top cover fixing screw 117 to form the cell 115. The chip cartridge 11 in this state is prepared (s402). A sample is injected into the chip cartridge 11 through the sample injection port 119 (s403). When the chip cartridge 11 is attached to the apparatus main body, and a start operation is executed, a hybridization reaction (s21) starts. The amount of the sample injected is preferably slightly larger than the volume of the cell 115. In this case, the cell 115 can be completely filled with the sample without any remaining air.

The control mechanism 15 starts controlling the timing of the measurement system on the basis of the measurement system control parameters received from the computer 16 (s303).

The control mechanism 15 also sequentially controls the constituent elements of the solution supply system 13 on the basis of the solution supply system control parameters received from the computer 16 (s304). Although not particularly illustrated in FIG. 33, temperature control of the temperature control mechanism 14 is executed on the basis of the temperature control mechanism control parameters in synchronism with the control of the solution supply system 13. By this control, the solution supply system 13 automatically executes the solution supply step shown in (s21) to (s36) (except s34) in FIG. 18, including the hybridization reaction (s305). In addition, the temperature control mechanism 14 is automatically controlled such that the base sequence detection chip 21 is set to the temperature designated in the solution supply step.

The control mechanism 15 sends a measurement command to the measurement system 12 in synchronism with the timing of the measurement step (s34) in the solution supply step (s305). More specifically, at the timing of the measurement step (s34) in the solution supply step, the initial value, step value, terminal value, measurement time interval, and operation setting mode are stored in the initial value register 151, step value register 152, terminal value register 153, interval register 154, and operation setting register 155. The above-described measurement system timing control (s303) may be executed simultaneously with (s305).

The measurement system 12 executes measurement by generating, e.g., a voltage pattern on the basis of the measurement command (s306). The obtained measurement signal is output from the terminal O to the control mechanism 15 (s307). The control mechanism 15 processes the received measurement signal and stores it in the data memory 15b as measurement data (s308). The measurement data is output to the computer 16 through the local bus 17 (s309). The computer 16 receives the measurement data (s310).

When the necessary measurement data is obtained, the computer 16 executes type determination filtering in (s64) shown in FIG. 31 on the basis of the measurement data. When type determination filtering is ended, type determination processing shown in FIG. 32 is executed on the filtered data (s65). Finally, the obtained determination result is displayed on the display apparatus of the computer 16 (s66).

As described above, according to this embodiment, a uniform reaction environment is obtained for the 3-electrode system comprising a working electrode, counter electrode, and reference electrode. For this reason, the flow velocity of a biochemical solution is constant on the electrodes. The uniformity of the electrochemical reaction in the channels increases. As a result, the reliability of the detection result increases. In addition, when the counter electrode and reference electrode are arranged on planes different from that of the working electrode, the layout density of the working electrodes can be increased. Furthermore, when DNA probes are to be immobilized to the working electrodes 501, the counter electrode 502 or reference electrode 503 is not contaminated.

In addition, after the specimen DNA solution is injected into the chip cartridge 11, the whole process from hybridization to cleaning of nonspecific absorption DNA by a buffer, injection of an intercalating agent, electrochemical measurement, storage of measurement data, and determination of target base sequence based on the measurement data can be automatically executed. Accordingly, the detection signal reproducibility and the detection accuracy can be increased, and the time until result derivation can be shortened.

The present invention is not limited to the above embodiment.

The probe immobilized to the working electrode 501 is a DNA probe in the above embodiment. However, a probe formed from any other nucleic acid except DNA may be used. In addition, any other probe that is not formed from a nucleic acid and has a predetermined base sequence may be used.

The process assignment to the computer 16 and control mechanism 15 is not limited to the above-described example. For example, when each of the measurement system 12, solution supply system 13, and temperature control mechanism 14 has a processor which interprets a command from the computer 16 and executes each constituent element, the control mechanism 15 may be omitted. In this case, the function of the control mechanism 15 shown in FIG. 29 is executed by the computer 16.

As for management of timings of the measurement system 12, solution supply system 13, and temperature control mechanism 14, when each of the measurement system 12, solution supply system 13, and temperature control mechanism 14 has a processor which manages the timing, each process is executed on the basis of the timing managed by the processor. In this case, the computer 16 only needs to transmit automatic analysis condition parameters to the measurement system 12, solution supply system 13, and temperature control mechanism 14 and need not manage the timings.

Alternatively, the computer 16 may execute timing control of the measurement system 12, solution supply system 13, temperature control mechanism 14, and control mechanism 15.

In the above example, the sample injection port 119 communicates with the delivery port 116b. However, the sample injection port 119 may communicate with the introduction port 116a. The working electrode 501 or bonding pad 221 on the base sequence detection chip 21 has a multilayered structure of Ti or Au. However, an electrode or pad made of another material may be used. The layout of the working electrodes 501 is not limited to that shown in FIG. 16. The numbers of working electrodes 501, counter electrodes 502, and reference electrodes 503 are not limited to those illustrated, either.

The solution supply system 13 is not limited to that shown in FIG. 17. For example, when a supply system which supplies a biochemical solution or a gas other than air, milli-Q water, a buffer, and an intercalating agent in accordance with the type of reaction is added, a more complex reaction can be executed in the cell 115. Control of the biochemical solution or air supply path or supply amount between the pipes may be done by a mechanism other than a solenoid valve. The operation of the solution supply system 13 shown in FIG. 18 is merely an example, and various changes and modifications can be made in accordance with the purpose of reaction.

FIGS. 30 to 32 show a case wherein the base sequence automatic analyzing apparatus 1 is used for type determination. However, this is merely an example. The base sequence automatic analyzing apparatus 1 may be used for another analyzing purpose. The automating method shown in FIG. 33 is also merely an example. The automating sequence can also be changed in various ways by changing the arrangements of the chip cartridge 11, measurement system 12, solution supply system 13, temperature control mechanism, and control mechanism 15 in various ways.

The relationship between the base sequence detection chip 21 and the chip cartridge top cover 112 may be reversed.

The layout of the channels 601a to 601d is not limited to that shown in FIG. 5B. For example, the detection channels 601a may be arranged in parallel to a line that connects the cell hole portions 115a and 115b. Each of the channels 601a to 601d may have a curved shape instead of a linear shape. In the above example, the introduction port 116a and delivery port 116b extend perpendicularly to the cell bottom surface. However, the present invention is not limited to this. The introduction port 116a and delivery port 116b may extend in parallel to the cell bottom surface.

Second Embodiment

This embodiment is related to a modification to the first embodiment. This embodiment is related to a modification of the arrangement of the base sequence automatic analyzing apparatus 1 shown in FIG. 1 of the first embodiment. In this embodiment, any arrangement that is not particularly mentioned is the same as in the first embodiment, and a detailed description thereof will be omitted.

Figure 35:
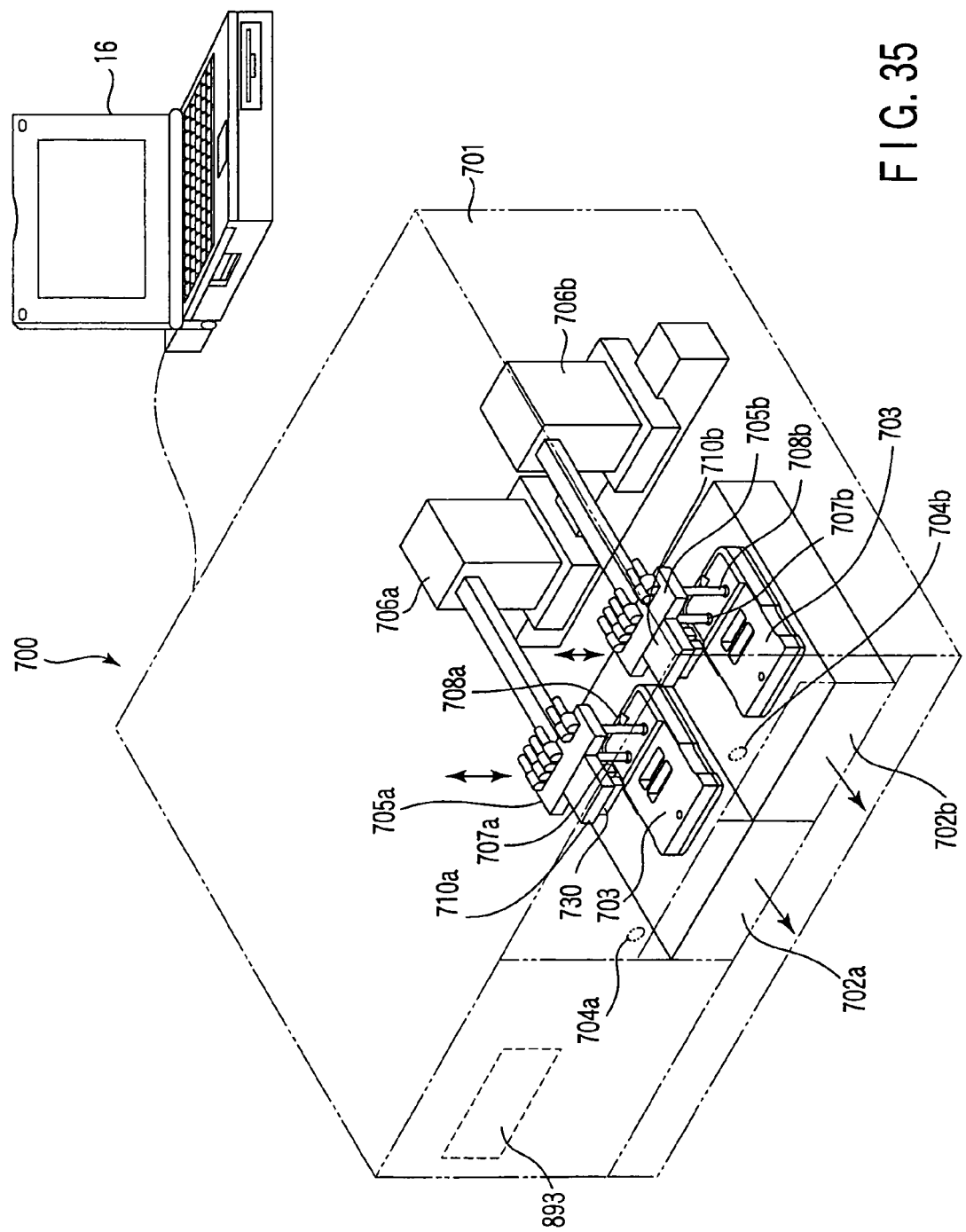
FIG. 35 is a view showing the overall arrangement of a base sequence automatic analyzing apparatus according to the second embodiment of the present invention.

FIG. 35 is a view showing the overall arrangement of a base sequence automatic analyzing apparatus 700 according to this embodiment. The base sequence automatic analyzing apparatus 700 comprises a housing 701 and a computer 16. The housing 701 corresponds to the arrangement of the chip cartridge 11, measurement system 12, solution supply system 13, temperature control mechanism 14, and control mechanism 15 in FIG. 1.

Figure 73:
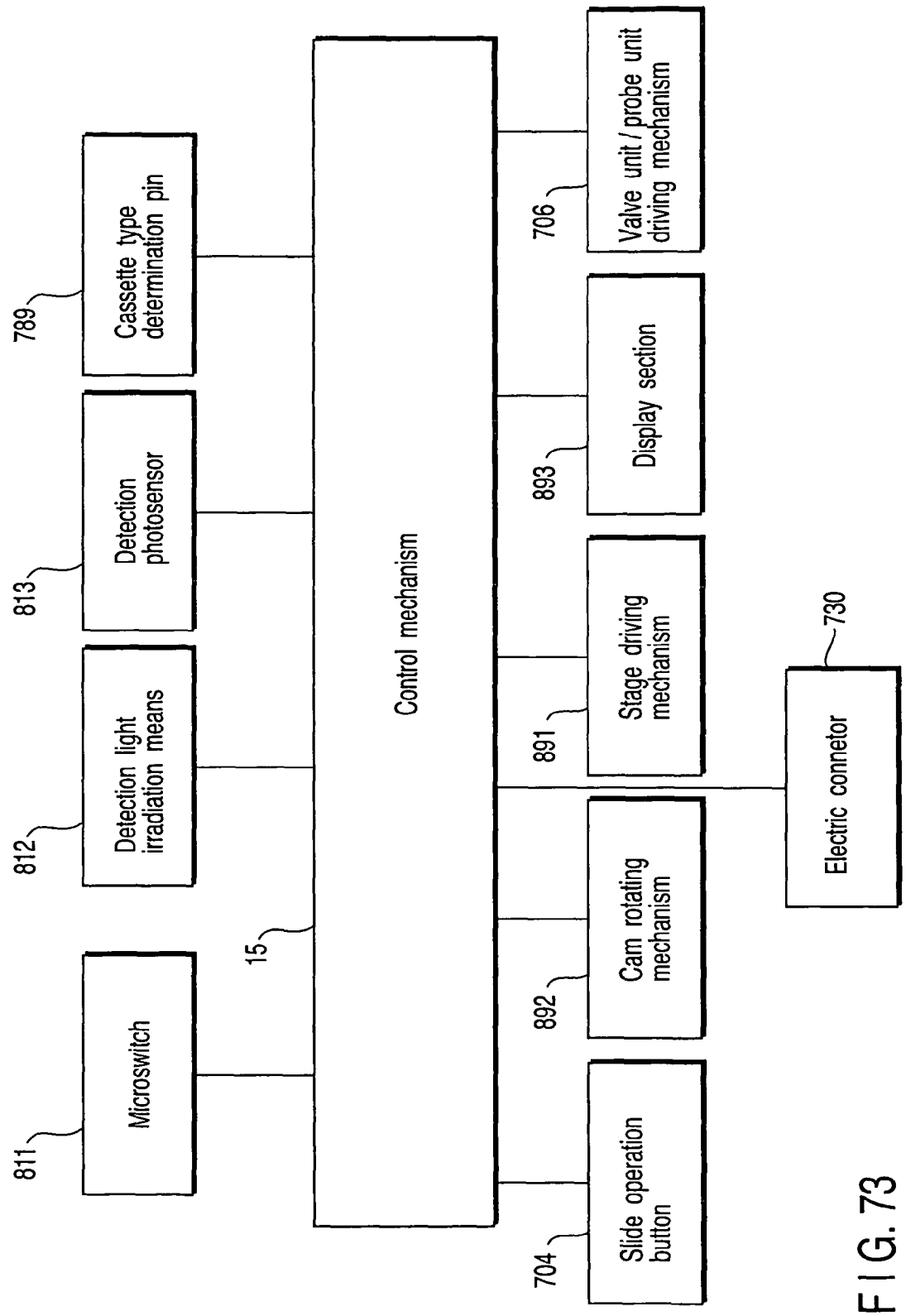
FIG. 73 is a functional block diagram of a control mechanism and the remaining constituent elements according to the second embodiment.

The housing 701 has two slide stages 702a and 702b at predetermined portions on the front surface. Each of the slide stages 702a and 702b has a cassette loading groove 792. When cassettes 703 are set in the cassette loading grooves 792, the cassettes 703 can be positioned and arranged with respect to the slide stages 702a and 702b. More specifically, the slide stages 702a and 702b are designed to slide in the horizontal direction with respect to the housing 701. This slide operation can be done using slide operation buttons 704a and 704b. When one of the slide operation buttons 704a and 704b is pressed, a slide instruction signal is transmitted to a control mechanism 15. Upon receiving the slide instruction signal, the control mechanism 15 can drive a stage driving mechanism 891 (not shown) to slide a corresponding one of the slide stages 702a and 702b. FIG. 73 is a functional block diagram of the control mechanism 15 and its constituent elements.

A display section 893 is arranged at another portion on the front surface of the housing 701. Information detected by the control mechanism 15 can be displayed on the display section 893 on the basis of a command from the control mechanism 15. Examples of detection information are a cassette type, the presence/absence of a cassette, the presence/absence of a seal, the slide stage driving state (tray open/close), the cam rotation state (e.g., the presence/absence of rotation), valve unit/probe unit driving state (e.g., the presence/absence of positioning of a nozzle/electric connector), and the inspection process progress situation.

When the slide operation buttons 704a and 704b are pressed while the slide stages 702a and 702b are kept accommodated in the housing 701, the slide stages 702a and 702b slide from the housing 701 in a direction indicated by arrows in FIG. 35. Accordingly, the cassette loading groove 792 can unload the cassette 703 from the housing 701. Alternatively, the cassette 703 can be set in the cassette loading groove 792.

After the cassettes 703 are set in the cassette loading grooves 792, the slide operation buttons 704a and 704b are pressed. Then, the slide stages 702a and 702b slide in a direction reverse to that of the arrows in FIG. 35 and are accommodated in the housing 701.

In the housing 701, nozzles 707a, 707b, 708a, and 708b are inserted into nozzle insertion holes 722 and 723 of the cassettes 703. In addition, electric connectors 730 are inserted into electric connector ports 724 and 725 so that a base sequence detection operation is executed.

The nozzles 707a and 708a are arranged in a valve unit 705a on the side of the slide stage 702a. The nozzles 707b and 708b are arranged in a valve unit 705b on the side of the slide stage 702b. The electric connectors 730 are arranged in each of probe units 710a and 710b of the slide stages 702a and 702b.

FIGS. 57A and 57B are views showing the structure of the probe unit 710a including the electric connectors 730. FIG. 57A is a perspective view. FIG. 57B is a side view. The two electric connectors 730 are arranged at a predetermined interval on the probe unit 710a made of, e.g., a glass epoxy substrate. At the distal end of each electric connector 730, a plurality of projecting electrodes 730a are laid out in the same matrix as that of pads on a substrate 714. When the projecting electrodes 730a come into contact with the pads on the substrate 714, electrical connection between the substrate 714 and the probe unit 710a is ensured. The electric connector 730 has wires inside. The projecting electrodes 730a and control mechanism 15 are electrically connected by the wires.

FIG. 58 is a side view of the driving system such as the nozzles 707a and 708a and the electric connector 730, and the cassette 703. FIG. 58 mainly shows the arrangement on the side of the slide stage 702a. However, the arrangement on the side of the slide stage 702b is the same as that on the side of the slide stage 702a.

The probe unit 710a is integrated with the valve unit 705a. The valve unit 705a and probe unit 710a are simultaneously driven by a valve unit/probe unit driving mechanism 706a. The valve unit/probe unit driving mechanism 706a drives the valve unit/probe unit in accordance with an instruction from the control mechanism 15. The valve unit/probe unit driving mechanism 706a has two driving directions, i.e., the vertical direction and horizontal direction, as indicated by arrows in FIG. 58. With this structure, the nozzles 707a and 708a and electric connectors 703 move horizontally and downward with respect to the upper portion of the cassette 703 on the side of the slide stage 702a. The nozzles 707a and 708a are positioned to the nozzle insertion holes 722 and 723, and the electric connectors 703 are positioned to the electric connector ports 724 and 725. Similarly, on the side of the slide stage 702b, when a valve unit/probe unit driving mechanism 706b is driven, the nozzles 707b and 708b and electric connectors 703 are positioned to the nozzle insertion holes 722 and 723 and electric connector ports 724 and 725, respectively. Accordingly, the solution supply system and the channel in the cassette 703 communicate. When the electric connectors 730 are positioned to the pads of the cassette 703, the pads and the electric connectors 730 are electrically connected.

In this state, a biochemical solution or the like can be supplied from a solution supply mechanism (not shown) through the nozzles 707a and 707b and discharged through the nozzles 708a and 708b. The electric connectors 730 are also electrically connected to a measurement system 12. When a voltage is applied to the substrate 714 through the electric connectors 730, and a current is detected, electrochemical measurement can be executed. To unload the cassettes 703 from the housing 701, the slide operation buttons 704a and 704b are pressed. Then, the valve unit/probe unit driving mechanisms 706a and 706b drive and move the valve units 705a and 705b upward and then slide the slide stages 702a and 702b in the direction indicated by the arrows in FIG. 35. Accordingly, the cassettes 703 can be unloaded.

In this example, a valve unit 705 and probe unit 710 are integrally formed. However, the present invention is not limited to this. The valve unit 705 and probe unit 710 may be separately formed and moved vertically by separate elevating driving mechanisms. In this example, 3-electrode systems 761 to which probe DNA is immobilized and pads 762 and 763 are formed on the same surface of the substrate 714. However, the present invention is not limited to this. The 3-electrode systems 761 may be formed on the upper surface of the substrate 714 while the pads 762 and 763 may be formed on the opposite surface. In this case, the valve unit 705 is arranged on the upper side of the cassette 703 and the probe unit 710 is arranged on the lower side. In this case, the valve unit 705 and probe unit 710 are inevitably separated.

Although not illustrated in FIG. 35, the base sequence automatic analyzing apparatus 700 incorporates the measurement system 12 which extracts an electrical signal from the base sequence detection chip in the cassette 703 or sends a signal, a temperature control mechanism 14, and the control mechanism 15. The control mechanism 15 in the base sequence automatic analyzing apparatus 700 is connected to the computer 16.

FIG. 56 is a view showing an example of the arrangement of the base sequence automatic analyzing apparatus 700 in loading the cassette 703. When the slide operation buttons 704a and 704b are pressed, the slide stages 702a and 702b slide from the housing 701 so that the cassette loading grooves 792 each having a predetermined depth appears outside the housing 701. Each cassette loading groove 792 has a temperature adjustment mechanism 720, positioning pins 709a and 709b, and a cassette type determination pin 789.

As the temperature adjustment mechanism 720, for example, a Peltier element is used. The cassette 703 is loaded such that the positioning pins 709a and 709b are inserted into cassette positioning holes 728a and 728b (to be described later), and the temperature adjustment mechanism 720 is positioned to a temperature adjustment window portion 743. In this cassette loaded state, a microswitch 811 is pressed by the cassette 703 to detect that the cassette 703 is loaded. The microswitch 811 is connected to the control mechanism 15. The switch change-over state can always be confirmed by the control mechanism 15.

FIGS. 69A and 69B are views for explaining the detection operation of the microswitch 811. As shown in FIG. 69A, the microswitch 811 is arranged on the surface of the cassette loading groove 792 of the slide stage 702a. When the cassette 703 is not loaded, the microswitch 811 projects from the surface of the cassette loading groove 792. When the cassette is loaded, the cassette 703 presses the microswitch 811, as shown in FIG. 69B. This press operation is detected by the control mechanism 15 connected to the microswitch 811. When the cassette 703 is unloaded from the cassette loading groove 792, the microswitch 811 returns to the state shown in FIG. 69A, i.e., projects from the groove surface. Hence, loading of the cassette can be repeatedly detected.

On the basis of the same principle as that of the microswitch 811, the type of cassette is determined by detecting the presence/absence of press of the cassette type determination pin 789. If the cassette 703 has a cassette type determination hole 749, the cassette type determination pin 789 is not pressed when the cassette is loaded. If the cassette has no cassette type determination hole 749, the cassette type determination pin 789 is pressed even when the cassette 703 is loaded. A signal representing the presence/absence of press of the cassette type determination pin 789 is output to the control mechanism 15. On the basis of the signal representing the presence/absence of pin press, the control mechanism 15 can determine the type of cassette. When a sensor that detects the degree of press of the cassette type determination pin 789 stepwise is used, a plurality of types of cassettes can be determined. In this case, the depth of the cassette type determination hole 749 is adjusted in accordance with the determinable degree of press.

After loading the cassettes, the slide operation buttons 704a and 704b are pressed to slide the slide stages 702a and 702b into the housing 701 (the direction indicated by the arrow in FIG. 56) so that the cassettes 703 are accommodated in the housing 701.

Figure 36:
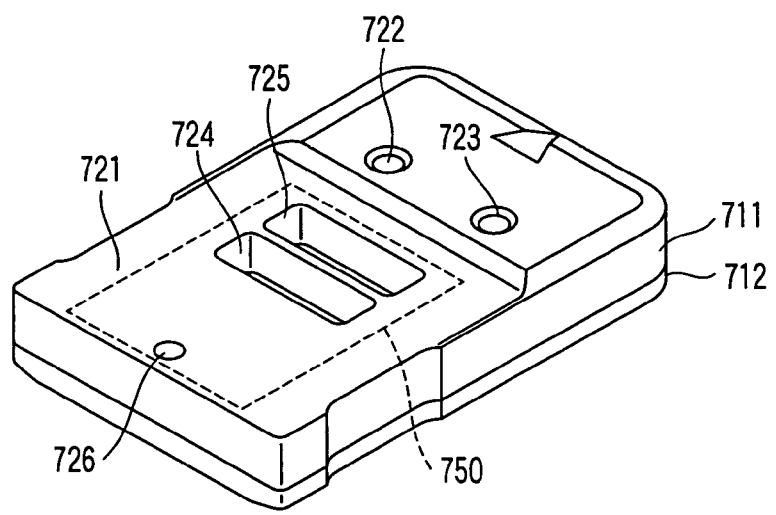
FIG. 36 is a perspective view of a cassette according to the second embodiment.

FIG. 36 is a perspective view of the cassette 703. The cassette 703 comprises a cassette top cover 711, cassette bottom cover 712, packing 713 (seal member), and the substrate 714. The inner surfaces of the cassette top cover 711 and cassette bottom cover 712 are made to oppose each other and fixed while inserting the packing 713 and substrate 714 between the cassette top cover 711 and the cassette bottom cover 712. Thus, the cassette 703 is completed.

The nozzle insertion holes 722 and 723 each having an almost circular section are formed to extend from an outer surface 721 to an inner surface 729 of the cassette top cover 711. The inner diameter of the nozzle insertion holes 722 and 723 is set to be slightly larger than the outer diameter of nozzles 707 and 708 and the introduction and delivery ports 752 and 753. The inner diameter of the nozzle insertion holes 722 and 723 is, e.g., about 3.2 mm.

The electric connector ports 724 and 725 each having an almost rectangular section are formed to extend from the outer surface 721 to the inner surface 729. Each of the electric connector ports 724 and 725 are used upon receiving the electric connector 730 (to be described later).

A seal detection hole 726 is formed to be extend from the outer surface 721 to the inner surface 729. The seal detection hole 726 is used to detect the presence/absence of a seal 750. FIG. 67A is a view showing a state wherein the seal 750 is attached in injecting a sample into the cassette. FIG. 67B is a view showing a state wherein the seal 750 is peeled after a sample is injected into the cassette. In the state shown in FIG. 67A, the seal detection hole 726 and electric connector ports 724 and 725 are covered with the seal 750. In the state shown in FIG. 67B, the seal 750 is not present, and the seal detection hole 726 and electric connector ports 724 and 725 are exposed. As shown in FIG. 67A, the seal 750 is adhered from the surface of the seal detection hole 726 on the outer surface 721 of the cassette 703 to the surfaces of the electric connector ports 724 and 725. A sample is injected into the cassette 703 while keeping the seal 750 adhered. With this structure, even when the sample solution undesirably drops to the electric connector port 724 or 725, the solution does not enter the actual port 724 or 725, and any problem such as an electrical short circuit is not posed because the port 724 or 725 is covered with the seal 750. After the sample is injected, the seal 750 is peeled.

FIG. 68 is a view showing an example of a mechanism to detect the presence/absence of the seal on the seal detection hole 726. As shown in FIG. 68, a detection light irradiation means 812 such as an LED and a detection photosensor 813 such as a photosensor are arranged such that detection light passes through a detection light passing hole 702e and the seal detection hole 726 at a position where the slide stage 702a is accommodated in the housing 701. More specifically, the detection light irradiation means 812 and detection photosensor 813 are arranged to oppose each other via the cassette 703 so that the detection light passing hole 702e and seal detection hole 726 are located on the optical path of the detection light when the slide stage 702a is accommodated.

The detection light irradiation means 812 and detection photosensor 813 may be fixed on the housing 701. Alternatively, only the detection light irradiation means 812 may be fixed on the housing 701 while the detection photosensor 813 may be fixed on the slide stage 702a. The detection light irradiation means 812 emits the detection light and the detection photosensor 813 detects it on the basis of an instruction from the control mechanism 15, and the detection photosensor 813 outputs a detection signal to the control mechanism 15.

The detection light is emitted such that it passes through the detection light passing hole 702e and seal detection hole 726, which are formed to extend from the groove surface to the bottom surface of the slide stage 702a. The photosensor 813 detects the light that has passed through the detection light passing hole 702e and seal detection hole 726. The detection signal is transmitted to the control mechanism 15.

In the state shown in FIG. 67A wherein the seal 750 is adhered to the cassette 703, the detection light is shielded by the seal 750. Hence, the detection photosensor 813 cannot detect the detection light. In the state shown in FIG. 67B wherein the seal 750 is peeled, the detection light is detected by the detection photosensor 813 without being shielded.

Accordingly, it can be detected whether the seal 750 of the cassette 703 is peeled. More specifically, even when the cassette 703 is set on the stage without peeling the seal 750, the nozzles 707a, 707b, 708a, and 707b and the electric connectors 730 are prevented from moving downward and coming into contact with the seal 750.

Figure 37:
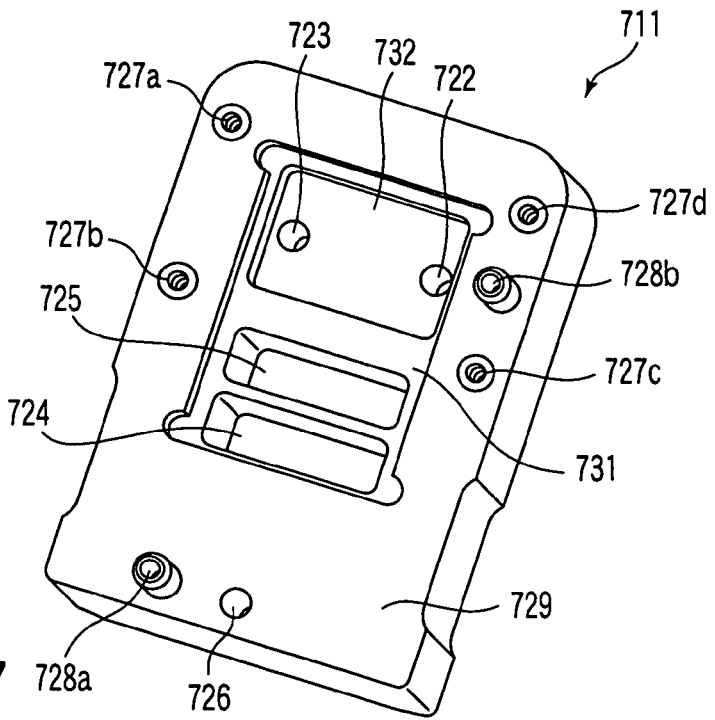
FIG. 37 is a perspective view of a cassette top cover to the second embodiment.

FIG. 37 is a perspective view of the cassette top cover 711 viewed from the side of the inner surface 729.

On the side of the inner surface 729, a substrate positioning groove 731 having a predetermined depth and almost the same sectional shape as that of the substrate 714 is formed. The substrate positioning groove 731 is surrounded by the inner surface 729. The substrate positioning groove 731 is formed to overlap the nozzle insertion holes 722 and 723 and the electric connector ports 724 and 725. When the substrate 714 is fitted in the substrate positioning groove 731, the substrate 714 can be positioned and arranged in the cassette top cover 711. The depth of the substrate positioning groove 731 is almost the same as the thickness of the substrate 714.

A packing positioning groove 732 deeper than the substrate positioning groove 731 is formed to overlap the substrate positioning groove 731 on the side of the inner surface 729. The packing positioning groove 732 is surrounded by the substrate positioning groove 731. The packing positioning groove 732 is formed to overlap the nozzle insertion holes 722 and 723. When the packing 713 is fitted in the packing positioning groove 732, the packing 713 can be positioned and arranged in the cassette top cover 711. The depth of the packing positioning groove 732 with respect to the substrate positioning groove 731 is almost the same as the thickness of a packing main body 751 (to be described later). Hence, the depth of the packing positioning groove 732 with respect to the inner surface 729 is almost the same as a thickness obtained by adding the thickness of the substrate 714 to the thickness of the packing main body 751.

Four threaded holes 727a, 727b, 727c, and 727d are formed at the periphery portion of the inner surface 729. With the threaded holes 727a to 727d, the cassette top cover 711 and cassette bottom cover 712 can be fixed by screwing.

Two cassette positioning holes 728a and 728b are formed at the peripheral portion of the inner surface 729. When the cassette 703 is set while aligning the cassette positioning holes 728a and 728b to two positioning pins provided on each of the slide stages 702a and 702b, the cassette 703 can be positioned to each of the slide stages 702a and 702b.

Figure 38:
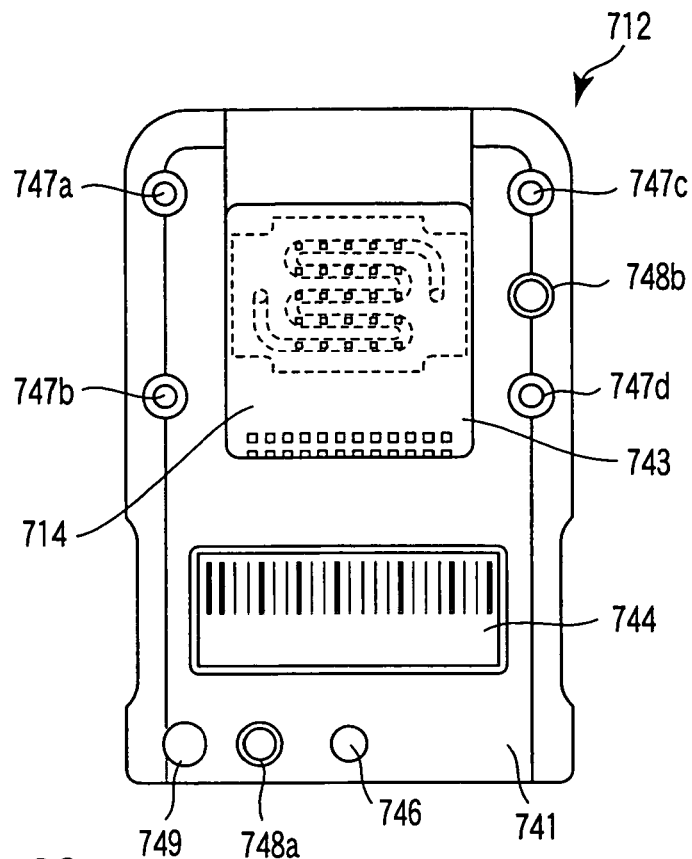
FIG. 38 is a view showing the structure of a cassette bottom cover according to the second embodiment.

FIG. 38 is a plan view of the cassette bottom cover 712 viewed from an outer surface 741. The temperature adjustment window portion 743 is formed to extend from the outer surface 741 to an inner surface 742. The substrate 714 is arranged on the side of the inner surface 742 of the temperature adjustment window portion 743. When the substrate 714 is arranged to come into contact with the temperature adjustment mechanism 720 arranged on each of the slide stages 702a and 702b through the temperature adjustment window portion 743, the temperature of the substrate 714 can be adjusted from the side of the cassette bottom cover 712.

The outer surface 741 has a bar code 744. The identification number of the cassette 703 is written as bar code information of the bar code 744. When the bar code 744 with the identification number is read by a bar code reading means, the cassette 703 can be identified.

A seal detection hole 746 is formed to extend through the outer surface 741. The seal detection hole 746 of the cassette bottom cover 712 is formed at a position where the seal detection hole 746 communicates with the seal detection hole 726 of the cassette top cover 711 when the cassette top cover 711 and cassette bottom cover 712 are fixed. Accordingly, when the cassette top cover 711 and cassette bottom cover 712 are fixed, the seal detection hole 726 which extends from the cassette top cover 711 to the cassette bottom cover 712 is formed. When the seal detection hole 726 is irradiated with the detection light, the presence/absence of the seal 750 can be detected.

Four threaded holes 747a, 747b, 747c, and 747d are formed at the peripheral portion of the outer surface 741. Each of the threaded holes 747a to 747d and a corresponding one of the threaded holes 727a to 727d formed in the cassette top cover 711 are screwed. Accordingly, the cassette bottom cover 712 can be fixed to the cassette top cover 711.

Two cassette positioning holes 748a and 748b are formed at the peripheral portion of the outer surface 741. The cassette 703 is set while aligning the cassette positioning holes 748a and 748b to two positioning pins provided on each of the slide stages 702a and 702b. Accordingly, the cassette 703 can be positioned to each of the slide stages 702a and 702b.

Reference numeral 749 denotes the cassette type determination hole 749. The type of cassette can be determined on the basis of the presence/absence of the hole. The type determination can be automatically done on the basis of the presence/absence of press of the cassette type determination pin 789. The pin press state of the cassette type determination pin 789 is detected by the control mechanism 15. In the following example, the cassette 703 having the cassette type determination hole 749 is used. Even when the cassette 703 having no cassette type determination hole 749 is used, the same measurement can be executed except that the type of cassette to be determined is different. Alternatively, the control mechanism 15 may cause the display section 893 to display a warning representing that the type of cassette 703 is different and prevent the measurement process from starting. Alternatively, a fixed pin may be used as the cassette type determination pin 789 such that the cassette 703 having no cassette type determination hole 749 cannot be loaded. Accordingly, any erroneous cassette 703 may be prevented from being set.

Figure 39:
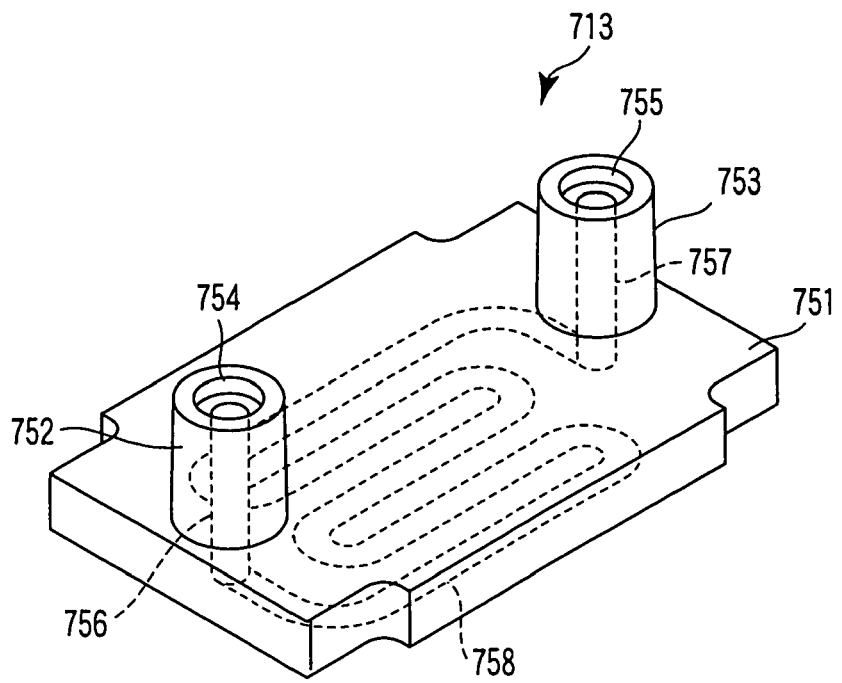
FIG. 39 is a perspective view of a packing according to the second embodiment.

FIG. 39 is a perspective view of the packing 713. The packing 713 comprises the packing main body 751, introduction port 752, and delivery port 753. The packing main body 751 has an almost rectangular shape and a predetermined thickness. The four corners of the packing main body 751 are cut. The introduction port 752 and delivery port 753 are ports each having a cylindrical shapes. The introduction port 752 and delivery port 753 are arranged on the major surface of the packing main body 751 near the two ends along the long sides and near the central portion along the short sides. The introduction port 752 and delivery port 753 have, at their distal ends, opening portions 754 and 755, respectively. Channels 756 and 757 are formed through the axes of the introduction port 752 and delivery port 753 to extend from the opening portions 754 and 755 to the packing main body 751 in a direction perpendicular to the major surface of the packing main body 751. A groove 758 having a curved shape is formed on the lower surface of the packing main body 751 from the formation position of the introduction port 752 to the formation position of the delivery port 753. The lower surface of the packing main body 751 is almost flat. The groove 758 is connected to the channels 756 and 757. The sectional areas of the channels 756 and 757 and the groove 758 are almost the same.

Figure 40:
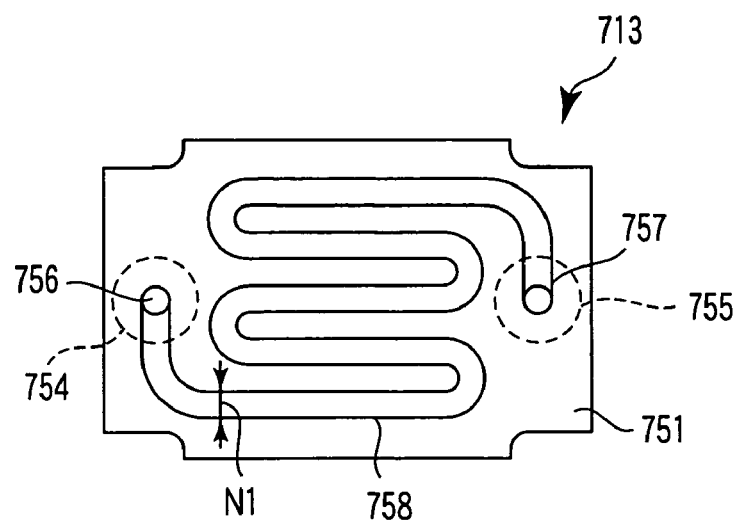
FIG. 40 is a plan view of the packing according to the second embodiment.

FIG. 40 is a plan view of the packing 713. The groove 758 goes from the channel 756 toward the channel 757, curves at a predetermined curvature, turns, and goes again from the channel 757 to the channel 756. the groove 758 is formed in this way such that it repeatedly turns a plurality of number of times between the channels 756 and 757. When each turn of the groove 758 has a curve at a predetermined curvature, any residual biochemical solution or air generated when a corner of a turn is formed can be suppressed.

Figure 41:
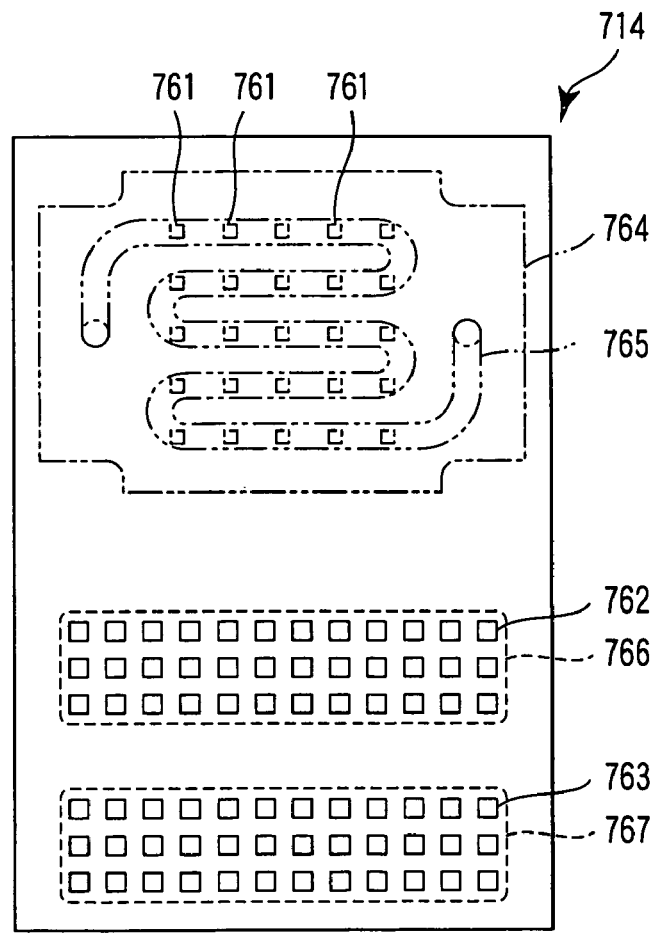
FIG. 41 is a plan view of a substrate according to the second embodiment.

FIG. 41 is a plan view of the substrate 714. The 3-electrode systems 761 and the pads 762 and 763 are formed on the major surface of the substrate 714. The 3-electrode system 761 and pad 762, and the 3-electrode system 761 and pad 763 are connected by wiring lines (not shown). The 3-electrode systems 761 are electrodes each formed from a combination of a working electrode, counter electrode, and reference electrode shown in the first embodiment. DNA probes are immobilized to the working electrodes.

FIG. 41 shows the layout of the substrate 714 and the packing 713 which overlaps a portion of the substrate 714. Reference numeral 764 denotes a packing arrangement position 764; and 765, a channel formation position. The 3-electrode systems 761 are formed at the packing arrangement position 764 while aligning to the channel formation position 765. Accordingly, when the packing 713 and substrate 714 are positioned to the cassette top cover 711 and cassette bottom cover 712 and fixed between them, a channel is formed by the groove 758 and the surface of the substrate 714. In addition, the 3-electrode systems 761 are exposed to the surface of the channel. More specifically, a gap is formed on the 3-electrode systems 761 by the groove 758. A channel is formed by the gap. In this state, sealing between the packing 713 and the substrate 714 is held.

Reference numerals 766 and 767 denote regions where the electric connector ports 724 and 725 are arranged when the packing 713 and substrate 714 are sandwiched and fixed between the cassette top cover 711 and the cassette bottom cover 712. The electric connectors 730 come into contact with pads 762 and 763 formed in the electric connector formation positions 766 and 767 through the electric connector ports 724 and 725. Accordingly, the 3-electrode systems 761 and the electric connector 730 arranged through the electric connector port 724 or the 3-electrode system 761 and the electric connector 730 arranged through the electric connector port 725 can be rendered conductive.

The packing arrangement position 764 functions as a sensor region where a DNA probe is immobilized, and the presence/absence of hybridization is detected by an electrochemical reaction. The pads 762 and 763 function as electrical contact regions where an electrical signal is extracted from the substrate 714 to the outside of the cassette 703. The sensor regions and electrical contact region are separately arranged.

Figure 43:
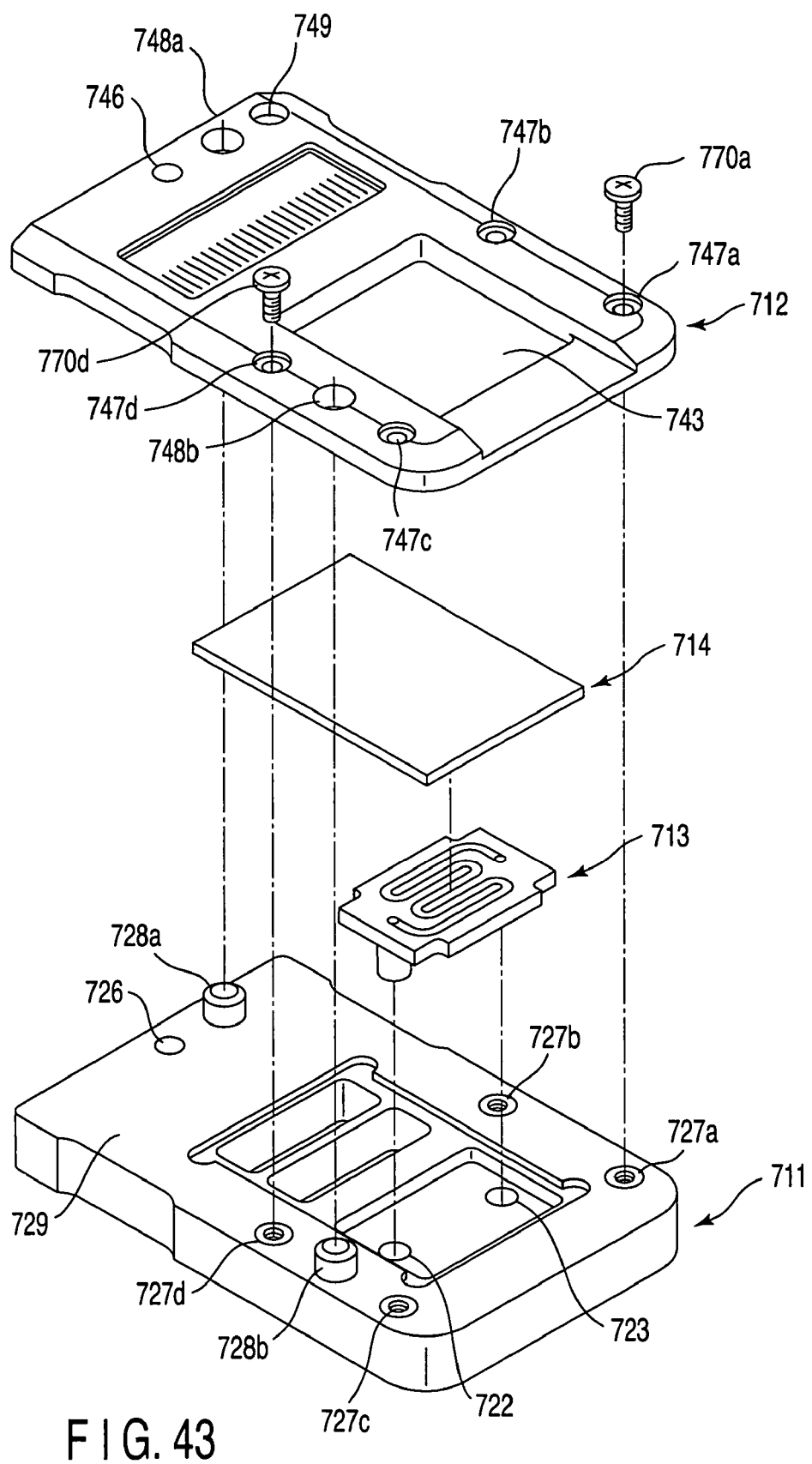
FIG. 43 is a view showing the assembled state of the cassette according to the second embodiment.

FIGS. 42 and 43 are views showing the assembled state of the cassette 703 viewed from the side of the cassette top cover 711 and the side of the cassette bottom cover 712, respectively.

First, the packing 713 is fitted into the packing positioning groove 732 while aligning them to each other such that the introduction port 752 and delivery port 753 are inserted into the nozzle insertion holes 722 and 723. Next, the substrate 714 is positioned to the substrate positioning groove 731 such that the major surface of the substrate 714, i.e., the surface on which the 3-electrode systems 761 and pads 762 and 763 are formed faces the side of the cassette top cover 711. Next, the cassette bottom cover 712 is placed on the cassette top cover 711 such that the inner surface 742 faces the side of the cassette top cover 711, and the positions of the threaded holes 747*a* to 747*d* correspond to those of the threaded holes 727*a* to 727*d*. Screws 770*a* to 770*d* are threadably inserted into the threaded holes 747*a* to 747*d* and threaded holes 727*a* to 727*d*. Accordingly, the cassette top cover 711 and cassette bottom cover 712 are threadably attached to each other. In addition, the packing 713 and substrate 714 are sandwiched and fixed between the cassette top cover 711 and the cassette bottom cover 712. Thus, the cassette 703 is completed. In this complete state, a channel is formed from the nozzle insertion hole 722 to the nozzle insertion hole 723 while communicating sequentially through the opening portion 754, channel 756, groove 758, channel 757, and opening and 755.

FIGS. 42 and 43 show an example in which the cassette top cover 711 and cassette bottom cover 712 are fixed by screwing. However, the present invention is not limited to this. For example, an engaging method using projecting and recess members may be used. FIG. 59 is a view showing an example of the structure of a cassette 821 fixed by engaging. As shown in FIG. 59, a total of six engaging holes 824 are formed in a cassette top cover 822. That is, three engaging holes are formed in each of the side portions of the cassette top cover 822 to extend from the inner wall to the outer wall. On the other hand, a total of six pawl-shaped engaging members 825 are formed in a cassette bottom cover 823. That is, three engaging members 825 are formed on the inner surface of each of the two side portions of the cassette bottom cover 823. The components except the engaging members 825 and engaging holes 824 are the same as those of the cassette top cover 711 and cassette bottom cover 712 shown in FIGS. 42 and 43, and a detailed description thereof will be omitted.

When each of the engaging members 825 and a corresponding one of the engaging holes 824 engage at, e.g., a position indicated by the alternate long and short dashed line in FIG. 60A, the cassette top cover 822 and cassette bottom cover 823 are fixed by engaging, as shown in FIG. 60B.

FIG. 44 is a sectional view of the side surface of the cassette 703 which is completed in accordance with the procedures shown in FIGS. 42 and 43. As shown in FIG. 44, the cassette 703 has a total of three types of openings.

The first openings are openings formed by the packing positioning groove 732 and nozzle insertion holes 722 and 723. With the first openings, the nozzles 707 are attached to positions corresponding to the projecting portions (ports) of the packing 713. Hence, a biochemical solution or air can be introduced or delivered. In addition, a sample solution can be injected using a pipette or the like.

The second openings are openings which are formed in the same surface as that of the first openings while being separated from the portion where the packing 713 is fixed, and formed by the electric connector ports 724 and 725. In the second openings, the pads 762 and 763 to obtain an electrical contact between the substrate 714 and the apparatus main body are arrayed. The probe units (electric connectors 730) arranged in the apparatus main body are inserted into the second openings. Accordingly, the electrical contact with the pads on the substrate 714 can be obtained.

The third opening is formed in the surface that is opposite to that of the first and second openings via the substrate 714. The third opening is formed at a position corresponding to the lower surface of the portion where the packing 713 is fixed, i.e., in the lower surface of the first openings. With the third opening, the temperature control mechanism 14 can come into direct contact with the lower surface of the substrate 714 so that the temperature of the substrate 714 can be controlled.

More specifically, the nozzle 707 is pressed again the nozzle insertion hole 722 in the direction indicated by an arrow. The electric connector 730 is inserted into each of the electric connector ports 724 and 725. The lower surface side of the substrate 714, i.e., the side where the 3-electrode systems 761 are not formed is exposed through the temperature adjustment window portion 743. The cassette 703 is placed on the slide stage 702 such that the temperature adjustment mechanism 720 comes into contact with the exposed surface. Accordingly, the temperature of the substrate 714 can be adjusted from the lower surface side.

FIG. 45 is a sectional view of the channel of the cassette 703. The nozzle 707 and nozzle 708 are inserted into the nozzle insertion holes 722 and 723 and pressed against the introduction port 752 and delivery port 753 of the packing 713. With this structure, the nozzle 707 and nozzle 708 communicate with the introduction port 752 and delivery port 753. In this state, a biochemical solution or air is supplied from the nozzle 707. The biochemical solution or air is delivered from the nozzle 708 through the channel formed by the groove 758 formed in the packing 713 and the substrate 714.

FIGS. 46 to 51 are views showing the detailed structures of the port tip shape of the packing 713.

Figure 46:
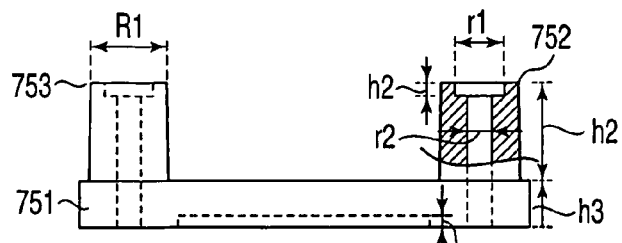
FIG. 46 is a view showing the detailed structure of a packing tip shape according to the second embodiment.

FIG. 46 shows the first example of the port tip shape. An inner diameter $r_1$ of the opening portions 754 and 755 at the distal end portions of the introduction port 752 and delivery port 753 is formed to be larger than an inner diameter $r_2$ of the channels 756 and 757 stepwise, i.e., discontinuously. The material of the packing 713 is silicone rubber. The hardness is, e.g., about 60. The packing 713 is formed by injection molding using a mold to be integrated with the packing main body 751, introduction port 752, delivery port 753, and the channels. A depth $g_1$ (corresponding to the height of the channel) of 658 is about 0.7 mm. A width $w_1$ is about 1 mm. A height $h_1$ of each of the introduction port 752 and delivery port 753 is about 4 mm. An outer diameter $R_1$ is about 3 mm. The inner diameters $r_1$ and $r_2$ are respectively, e.g., $r_1$=about 2 mm and $r_2$=about 1 mm. A height $h_2$ of the portion with the inner diameter $r_1$ is, e.g., about 0.5 mm. A thickness $h_3$ of the packing main body 751 is about 3 mm. The surfaces at which the packing 713 and substrate 714 are bonded are preferably mirror-polished.

From the second example, the material, hardness, forming method, and dimension are the same as in the first example unless otherwise specified.

Figure 47:
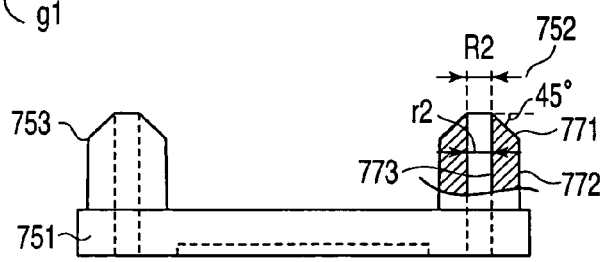
FIG. 47 is a view showing the detailed structure of another packing tip shape according to the second embodiment.

FIG. 47 shows the second example of the port tip shape. The inner diameter $r_2$ of the opening portion 754 at the distal end portion of each of the introduction port 752 and delivery port 753 is constantly about 1 mm. The outer diameter continuously decreases from the outer diameter $R_1$ toward the distal end. At the tip, the outer diameter is an outer diameter $R_2$ almost equal to the inner diameter $r_2$. The angle of an outer surface 771 at the portion with the small outer diameter with respect to the major surface of the packing main body 751 is about 45°. The outer diameter becomes small in the range of about 1 mm from the distal end of each of the introduction port 752 and delivery port 753. The outer diameter is almost constant on an outer surface 772 closer to the packing main body 751 than the outer surface 771. The outer surface 772 may also be tilted by about 10 with respect to, e.g., an inner surface 773 such that the outer surface 772 is also slightly tapered toward the tip. This also applies to the examples shown in FIG. 46 and FIGS. 48 to 51.

Figure 48:
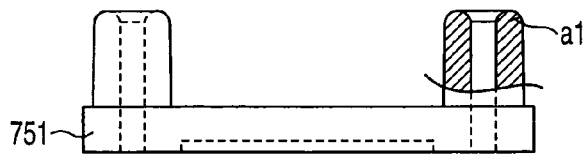
FIG. 48 is a view showing the detailed structure of still another packing tip shape according to the second embodiment.

FIG. 48 shows the third example of the port tip shape. The inner diameter of the distal end portion of each of the introduction port 752 and delivery port 753 gradually increases while the outer diameter gradually decreases. More specifically, each of the introduction port 752 and delivery port 753 has a semi-circular sectional shape having, e.g., a radius $a_1$=about 0.5 mm.

Figure 49:
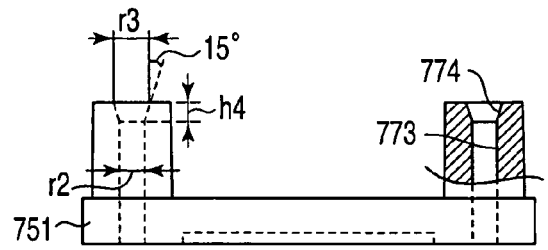
FIG. 49 is a view showing the detailed structure of still another packing tip shape according to the second embodiment.

FIG. 49 shows the fourth example of the port tip shape. The outer diameter of each of the introduction port 752 and delivery port 753 is constant. The inner diameter is defined to be gradually increase toward the distal end and have a bowl shape. More specifically, from the distal end of each of the introduction port 752 and delivery port 753 to a depth of about 0.75 mm, the inner diameter gradually continuously decreases from an inner diameter $r_3$ (e.g., about 1.4 mm) to the inner diameter $r_2$. At a deeper position, each of the introduction port 752 and delivery port 753 has the predetermined inner diameter $r_2$. An inner surface 774 at the position where the inner diameter is large is tilted by about 15° with respect to the inner surface 773. When the inner wall is formed into the bowl shape, the tip of a pipette that injects a sample can be smoothly inserted into the introduction port 752 and delivery port 753. In addition, the sealing properties between the packing 713 and the pipette can be increased. Hence, a sample can easily be introduced onto the substrate 714.

Figure 50:
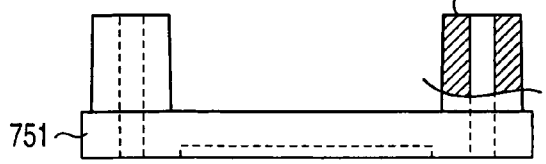
FIG. 50 is a view showing the detailed structure of still another packing tip shape according to the second embodiment.

FIG. 50 shows the fifth example of the port tip shape. Both the outer diameter and the inner diameter of each of the introduction port 752 and delivery port 753 are almost constant toward the distal end. An outer surface 775 at the distal end is almost perpendicular to the channels 756 and 757.

Figure 51:
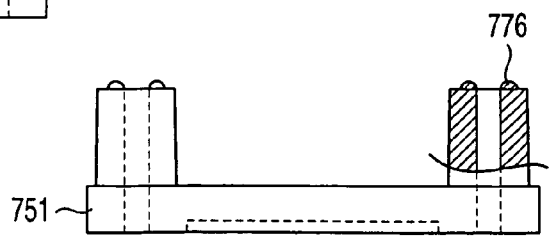
FIG. 51 is a view showing the detailed structure of still another packing tip shape according to the second embodiment.

FIG. 51 shows the sixth example of the port tip shape. Each of the introduction port 752 and delivery port 753 has almost the same basic structure as that of the example shown in FIG. 50 except an O-ring 776 is formed at the distal end.

The dimensions of the port tip shapes shown in FIGS. 46 to 51 are merely examples. They can be appropriately changed in accordance with the convenience in molding, the size of the substrate 714, and the like. The material of the packing 713 is not limited to silicone rubber. Elastomer, Teflon, Daiflon, and any other resin can also be used.

The port tip need not be formed to be perpendicular to the major surface of the packing main body 751. For example, the port tip may be tilted with respect to the major surface by a predetermined angle. Alternatively, the port tip may be formed to be perpendicular to the major surface of the packing main body 751, bent halfway at the formation position, and then extend in a direction that is not perpendicular to the major surface of the packing main body 751.

Figure 52:
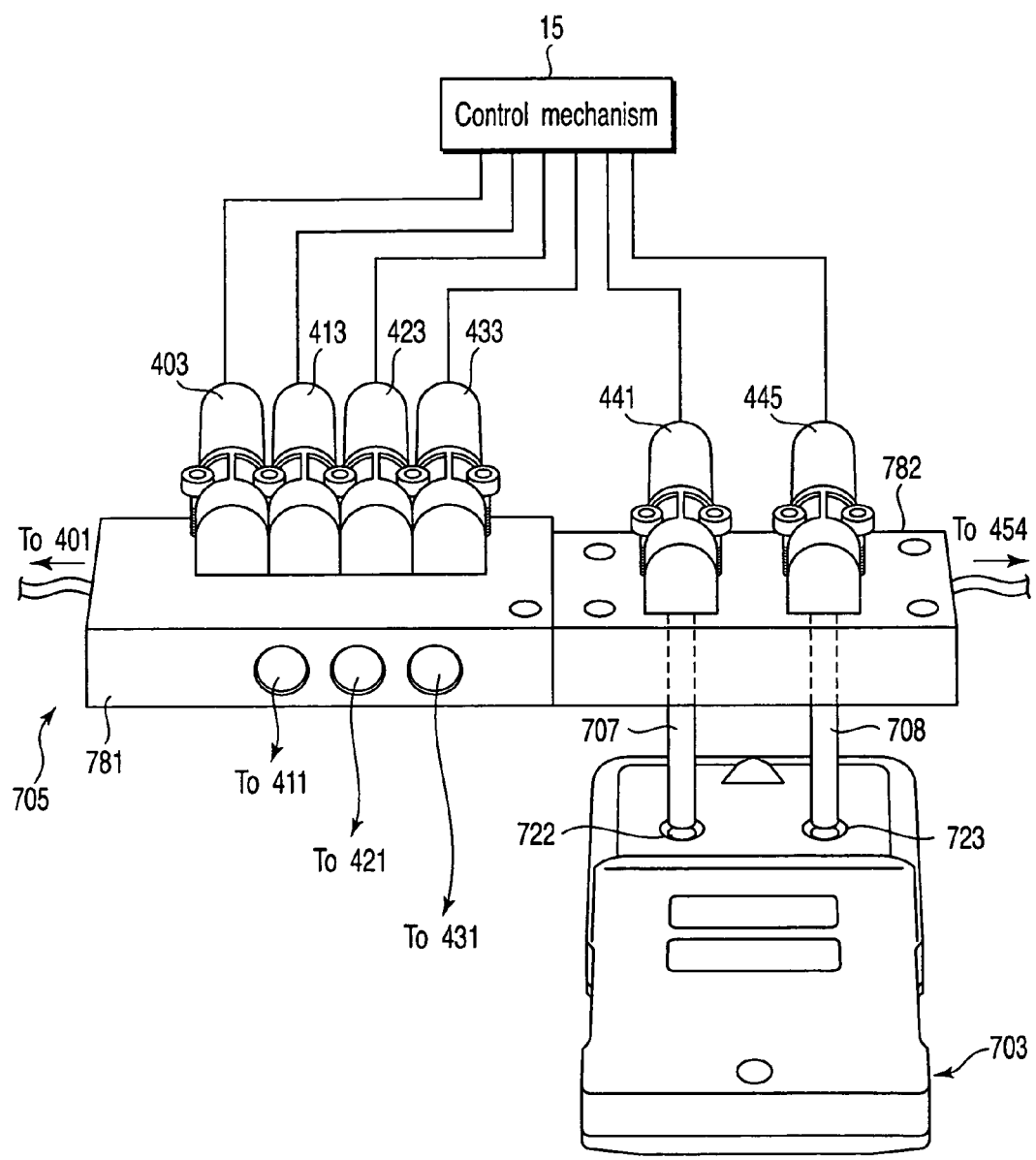
FIG. 52 is a view showing the overall arrangement of a valve unit according to the second embodiment.

FIG. 52 is a view showing the overall arrangement of the valve unit 705. The arrangement of the probe unit 710 is not illustrated in FIG. 52. In the valve unit 705, valve bodies 781 and 782 are connected and fixed. The valve body 781 has a two-way solenoid valve 403 and three-way solenoid valves 413, 423, and 433. The valve body 782 has three-way solenoid valves 441 and 445. The valve bodies 781 and 782 are made of, e.g., PEEK resin. If the valve bodies 781 and 782 are to be separately formed and connected, PTFE is used as a packing at the joint portion. Hence, portions of the valve bodies 781 and 782, which come into contact with a biochemical solution, are made of PEEK and PTFE. Each of the valve bodies 781 and 782 has a cavity having an almost constant sectional shape. The cavity functions as a pipe that connects each solenoid valve (to be described later) and the packing 713. The cavity formed in the valve body 782 communicates with the nozzles 707 and 708. The nozzles 707 and 708 are made of PEEK resin.

FIG. 61 is a view showing an example of the structure of a valve unit 831 as a modification of the valve unit 705. The valve unit 705 shown in FIG. 52 uses the face-mounted solenoid valves 403, 413, 423, 433, 441, and 445. Instead, the valve unit shown in FIG. 61 uses embedded solenoid valves 832, 833, 834, 835, 836, and 837. The functions of the solenoid valves 832, 833, 834, 835, 836, and 837 are the same as those of the solenoid valves 403, 413, 423, 433, 441, and 445. The remaining components are the same as those of the valve unit 705.

FIG. 62 is a view showing the structure of a valve unit 841 according to another modification. As shown in FIG. 52, the valve body 781 which has the solenoid valves 403, 413, 423, and 433 and the valve body 782 which has the solenoid valves 441 and 445 are separate bodies. Instead, an integral valve body 842 may have the solenoid valves 403, 413, 423, 433, 441, and 445.

Figure 63:
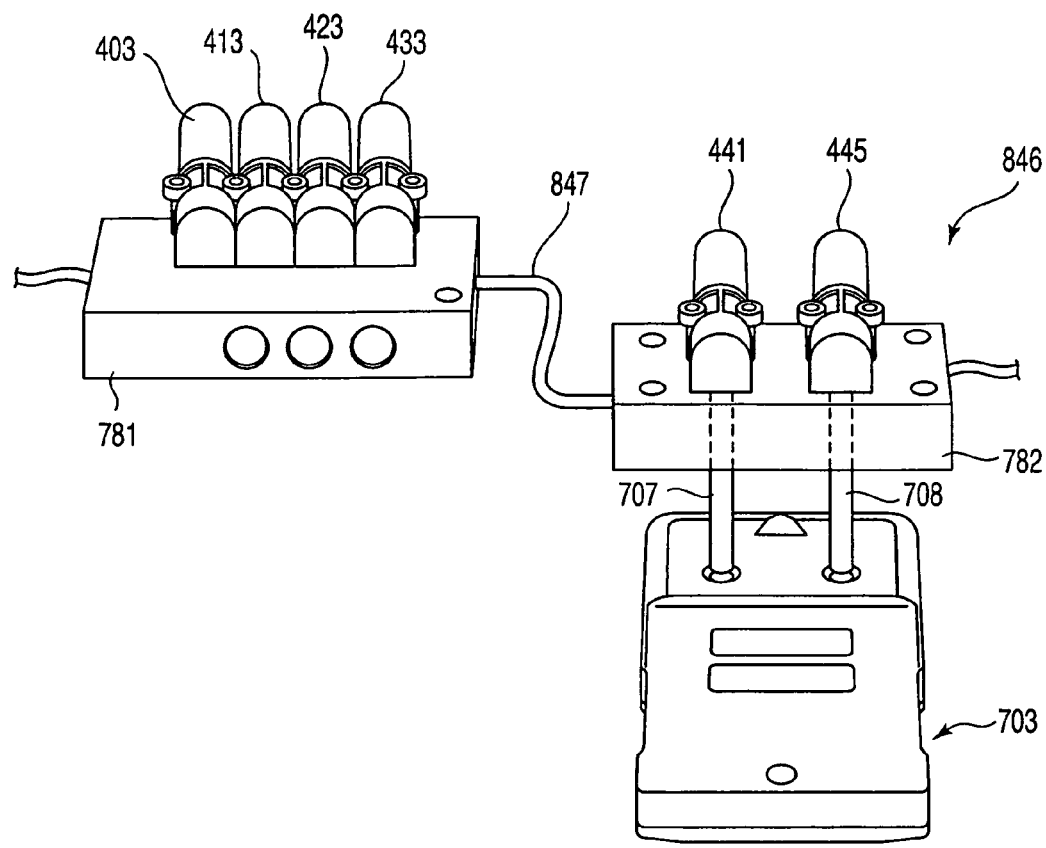
FIG. 63 is a view showing still another example of the valve unit according to the second embodiment.

FIG. 63 is a view showing the structure of a valve unit 846 according to still another modification. The valve unit 846 has the two valve bodies 781 and 782, as in FIG. 52. The valve bodies 781 and 782 are connected by a tube 847. The tube 847 communicates the three-way solenoid valve 433 with the three-way solenoid valve 441, like the pipe 435 in FIG. 17. When the valve unit is formed by a plurality of valve bodies, the valve bodies may be connected by a tube or the like. In this case, each valve body may have a driving mechanism.

Figure 64:
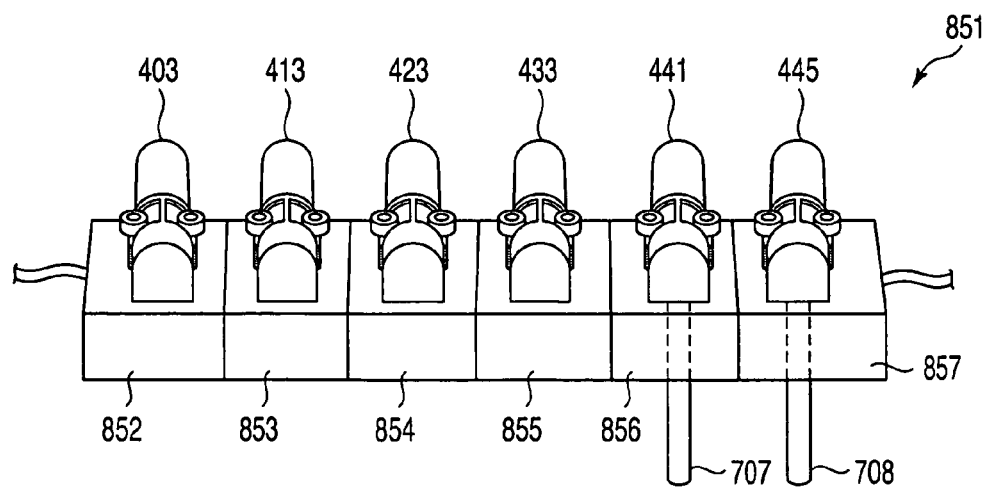
FIG. 64 is a view showing still another example of the valve unit according to the second embodiment.

FIG. 64 is a view showing the structure of a valve unit 851 according to still another modification. In the valve unit 851 according to this modification, a plurality of valve bodies 852 to 857 have the solenoid valves 403, 413, 423, 433, 441, and 445, respectively. The valve bodies 852 to 857 are connected and fixed by, e.g., PTFE seals. Accordingly, the valve bodies 852 to 857 function like the valve unit 705 shown in FIG. 52. The valve bodies 852 to 857 may be connected by tubes, as in FIG. 63.

FIG. 53 is a view showing the functional arrangement of the valve unit 705 shown in FIG. 52. The two-way solenoid valve 403 is not illustrated in FIG. 52. The same reference numerals as in the arrangement of the solution supply system 13 shown in FIG. 17 denote the same components in FIG. 53, and a detailed arrangement will be omitted.

The valve bodies 781 and 782 have internal pipes. With these pipes, the channel of a biochemical solution or air between the three-way solenoid valves 413, 423, and 433 is defined.

The three-way solenoid valve 413 selectively supplies air or milli-Q water to the three-way solenoid valve 423 on the downstream side. The three-way solenoid valve 423 selectively supplies a buffer or the air or milli-Q water from the three-way solenoid valve 413 to the three-way solenoid valve 433 on the downstream side. The three-way solenoid valve 433 selectively supplies a intercalating agent or the air, milli-Q water, or buffer from the three-way solenoid valve 423 to the valve body 782 on the downstream side. The three-way solenoid valve 441 switches between supply of the air or biochemical solution from the valve body 781 to the nozzle 707 and supply to the three-way solenoid valve 445 through a bypass pipe 446. The three-way solenoid valve 445 switches supply of the air or biochemical solution from the three-way solenoid valve 441 and delivery of the biochemical solution or air from the cassette 703 through the nozzle 708.

A solution supply pump 454 is arranged downstream of the cassette 703. If a pump is provided for each of milli-Q water, a buffer, and an intercalating agent, three pumps are necessary, resulting in a bulky apparatus. Assume that a pump is arranged upstream of the cassette 703 to supply a liquid by a positive pressure. If a pipe has leakage, the solution may leak from that portion. However, as in the above arrangement, when the solution supply pump 454 is arranged downstream of the cassette 703 to supply a liquid by a negative pressure. In this case, only one common solution supply pump 454 suffices for all biochemical solutions. If a pipe has leakage, the biochemical solution is not naturally supplied. In addition, the liquid does not leak from the leakage portion of the pipe.

In the valve unit 705, to supply a buffer into the cassette 703, the three-way solenoid valves 423, 441, and 445 and the solution supply pump 454 are turned on. Accordingly, the buffer is sucked up. The biochemical solution is switched to the side of the nozzle 707. The biochemical solution is sucked up from the nozzle 707 to the cassette 703 and then from the cassette 703 to the nozzle 708. The biochemical solution can be wasted through the three-way solenoid valve 454.

To supply milli-Q water into the cassette 703, the three-way solenoid valve 413 is turned on in place of the three-way solenoid valve 423. To supply an intercalating agent into the cassette 703, the three-way solenoid valve 433 is turned on in place of the three-way solenoid valve 423. To supply air into the cassette 703, the three-way solenoid valve 403 is turned on, and all the three-way solenoid valves 413, 423, and 433 are turned off.

The internal capacity of the pipes of the cavity portions formed in the valve bodies 781 and 782 of the valve unit 705 is about 200 μL. As an example different from this embodiment, the three-way solenoid valves are connected by tubes to form the same flow as in this embodiment. In this case, an internal capacity of about 500 μL is necessary. As compared to this example, the amount of a reagent can greatly be decreased. In the example different from this embodiment, the internal capacity between the valve unit 705 and the cassette 703 is also as large as 100 μL or more. In this embodiment, however, the internal capacity can greatly be decreased to 10 μL. With this structure, the amount of a solution or air that undesirably flows in the cassette 703 after switching the reagent can largely be reduced. As a result, any variation in reaction or measurement can be reduced. The reproducibility of the result also largely increases.

Figure 65:
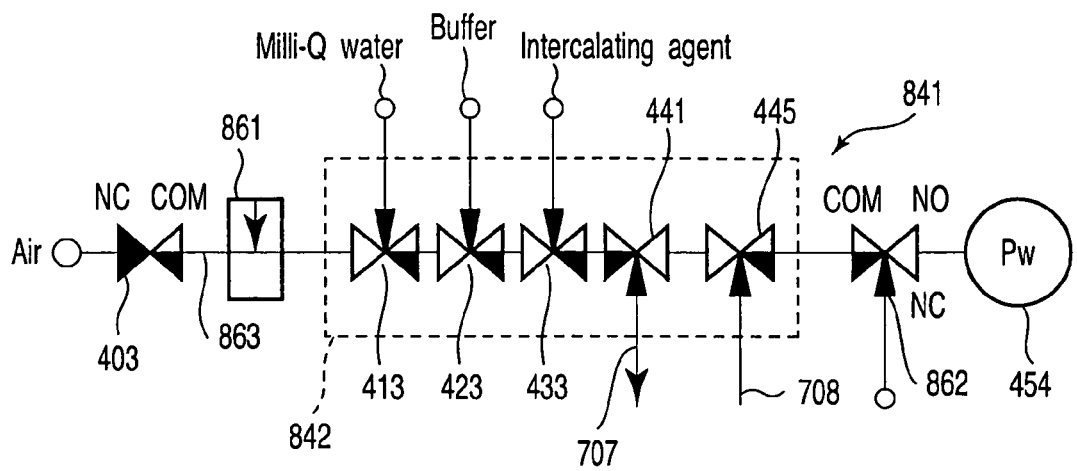
FIG. 65 is a view showing the functional arrangement of another valve unit according to the second embodiment.

FIG. 65 is a view showing a modification of the functional arrangement of the valve unit 841. The same reference numerals as in FIG. 53 denote the same components, and a detailed description thereof will be omitted. In the functional arrangement of the valve unit 841 shown in FIG. 65, to improve the reaction efficiency and reaction uniformity in the cassette 703, a mechanism that oscillates a biochemical solution in the cassette 703 is introduced.

The two-way solenoid valve 403 serving as an air stop valve is arranged upstream of the valve unit 841. In addition, a liquid oscillation mechanism 861 which oscillates a biochemical solution is arranged on the tube 863 between the two-way solenoid valve 403 and the three-way solenoid valve 411. A leakage valve 862 is arranged downstream of the valve unit 841 between the three-way solenoid valve 445 and the solution supply pump 454. As the liquid oscillation mechanism 861, for example, a pinch valve is used. The two-way solenoid valve 403, liquid oscillation mechanism 861, and leakage valve 862 are driven on the basis of an instruction from the control mechanism 15, like the remaining solenoid valves.

An example of reaction principle using the valve unit 841 will be described below.

The valve unit 841 is set to form a channel by air inside. More specifically, the solenoid valves 413, 423, and 433 are turned off. That is, the biochemical solution supply side is blocked, and the air supply side channel is opened. In addition, the solenoid valves 441 and 445 are turned on. That is, the channel is switched from the bypass side to the side of the cassette 703. Furthermore, the solenoid valve 403 is turned off to close the air supply channel. The leakage valve 862 is turned on to open one end of the channel. Accordingly, the channel on the air side is closed while the leakage side is opened.

In this state, the liquid oscillation mechanism 861 is turned on/off. The tube in the liquid oscillation mechanism 861 is repeatedly pressed and opened. Accordingly, the volume changes, and the biochemical solution onto the substrate in the cassette is oscillated. The liquid oscillation amount can be adjusted by changing the inner diameter of the tube used in the pinch valve, the tube press width, and the press area. When a tube having an inner diameter of 1 mm is pressed by a width of 5 mm, a biochemical solution of about 4 μL can be oscillated. The volume of the channel on the substrate 714, which is formed by the packing 713 and substrate 714, is about 30 μL. A biochemical solution corresponding to about 10% of the channel volume can be oscillated.

Such biochemical solution oscillation can be effectively executed in (1) hybridization process, (2) cleaning process, and (3) intercalating agent supply process. When sample DNA is oscillated in the hybridization process (1), the hybridization efficiency can be increased, and the hybridization time can be shortened. When a buffer solution is oscillated in the cleaning process (2), the efficiency of peeling nonspecific absorption DNA can be increased so that the cleaning time can be shortened. When an intercalating agent is oscillated in the intercalating agent supply process (3), the uniformity of the concentration of the intercalating agent can be increased. In addition, the intercalating agent adsorption uniformity can also be increased. As a result, any variation in signal can be reduced, and the S/N ratio can be improved. The effect of biochemical solution oscillation can be obtained either by applying the biochemical solution oscillation process to al the processes (1) to (3) or by applying the biochemical solution oscillation process to some of the processes (1) to (3). More specifically, biochemical solution oscillation can be effectively executed in, e.g., (s21), (s28), and (s33) in the flow chart shown in FIG. 18.

Figure 66A:
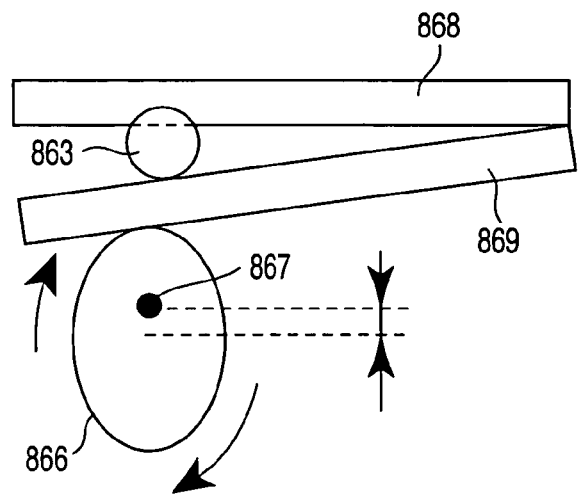
FIGS. 66A and 66B are views showing examples of a liquid oscillation mechanism according to the second embodiment.
Figure 66B:
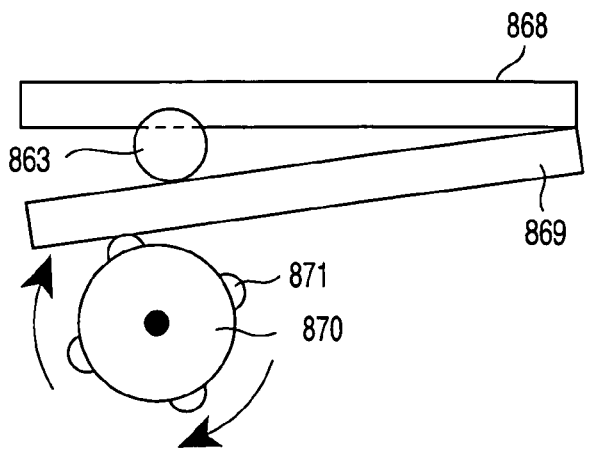

In the example shown in FIG. 65, a pinch valve is used. However, the present invention is not limited to this. FIGS. 66A and 66B are views showing modifications of the liquid oscillation mechanism.

FIG. 66A shows an example in which an eccentric cam 866 is used as the liquid oscillation mechanism. The eccentric cam 866 has an almost elliptical sectional shape. The eccentric cam 866 can be rotated by a cam rotating mechanism 892 about an eccentricity 867 separated from the center of the cam by a predetermined distance. The cam rotating mechanism 892 is controlled by the control mechanism 15. The tube 863 is sandwiched and held between a fixed member 868 and a movable member 869. When the eccentricity 867 is located between the cam center and the movable member 869, as shown in FIG. 66A, by rotation by the cam rotating mechanism 892, the eccentric cam 866 is located relatively far from the movable member 869. Hence, the tube 863 is opened without being pressed. On the other hand, when the cam center is located on the opposite side of the movable member 869, unlike FIG. 66A, the movable member 869 is pressed against the fixed member 868 by the eccentric cam 866. The tube 863 is pressed between the fixed member 868 and the movable member 869. When the eccentric cam 863 repeatedly rotates, the press state and open state of the tube 863 are repeated. As a result, the biochemical solution in the tube 863 oscillates.

FIG. 66B shows a further modification of the structure shown in FIG. 66A. Instead of the eccentric cam 866 in FIG. 66A, a cam 870 with projections is used. The cam 870 with projections has an almost cylindrical shape and a plurality of projections 871 formed on the outer side surface. When the cam 870 with projections is used, the tube 863 is pressed or not pressed in accordance with the position of the projection 871 during rotation. When one projection 871 is located on the side of the movable member 869, the movable member 869 is pressed to the side of the fixed member 868 so the tube 863 is pressed. When a projection 871 is shifted from the position on the side of the movable member 869, the tube 863 is not pressed.

Alternatively, the internal rotating mechanism in a Perista pump may be applied. As a more sophisticated method, the volume in the pipe may be changed by using a piezoelectric element, or a syringe pump may be used. In this way, any other arrangement that can oscillate a biochemical solution can be applied.

FIGS. 54A to 54D are views showing the detailed structures of the tip shape of the nozzle 707.

FIGS. 54A to 54D show various modifications of the tip shape. It is effective to appropriately change the nozzle tip shape in accordance with the shape of the distal end of the packing 713.

For example, as shown in FIG. 51, when the packing 713 having the O-ring 776 formed at the distal end portion is used, the structure shown in FIG. 54A is preferably used. As shown in FIG. 54A, an outer surface 801 is formed to be flat and perpendicular to a channel 802. With this structure, the sealing properties between the nozzles and the packing 713 can be kept satisfactory, so an alignment margin against misalignment can be generated. An outer diameter $R_a$ of the nozzle 707 is about 3 mm. An inner diameter $r_a$ of the nozzle 707 is about 1 mm.

For example, when the nozzle 707 is to be inserted into the packing 713, as shown in FIG. 46 or 49, the structure shown in FIG. 54B can effectively be used. As shown in FIG. 54B, the inner diameter is constant, although the outer diameter gradually decreases from a predetermined height to the distal end portion. Hence, an outer surface 803 is tilted with respect to the channel 802 by, e.g., 15°. Accordingly, the nozzle can properly be inserted and sealed to the large-diameter opening at the distal end of each of the introduction port 752 and delivery port 753 shown in FIG. 46 or 49. In these combinations, however, the axes of the packing and the nozzle must be strictly aligned. Even when the packing shown in FIG. 49 is combined with the nozzle shown in FIG. 54A, the airtightness can sufficiently be maintained. In addition, an alignment margin can be obtained.

For example, when the distal end of the packing 713 is flat, as shown in FIG. 50, or has a recess, the structure shown in FIG. 54C is effective. As shown in FIG. 54C, the distal end portion has an O-ring 804.

For example, when the packing 713 has a distal end with an acute angle, as shown in FIG. 47, and the sealing properties are to be held inside the nozzle 707 the structure shown in FIG. 54D is effective. As shown in FIG. 54D, the inner diameter of the channel 802 is constant up to a predetermined height and then continuously increases toward the distal end.

The present invention is not limited to the above combinations. The tip shape of the nozzle 707 can be appropriately changed from the viewpoint of sealing properties and alignment margin in accordance with the shape of the introduction port 752 and delivery port 753 of the packing 713.

FIGS. 54A to 54D show the examples of the shape of the nozzle 707. This also applies to the nozzle 708.

Figure 55A:
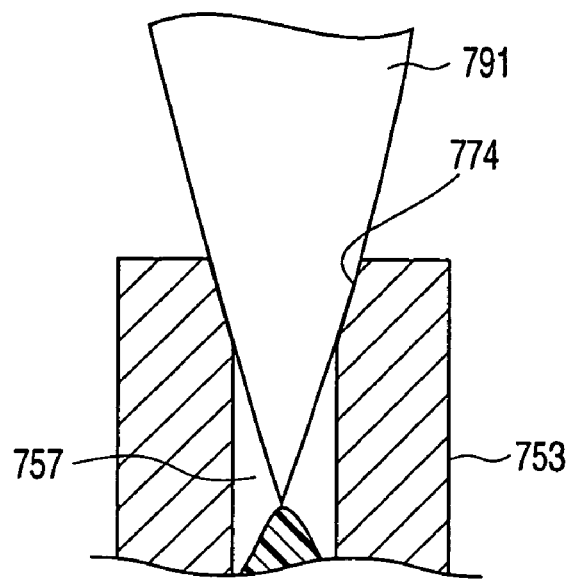
FIGS. 55A and 55B are views showing the structures of the packing and nozzle according to the second embodiment.

FIG. 55A is a view showing a sample injection operation to the delivery port 753 by using a pipette 791. Referring to FIG. 55A, the packing 713 is indicated by the delivery port 753 shown in FIG. 49. As shown in FIG. 55A, the distal end of the pipette 791 reaches the channel 757 along the inner surface 774 of the delivery port 753. The outer surface of the pipette 791 is almost in tight contact with the inner surface of the delivery port 753. If a sample is injected before the nozzle inner surface and pipette outer surface completely come into tight contact with each other, the sample may not be supplied onto the substrate 714. In addition, if the degree of contact is low, the sample does not flow downward and instead leaks upward from the delivery port 753. When the structure shown in FIG. 55A is obtained, the sample can be injected in an almost sealed state. Hence, any liquid leakage can be reduced.

Figure 55B:
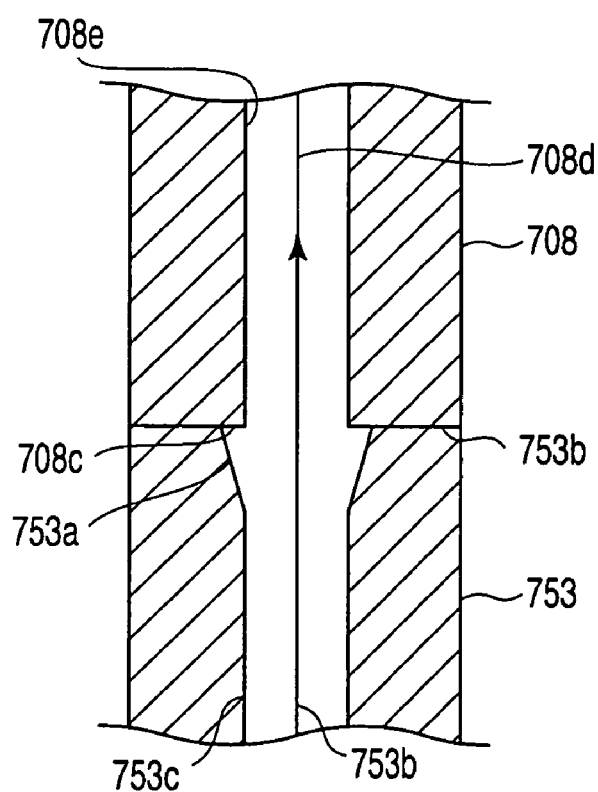

FIG. 55B shows a state wherein the nozzle 708 is pressed against the delivery port 753 and sealed. In the examples shown in FIGS. 55A and 55B, the tip shape of the delivery port 753 shown in FIG. 49 and the tip shape of the nozzle 708 shown in FIG. 54A are combined. As shown in FIG. 55B, the distal end of the nozzle 708 is pressed against the distal end of the delivery port 753. The delivery port 753 and nozzle 708 are sealed. In this state, a biochemical solution or air is transferred to the side of the nozzle 708 in the direction indicated by the arrow.

The combination of the nozzle 708 and delivery port 753 shown in FIG. 55B is supposed to be optimum, in which the upper surface of the packing and the lower surface of the nozzle are in contact and sealed. The reason why the combination shown in FIG. 55B is optimum will be described in comparison with combinations with sealing in FIGS. 74A to 74C.

Figure 74A:
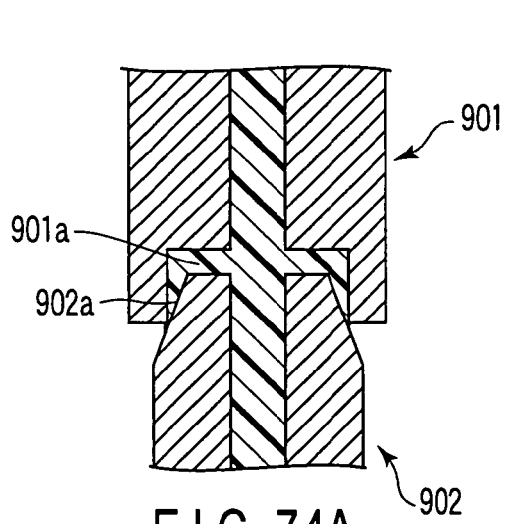
FIGS. 74A to 74C are views showing combination examples of the nozzle and packing according to the second embodiment.

FIG. 74A is a sectional view of the seal state of a nozzle 901 and a delivery port 902. The inner diameter of the opening portion at the distal end portion of the nozzle 901 is formed to be stepwise larger than that of the proximal portion closer to the valve unit 705 than the distal end portion. The distal end of the delivery port 902 is inserted and sealed to an insertion hole 901a of the distal end portion having the large inner diameter. The outer diameter of the nozzle 705 is constant.

Figure 74B:
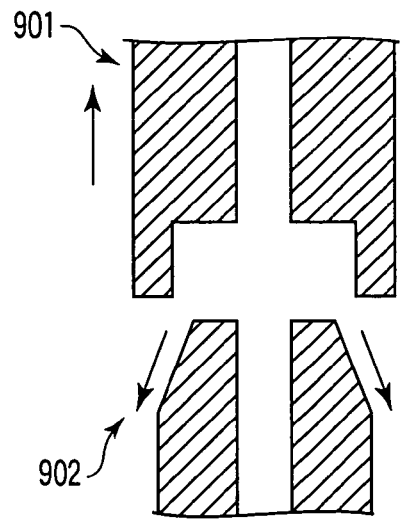

The inner diameter of the distal end of the delivery port 902 is constant while the outer diameter gradually decreases toward the distal end. That is the distal end of the delivery port 902 has a taper 902a. In the combination of the nozzle 901 and delivery port 902, even the gap between the insertion hole 901a and the outer side surface of the delivery port 902 is filled with a biochemical solution. Hence, for example, as shown in FIG. 74B, when the nozzle 901 is moved upward and separated from the delivery port 902, the biochemical solution may flow from the taper 902a on the outer side surface of the delivery port 902 and contaminate the periphery. In base sequence inspection of DNA or the like, even slight contamination may cause a determination error. Hence, such biochemical solution overflow poses a problem.

Especially, the gap between the outer wall of the delivery port 902 and the inner wall of the nozzle 901 is "hidden" from the flow of the biochemical solution. When a DNA solution in the delivery port 902 is sucked for the first time, the "hidden" portion is filled with the solution first, and then, the solution is sucked. Then, a reagent such as a cleaning solution is supplied. However, the portion where the DNA solution has entered first is "hidden" from the flow. For this reason, the solution at that portion cannot be sufficiently diluted. That is, the biochemical solution hardly circulates at the "hidden" portion.

Even after the end of inspection, the DNA solution having a relatively high concentration remains at a high probability. For this reason, the problem of contamination becomes serious. In addition, a buffered solution is often used as a reagent. When water evaporates after inspection, a crystal may be formed. In this structure, the delivery port 902 and nozzle 901 are sealed "linearly". If a crystal is generated on the sealing line, sufficient sealing is impossible. It may lead to a solution supply error such as leakage. In case of leakage, the periphery is contaminated by the liquid. In addition, the electrical system may be short-circuit.

Figure 74C:
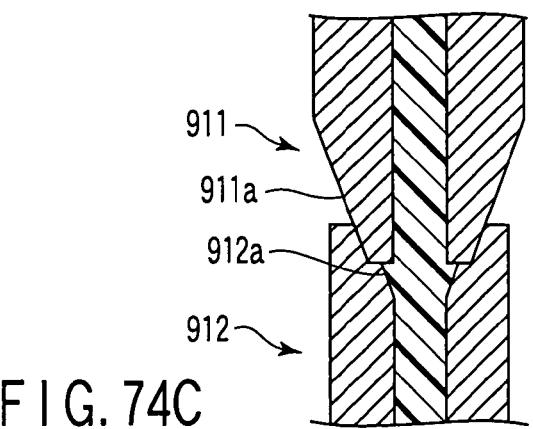

FIG. 74C shows another seal combination. A nozzle 911 has a constant inner diameter, like the delivery port 902 shown in FIG. 74A, and a taper 911a where the outer wall of the distal end portion is gradually tapered toward the distal end. On the other hand, a delivery port 912 has a constant outer diameter and a taper 912a where the inner diameter gradually increases toward the distal end. When the nozzle 911 is moved downward toward the delivery port 912, the distal end of the nozzle 911 is inserted into the taper 912a of the delivery port 912. The taper 911a of the outer side surface of the nozzle 911 and the taper 912a come into contact with each other and are sealed. In this case, the leakage of a contamination substance to the outside, which is presumed for the structure shown in FIG. 74A, does not occur. Hence, the problem of contamination is not posed.

However, alignment between the delivery port 912 and the nozzle 911 must be very strictly done. When even a slight axial shift is present between the delivery port 912 and the nozzle 911, no sufficient sealing can be ensured between the inner wall of the delivery port 912 and the nozzle 911. Hence, leakage occurs, and as a consequence, solution supply cannot be done as specified. When the combination of the nozzle 708 and delivery port 753 shown in FIG. 55B is employed for the combinations shown in FIGS. 74A to 74C, the problem is not posed.

The nozzle 708 has a central axis 708d and an inner wall 708e which has a predetermined inner diameter and is separated from the central axis 708d by a predetermined distance. The nozzle 708 also has a nozzle lower surface 708c which is almost flat and almost perpendicular to the central axis 708d. The outer diameter of the outer wall of the nozzle 708 is almost constant.

The delivery port 753 has a central axis 753d and an inner wall 753c which has a predetermined inner diameter and is separated from the central axis 753d by a predetermined distance. The inner wall 753c has a taper 753a whose inner diameter gradually increases from a halfway portion to the distal end. The delivery port 753 also has a port upper surface

753b which is almost flat and almost perpendicular to the central axis 753d. The outer diameter of the outer wall of the delivery port 753 is almost constant. As shown in FIG. 55B, the inner diameter of the inner wall 708e of the nozzle 708 is almost equal to that of the inner wall 753c of the delivery port 753. The outer wall of the nozzle 708 and each of the outer walls of the delivery port 753 are also almost equal.

According to this structure, any liquid does not come into contact with the outer wall of the delivery port 753. In addition, since the inner wall also has the taper 753a, the biochemical solution does not leak to the outside and cause contamination. Even axial alignment between the delivery port 753 and the nozzle 708 requires not so strict accuracy. No problem of sealing is posed in the range where the port upper surface 753b and nozzle lower surface 708c sufficiently come into contact. Hence, solution supply is performed as specified. Furthermore, the inner wall 753c of the delivery port 753 has a tapered shape at the distal end portion. Even when a sample is injected using the pipette 791, the pipette 791 can be smoothly inserted without making its tip hit or come into contact with any other portion. For this reason, the problem of unnecessary contamination or the like is not posed.

FIG. 55B shows the combination of the nozzle 708 and delivery port 753. This also applies to the combination of the nozzle 707 and introduction port 752. In the combination of the nozzle 707 and introduction port 752, the nozzle 707 is not used for the sample injection operation. Hence, the introduction port 752 shown in FIG. 50 may be combined with the structure shown in FIG. 54B. Alternatively, the introduction port 752 shown in FIG. 50 may be combined with the nozzle 707 shown in FIG. 54D.

Figure 72:
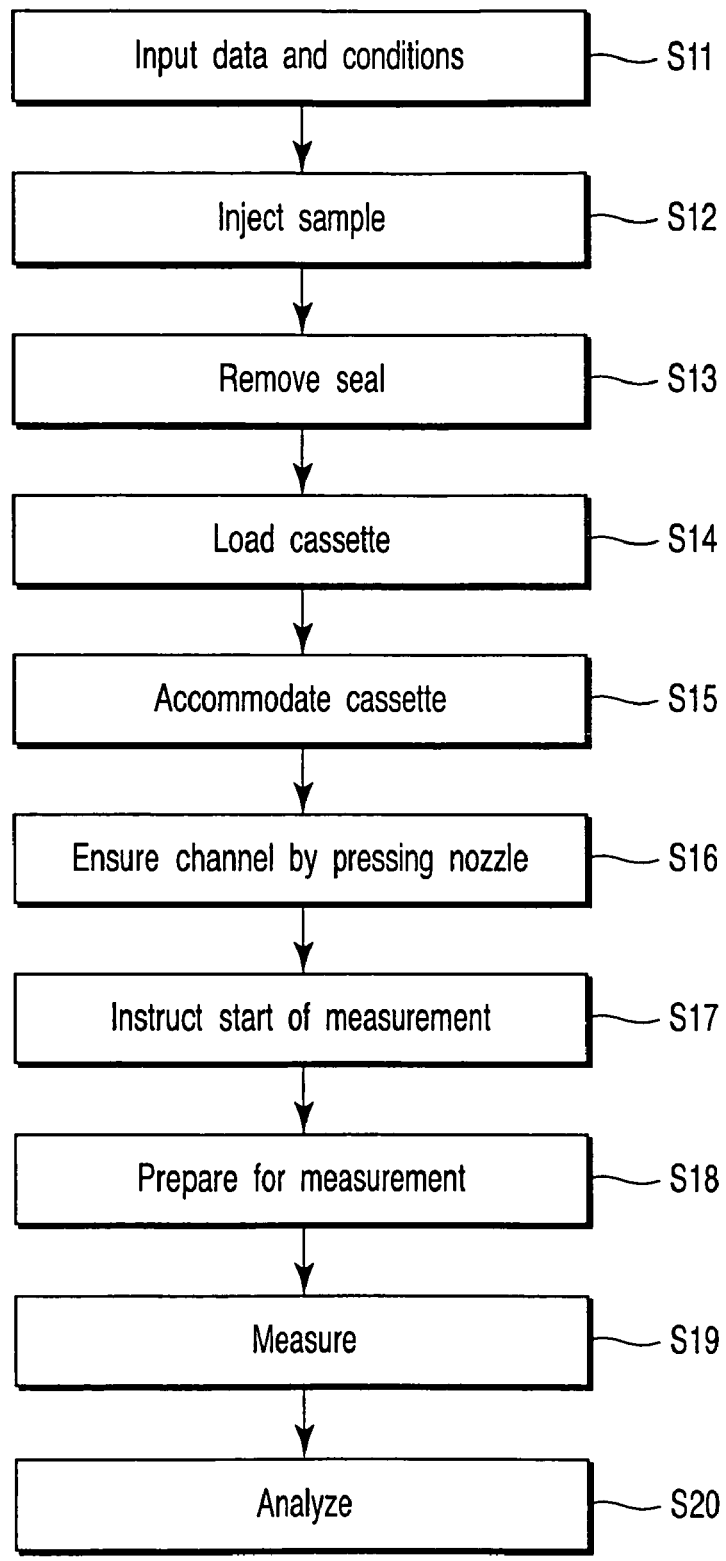
FIG. 72 is a flow chart of an automatic analyzing operation according to the second embodiment.

The outline of an automatic analyzing operation using the base sequence automatic analyzing apparatus 700 according to this embodiment will be described with reference to the flow chart shown in FIG. 72.

First, data and conditions are input on the operation window of the computer 16 (s11). Next, a sample is injected into the delivery port 753 of the cassette 703 by using the pipette 791 in the way shown in FIG. 55A (s12). The seal 750 adhered to the outer surface 741 of the cassette bottom cover 712 of the cassette 703 is peeled (s13). When the seal 750 is peeled after sample injection, the biochemical solution can be prevented from erroneously dropping to the connection port of the electric connector 730 to cause a short circuit at the time of sample injection. Hence, any operation error can be prevented.

Next, as shown in FIG. 56, in a tray open state wherein the slide stage 702a is open, the cassette 703 is loaded on the cassette loading groove 792 (s14). The button of the slide operation button 704a is pressed to accommodate the cassette 703 in the housing 701 to set a tray closed state (s15). Simultaneously with the accommodation operation, the valve unit/probe unit driving mechanisms 706a and 706b automatically drive the nozzles 707a and 708a an probe unit 710. With this operation, the nozzles 707a and 708a are pressed against the introduction port 752 and delivery port 753 so that the ports and nozzles are sealed so as not to cause liquid leakage or air leakage (s16). As a result, a closed channel is ensured between the nozzles 707a and 708a and the introduction port 752 and delivery port 753. Simultaneously, electrical contact between the electric connectors 730 and the pads 762 and 763 is ensured.

Preparation for analysis is thus done. A start instruction is input by pressing a start button on the operation window of the computer 16 (s17).

Upon receiving the start instruction, the control mechanism 15 executes measurement preparation processing (s18). The measurement preparation processing will be described later in detail. When measurement preparation processing is ended, the control mechanism 15 controls the constituent elements of the measurement system 12, solution supply system 13, and temperature control mechanism 14 on the basis of instructions from the computer 16 to execute a series of measurement operations such as hybridization, cleaning, and signal detection (s19). When the measurement is ended, the measurement result is transmitted from the control mechanism 15 to the computer 16 and analyzed. The analysis result is displayed on the display section of the computer 16, and the processing is ended (s20). The measurement and analyzing operations are the same as those of the first embodiment, and a detailed description thereof will be omitted.

Figure 70:
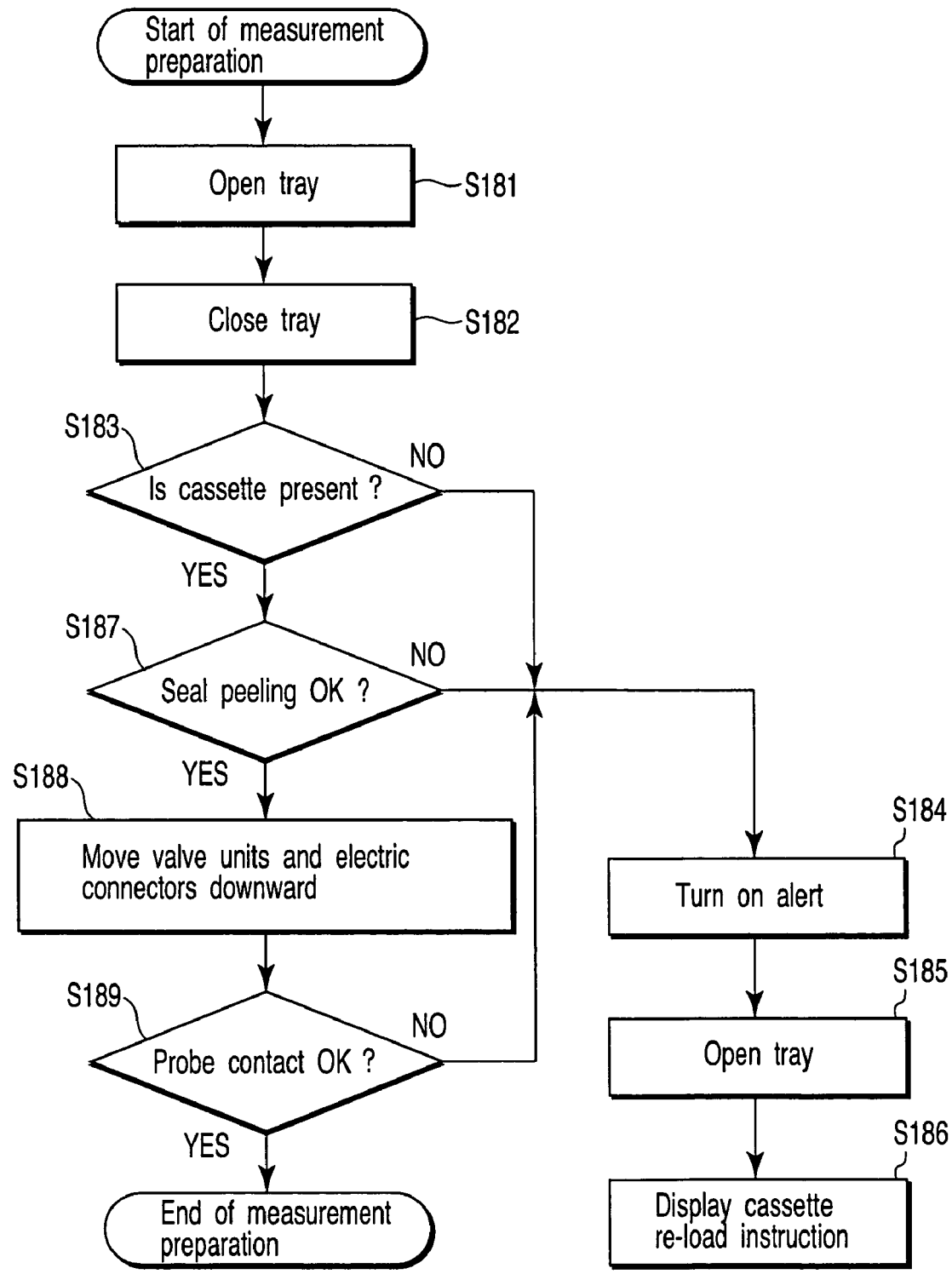
FIG. 70 is a flow chart of measurement preparation processing according to the second embodiment.

FIG. 70 is a flow chart showing an example of measurement preparation processing (s18). The measurement preparation processing (s18) shown in FIG. 70 can be executed before the measurement operation in (s19) and, for example, before (s17) (e.g., before (s14)).

First, the button of the slide operation button 704a is pressed to pull out the slide stage 702a and set the tray open state (s181). The cassette 703 is loaded (s14) and accommodated to set the tray closed state (s182). Upon detecting the tray closed state by, e.g., the driving operation of the stage driving mechanism 891, the control mechanism 15 determines the presence/absence of the cassette on the basis of the switching signal of the microswitch 811 (s183). If it is determined that no cassette is present, an alert is turned on the display section 893 (s184). The stage driving mechanism 891 is driven to slide the slide stage 702a or 702b to set the tray open state (s185). A cassette re-load instruction is displayed on the display section 893 (s186).

When it is determined by cassette determination (s183) that a cassette is present, the control mechanism 15 determines the presence/absence of a seal (s187). The presence/absence of a seal is determined by causing the detection light irradiation means 812 to emit detection light and determining whether the detection light can be detected by the detection photosensor 813. If the seal is kept unpeeled, i.e., if the detection light is not detected, the flow advances to (s184) to display an alert. The tray open state is set (s185), and a cassette re-load instruction is displayed (s186). In this case, a seal peeling instruction is preferably displayed together.

When the seal has been peeled, i.e., when the detection light is detected by the detection photosensor 813, the valve unit/probe unit driving mechanism 706a or 706b is driven to move the nozzles 707a and 708a or 707b and 708b downward and also move the electric connectors 730 downward to align them to the cassette 703 (s188).

The control mechanism 15 detects the detection signal from the electric connector 730. It is determined on the basis of the detection signal whether the probe is in contact, i.e., whether each projecting electrode 703a of the electric connector 730 and a corresponding one of the pads 762 and 763 on the substrate 714 are properly in contact with each other, and electrical connection is properly ensured (s189).

If it is determined that they are in contact, the measurement preparation processing (s18) is ended, and measurement is started (s19). If it is determined that they are not in contact, an alert is displayed (s814). The tray open state is set (s185), and a cassette re-load instruction is displayed (s186). Together with the re-load instruction, a message representing that no satisfactory contact of the electric connectors 730 is obtained is displayed as a reason for re-load. Accordingly, the user can take measures by, e.g., cleaning the surface of the substrate 714.

Although not illustrated in FIG. 70, when a sensor that detects stepwise the degree of press of the cassette type determination pin 789 is used to detect a plurality of types of cassettes, a cassette type determination step may be inserted between (s183) and (s187). In this case, the degree of press detected by the sensor is converted into data representing the type of cassette by the control mechanism 15 and displayed on the display section 893. When it is confirmed before the start of measurement that the desired cassette 703 is set, any measurement using the cassette 703 of undesired type can be prevented.

Figure 71:
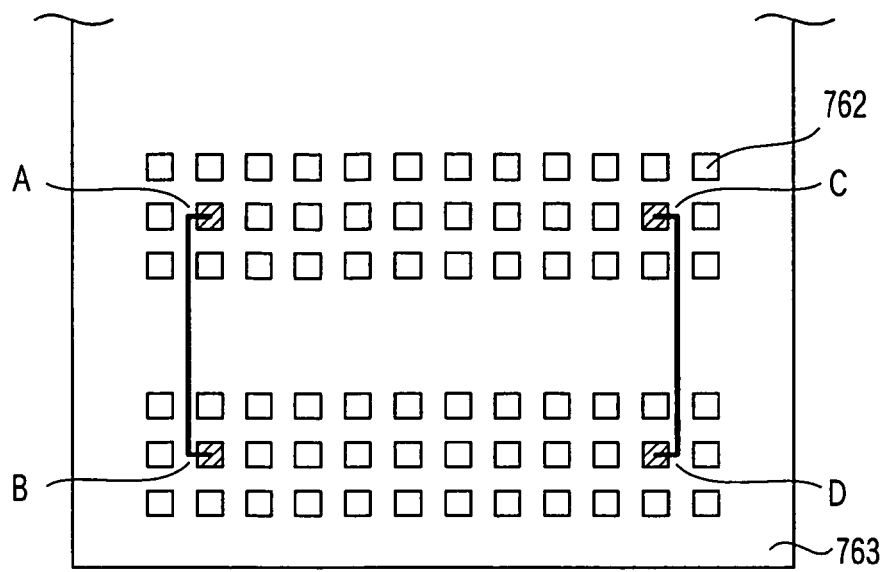
FIG. 71 is a view for explaining an electrical connection presence/absence determination method according to the second embodiment.

FIG. 71 is a view for explaining an electrical connection presence/absence determination method in (s189). As shown in FIG. 71, two pairs of pads 762 and pads 763 on the substrate 714 are short-circuited in advance in the substrate 714. That is, a total of four pads are short-circuited in advance. The electric connectors 730 are moved downward to the substrate 714. When the control mechanism 15 detects that a terminal A and a terminal B, and a terminal C and a terminal D on the side of the electric connectors 730 are short-circuited, the control mechanism 15 can determine that the electric connectors 730 and cassette 703 are properly electrically connected. To the contrary, when the control mechanism 15 cannot detect the short circuit between the terminal A and the terminal B or the short circuit between the terminal C and the terminal D, the control mechanism 15 can determine that no electrical contact is obtained between the electric connectors 730 and the cassette 703. The probe units 710a and 710b and valve units 705a and 705b move together in the vertical direction. Hence, when the presence/absence of electrical connection is determined, it can be simultaneously confirmed whether the nozzles 707a, 707b, 708a, and 708b and the introduction and delivery ports 752 and 753 obtain mechanical contact, i.e., are hermetically in tight contact with each other.

As described above, according to this embodiment, the series of measurement operations from hybridization to cleaning using buffers and electrochemical signal detection after an intercalating agent is added can be automatically and stably executed.

In this embodiment, the packing 713 integrated with solution injection and discharge ports is used. More specifically, on the side of the substrate 714, a groove to form a linear channel is formed in correspondence with the array of electrodes on the surface of the substrate 714. At two ends of the channel, the cylindrical introduction port 752 and delivery port 753, which extend perpendicularly to the surface of the substrate 714, are formed on the opposite side of the substrate 714. A solution is injected/discharged into/from the introduction port 752 and delivery port 753. The nozzles 707 and 708 of the valve unit 705 are attached to the introduction port 752 and delivery port 753 with good sealing properties. A biochemical solution or air is injected from the introduction port 752. After the biochemical solution or air flows through the channel defined by the groove 758 between the packing 713 and the substrate 714, the biochemical solution or air is discharged from the delivery port 753. The delivery port 753 also serves as a sample injection port used to inject a sample onto the surface of the substrate 714. As shown in FIG. 55A, when a sample is to be injected using the pipette 791, the tip of the pipette 791 is inserted into the delivery port 753. When the pipette 791 is inserted, the distal end portion of the pipette 791 is sealed to the channel 756, i.e., the inner wall or the delivery port 753. After sealing, the sample in the pipette 791 is pushed out slowly. Accordingly, the sample in the pipette 791 is efficiently moved onto the substrate 714.

In an arrangement different from this embodiment, i.e., when a flat packing is mounted on a substrate (chip), and a channel is formed in a cassette (chip cartridge), the channel in the cassette is long, and the amount of reagent is unnecessarily large. When a sample is injected into the cassette, the sample wastefully flows into unnecessary portions except the substrate because a long channel is present not only on the substrate but also in the cassette. In addition, the sealing properties between the cassette and the packing are poor. Leakage often occurs between the packing and the cassette, resulting in solution supply errors. When the arrangement of this embodiment is employed, the unnecessary amount of reagent decreases. In addition, since the sealing properties between the packing, the substrate, and the cassette become high, the stability of solution supply increases.

When the channel on the substrate is excessively large relative to the introduction and delivery ports, the pressure in the channel becomes lower than that in the ports. Hence, the biochemical solution easily comes to a boil, and bubbles are readily generated. The bubbles adversely affect the measurement. In this embodiment, the channel across the channel 756, groove 758, and channel 757 has an almost constant sectional area and an almost constant sectional shape. With this structure, the variation in pressure can be reduced, and boiling of the biochemical solution can be suppressed. Hence, the base sequence detection sensitivity becomes high.

When the valve unit 705 of this embodiment is used, the amount of reagent to be used for measurement can be minimized. For this reason, the running cost can be reduced.

More specifically, to introduce a reagent to an inspection portion such as a cassette or test tube, a metal needle or nozzle is often used. This is because a biochemical solution must be sucked or discharged by a needle that has pierced a rubber cap, and the needle is required to have a strength and durability to pierce the rubber. However, in detecting DNA or a base sequence, a metal needle cannot be used because metal ions cause detection errors. To the contrary, the valve unit 705 is made of PEEK or PTFE. The packing 713 is also made of silicone rubber or the like. They use no metal members. Hence, any detection error can be suppressed.

Normally, a port such as a needle or nozzle to the inspection portion and the valve that switches the reagent are connected by a tube. For this reason, a large amount of reagent exists in the tube that is not directly used for inspection. In addition, since the tube is manually attached, it is difficult to manage the length of the tube, and tube connection is unstable. As a result, the volume in the tube between valves may slightly change between apparatuses. Hence, the valve switching timing must be adjusted for each apparatus. That is, problems of an increase in reagent amount, an increase in instability of solution supply, and the necessity of valve switching timing adjustment are posed. However, when the valve unit 705 is used as in this embodiment, no tubes need be used between valves. Hence, the various problems caused by use of tubes can be solved. More specifically, the channel length can be decreased, and the necessary amount of reagent can greatly be reduced. Furthermore, since the capacity between valves can be held constant, the valve switching timing need not be adjusted for each apparatus, and solution supply stability increases.

As described above, when nozzles are made of a resin such as PEEK, and a manifold type valve unit in which the nozzles, valves, and pipes are integrated is used, the problems can be simultaneously solved.

With the valve unit 705 and cassette 703 of this embodiment, the data reproducibility can be increased.

In this embodiment, the measurement system 12, solution supply system 13, temperature control mechanism 14, and control mechanism 15 are arranged in the housing 701 shown in FIG. 35. However, the present invention is not limited to this. For example, some of the measurement system 12, solution supply system 13, temperature control mechanism 14, and control mechanism 15 may be arranged outside the housing 701. Alternatively, the computer 16 may also be arranged in the housing 701.

The bar code 744 is provided on the outer surface 741 of the cassette bottom cover 712. However, the present invention is not limited to this. For example, the bar code 744 may be provided on the outer surface 721 of the cassette top cover 711.

The channels 756 and 757 and groove 758 have almost the same sectional shape and sectional area. However, the present invention is not limited to this. For example, in all the channels 756 and 757 and groove 758, the ratio of the sectional area of the thickest portion to that of the thinnest portion is preferably about 130% or less.

FIG. 55B shows an example of the combination of the packing tip shape and nozzle tip shape. However, any combination of various modifications of the packing and nozzle tip shapes described above are available. Accordingly, the sealing properties between the packing and the nozzle can be increased.

As the materials of the nozzles 707 and 708 and valve bodies 781 and 782, PEEK and PTFE are used. However, the present invention is not limited to this. For example, any one of PFA, PC, PMMA, PPS, PBT, and PCTFE may be used. Any other resin that can be deformed by pressurization can be applied.

The valve body 781 is indicated as a manifold having three valves or four valves, and the valve body 782 is indicated as a manifold having two valves, but the present invention is not limited to the number of the valves. A manifold having at least two valves or a structure having at least two valves communicating with the nozzles 707 and 708 can be used.

In the above embodiment, both the cassette 703 and the valve unit 705 are optimized. However, the present invention is not limited to this. For example, even when only the cassette 703 is optimized in the above-described way, and a conventional valve structure is used in place of the valve unit 705, the effects of this embodiment can be obtained. Even when the valve unit 705 is optimized in the above-described way, and a conventional cassette (chip cartridge) is used in place of the cassette 703, the effects of this embodiment can be obtained.

On the substrate 714, the 3-electrode systems 761 each comprising a combination of a working electrode, counter electrode, and reference electrode are formed. However, the present invention is not limited to this. For example, as shown in FIGS. 7A, 7B, 10, or 11, counter electrodes and reference electrodes may be formed on the packing 713 while only working electrodes may be formed on the substrate 714.

The ports 752 and 753 of the cassette 703 and the nozzles 707 and 708 are positioned by making a valve unit/probe unit driving mechanism 706 drive the valve unit 705. However, the present invention is not limited to this. A cassette driving mechanism which drives and moves the cassette 703 relative to the valve unit 705 may be used in place of the valve unit/probe unit driving mechanism 706 as long as the mechanism can move the ports 752 and 753 relative to the nozzles 707 and 708.

EXAMPLES

Example 1

An example in which SNPs detection is executed by using the base sequence detection apparatus according to the above-described first embodiment will be described below. The apparatus is applied to determine whether the SNPs base sequence of an MxA-88 gene is the G/G type, T/T type, or G/T hetero.

A DNA probe having a sequence complementary to the MxA gene is immobilized to the working electrodes 501 of the base sequence detection chip. Four kinds of probe DNA fragments whose bases at SNP positions are replaced with ATGC and DNA fragments (to be referred to as negative controls) having different sequences are immobilized to different electrodes (working electrodes 501). In this case, each probe with cysteine modified to an N terminus was spotted in 200 nL and left to stand for 1 hr, thereby immobilizing the probes to the working electrodes 501 made of Au. The printed board 22 in which the base sequence detection chip 21 prepared in the above way is attached to the chip cartridge 11.

Next, DNA as a target whose base at the SNP position is G type is dissolved in 2×SSC-1 mmol/L EDTA solution and injected from the sample injection port 119 into the cell 115 by using a pipette or the like. The sample solution flows from the sample injection port 119 on the side of the delivery port 116b to the side of the introduction port 116a while filling the cell 115. The outer surface of the introduction port 116a is formed in contact with the inner surface of the sealing member 24a. For this reason, the cell 115 can be completely filled with the sample solution without forming any bubbles.

The chip cartridge 11 is attached to the apparatus main body (measurement system 12, solution supply system 13, and temperature control mechanism 14). When the apparatus program by the computer 16 is activated, all the subsequent processes are automatically executed.

The contents of automatic processing will be described. First, a reaction (hybridization) is caused at 45° C. for 15 min. After that, the solenoid valves and pump in the solution supply system 13 are controlled to supply the 0.2×SSC-1 mmol/L EDTA solution into the cell 115. The state wherein the cell 115 is filled with the solution is held at 55° C. for 30 min. Nonspecific absorption DNA that has thus absorbed to the electrodes 211 and 212 having different layouts on the base sequence detection chip 21 is cleaned. Next, 10 μmol/L Hoechst 33258 solution is supplied into the cell 115. In the state wherein the cell 115 is filled with the solution, an oxidation current from the Hoechst 33258 at each working electrode 501 is measured by the measurement system 12.

Subsequently, the computer 16 extracts a region corresponding to the oxidation current of Hoechst from the current/voltage characteristic curve by the analysis program and derives the peak current value for each electrode (working electrode 501). In addition, the computer 16 executes statistical processing such as type determination filtering in accordance with the algorithm of the analysis program, thereby determining the type of the target DNA. The obtained determination result is displayed on the display of the computer 16. As a result, it was determined that the signal intensity from an electrode corresponding to a probe whose probe sequence was C type was highest, and the base sequence at the SNP position of the target DNA was G type.

The uniformity of current values for electrodes of the same type in the plane of the base sequence detection chip 21 was 5% or less as a CV value. As a result, the SNPs detection reliability increased as compared to the conventional method.

Example 2

An example in which SNPs detection is executed by using the base sequence detection apparatus according to the above-described second embodiment will be described below. The apparatus is applied to determine whether the SNPs base sequence of an MxA-88 gene is the G/G type, T/T type, or G/T hetero.

A DNA probe having a sequence complementary to the MxA gene is immobilized to the working electrodes of the substrate 714. Four kinds of probe DNA fragments whose bases at SNP positions are replaced with ATGC and DNA fragments (to be referred to as negative controls) having different sequences are immobilized to different working electrodes. In this case, each probe with cysteine modified to an N terminus was spotted in 200 nL and left to stand for 1 hr, thereby immobilizing the probes to the working electrodes made of Au. The thus prepared substrate 714 is attached to the cassette 703.

Next, DNA as a target whose base at the SNP position is G type is dissolved in 2×SSC-1 mmol/L EDTA solution and injected from the introduction port 752 into the channel (cell) defined by the groove 758 and substrate 714 by using the pipette 791.

The cassette 703 is placed on the slide stage 702 and accommodated in the housing 701. When the apparatus program by the computer 16 is activated, all the subsequent processes are automatically executed.

The contents of automatic processing will be described. First, a reaction (hybridization) is caused at 45° C. for 15 min. After that, the solenoid valves and pump in the solution supply system 13 are controlled to supply the 0.2×SSC-1 mmol/L EDTA solution into the cell. The state wherein the cell is filled with the solution is held at 55° C. for 30 min. Nonspecific absorption DNA that has thus absorbed to the electrodes having different layouts on the substrate 714 is cleaned. Next, 10 μmol/L Hoechst 33258 solution is supplied into the cell. In the state wherein the cell is filled with the solution, an oxidation current from the Hoechst 33258 at each working electrode is measured by the measurement system 12.

Subsequently, the computer 16 extracts a region corresponding to the oxidation current of Hoechst from the current/voltage characteristic curve by the analysis program and derives the peak current value for each working electrode. In addition, the computer 16 executes statistical processing such as type determination filtering in accordance with the algorithm of the analysis program, thereby determining the type of the target DNA. The obtained determination result is displayed on the display of the computer 16. As a result, it was determined that the signal intensity from an electrode corresponding to a probe whose probe sequence was C type was highest, and the base sequence at the SNP position of the target DNA was G type.

The uniformity of current values for electrodes of the same type in the plane of the substrate 714 was 3% or less as a CV value. As a result, the SNPs detection reliability increased as compared to the conventional method.

As described above in detail, according to the embodiments, the uniformity of electrochemical reaction characteristics increases, and the detection reliability increases.

In addition, since a whole process including base sequence detection and analysis of detected data can be automatically executed, the data or measurement reproducibility increases.

As has been described above, the present invention is effective in the technical field of the base sequence detection apparatus which detects a base sequence and the technical field of the base sequence automatic analyzing apparatus which detects a base sequence.

What is claimed is:
1. An analyzing apparatus comprising:
(a) a detection unit formed as a cassette and which detects a target base sequence in a sample solution on the basis of a reaction between the target base sequence in the sample solution and a probe base sequence, the detection unit including:
  a substrate on which a channel is formed, the sample solution, a first reagent solution, a second reagent solution, or air being supplied to the channel,
  a working electrode arranged in the channel with the probe base sequence immobilized thereon,
  a counter electrode which is arranged in the channel,
  a reference electrode which is arranged in the channel, and
  a sealing member which seals the channel on the substrate, which has inlet and outlet ports communicating with the channel;
(b) a main apparatus on which the detection unit is attachably provided, the main apparatus including:
  a bypass provided in parallel with the channel of the detection unit, when the detection unit is attached to the main apparatus to detect the target base sequence;
  a supply unit including:
    a first supply valve which switches between supplying the first reagent solution and air to be supplied into the channel through the inlet port,
    a second supply valve which switches between supplying the second reagent solution and air to be supplied into the channel through the inlet port,
    a first nozzle attachably coupled to the inlet port and in communication with the inlet port when the detecting unit is attached to the main apparatus to detect the target base sequence, and
    a first valve, connected to the first and second supply valves and connected to the first nozzle and the bypass, to selectively supply one of the first and second reagent solutions and air into either one of the first nozzle or the bypass;
  a discharge unit including:
    a second nozzle attachably coupled to the outlet port and in communication with the outlet port when the detecting unit is attached to the main apparatus to detect the target base sequence,
    a second valve, connected to the second nozzle and the bypass, to selectively receive the reagent solution and air from either one of the second nozzle or the bypass, and
    a pump in communication with the second valve to suck the reagent
  solution and air to be discharged;
the main apparatus further comprising:
(i) a measurement unit which applies a voltage between the working electrode and the counter electrode and detects an electrochemical reaction signal from the working and the counter electrodes the measurement unit including:
  a voltage pattern generator which generates a voltage having a pattern,
  a feedback circuit which feeds back a voltage from the reference electrode,
  an amplifier which amplifies a voltage which is generated on the basis of the voltages from the voltage pattern generator and the feedback circuit, and applies the amplified voltage to the counter electrode, and
(ii) a temperature control unit which controls a temperature of the detection unit;

(iii) a control unit which controls the supply unit, the discharge unit, the measurement unit, and the temperature control unit;

(iv) a memory unit which stores the electrochemical reaction signal as measurement data; and (v) a processing unit which processes the measurement data to determine the target base sequence.

2. The analyzing apparatus according to claim 1, wherein the sealing member has a sample injection port through which the sample solution is injected into the channel.

3. The analyzing apparatus according to claim 1, wherein the supply unit further includes a third supply valve which switches between supplying a third reagent solution and air to be supplied into the channel through the inlet port, and the first valve is connected to the third supply valve to selectively supply one of the first, second or third reagent solutions or air into either one of the first nozzle and the bypass.

4. The analyzing apparatus according to claim 3, wherein the supply unit further includes:

an air supply source which supplies air to the first supply valve connected between the first valve and the air supply source;

a first supply source which supplies first reagent solution to the first supply valve connected between the first valve and the first supply source;

a second supply source which supplies second reagent solution to the second supply valve connected between the first valve and the second supply source; and a third supply source which supplies third reagent solution to the third supply valve connected between the first valve and the third supply source.

5. The analyzing apparatus according to claim 1, wherein the supply unit further includes:

an air supply source which supplies air to the first supply valve connected between the first valve and the air supply source;

a first supply source which supplies first reagent solution to the first supply valve connected between the first valve and the first supply source; and a second supply source which supplies second reagent solution to the second supply valve connected between the first valve and the second supply source.

6. The analyzing apparatus according to claim 1, wherein the first supply valve is alternatively switched to supply air and the first reagent solution so that a first alternation flow of air and the first reagent solution is sequentially supplied into the channel, and the second supply valve is alternatively switched to supply air and the second reagent solution so that a second alternation flow of air and the second reagent solution is sequentially supplied into the channel.

7. The analyzing apparatus according to claim 1, the main apparatus further comprising (iv) a protective circuit that prevents excessive voltage that electrolyzes a solution from being applied at a time of measurement and that comprises a resistance arranged in parallel with the amplifier or between the amplifier and the counter electrode, and a switch that ON/OFF-controls a current that flows to the resistance.

* * * * *